(12) United States Patent
Borowsky et al.

(10) Patent No.: US 7,517,658 B2
(45) Date of Patent: *Apr. 14, 2009

(54) METHODS FOR PREPARING COMPOSITIONS USING A SNORF33 RECEPTOR

(75) Inventors: Beth E. Borowsky, Flemington, NJ (US); Kristine L. Ogozalek, Rochelle Park, NJ (US); Kenneth A. Jones, Glen Rock, NJ (US)

(73) Assignee: H. Lundbeck A/S, Valby-Copenhagen (DK)

( * ) Notice: Subject to any disclaimer, the term of this patent is extended or adjusted under 35 U.S.C. 154(b) by 277 days.

This patent is subject to a terminal disclaimer.

(21) Appl. No.: 11/227,855

(22) Filed: Sep. 15, 2005

(65) Prior Publication Data

US 2007/0028315 A1    Feb. 1, 2007

Related U.S. Application Data

(63) Continuation of application No. 09/980,145, filed as application No. PCT/US00/14654 on May 26, 2000, now Pat. No. 6,987,005, which is a continuation-in-part of application No. 09/413,433, filed on Oct. 6, 1999, now abandoned, which is a continuation-in-part of application No. 09/322,257, filed on May 28, 1999, now abandoned.

(51) Int. Cl.
*G01N 33/567* (2006.01)
*G01N 33/53* (2006.01)
*C07K 14/47* (2006.01)

(52) U.S. Cl. .................. 435/7.1; 435/7.2; 435/7.21; 436/501; 530/350; 536/23.5

(58) Field of Classification Search .................. None
See application file for complete search history.

(56) References Cited

U.S. PATENT DOCUMENTS

| 3,373,081 | A | 3/1968 | Engleman et al. |
| 6,043,283 | A | 3/2000 | Giulian et al. |
| 2002/0193584 | A1 | 12/2002 | Chen et al. |
| 2003/0105318 | A1 | 6/2003 | Borowsky et al. |
| 2006/0074233 | A1 | 4/2006 | Borowsky et al. |

FOREIGN PATENT DOCUMENTS

| EP | 0859055 | 8/1998 |
| GB | 2312211 | 10/1997 |
| WO | WO 97/40148 | 10/1997 |
| WO | WO 00/18438 | 4/2000 |
| WO | WO 00/50562 | 8/2000 |

OTHER PUBLICATIONS

U.S. Appl. No. 09/980,145, filed Apr. 12, 2002, Borowsky, et al.
Davis and Boulton, (1994) "The Trace Amines and Their Acidic Metabolites in Depression—An Overview" Prog. Neuro-psychopharmacol. & Biol. Psychiat. 18: 17-45.
Stam et al. (1996) "Molecular Cloning and Characterization of a Novel Orphan Receptor (P2P) Expressed in Human Pancreas That Shows High Structural Homology to the P2U Purinoceptor" FEBS Letters 384(3): 260-264.
Bunzow et al. (2000) Locus AF200627, GenEmbl Database.
Lee, D.K., et al. (2000) "Cloning and Characterization of Additional Members of the G Protein-coupled Receptor Family" Biochimica et Biophysica Acta. Gene structure and Expression, Amsterdam 1490(3): 311-323.
Borowsky, B., et al. (2001) "Trace Amines: Identification of a Family of Mammalian G Protein-coupled Receptors" Proc Natl Acad Sci U.S.A. 98(16): 8966-71.
U.S. Appl. No. 09/322,257, filed May 28, 1999, Borowsky et al.
U.S. Appl. No. 09/413,433, filed Oct. 6, 1999, Borowsky et al.

*Primary Examiner*—Bridget E Bunner
*Assistant Examiner*—Fozia M Hamud
(74) *Attorney, Agent, or Firm*—Stephen G. Kalinchak; Margaret M. Buck

(57) ABSTRACT

This invention provides isolated nucleic acids encoding mammalian SNORF33 receptors, purified mammalian SNORF33 receptors, vectors comprising nucleic acid encoding mammalian SNORF33 receptors, cells comprising such vectors, antibodies directed to mammalian SNORF33 receptors, nucleic acid probes useful for detecting nucleic acid encoding mammalian SNORF33 receptors, antisense oligonucleotides complementary to unique sequences of nucleic acid encoding mammalian SNORF33 receptors, transgenic, nonhuman animals which express DNA encoding normal or mutant mammalian SNORF33 receptors, methods of isolating mammalian SNORF33 receptors, methods of treating an abnormality that is linked to the activity of the mammalian SNORF33 receptors, as well as methods of determining binding of compounds to mammalian SNORF33 receptors, methods of identifying agonists and antagonists of SNORF33 receptors, and agonists and antagonists so identified.

8 Claims, 28 Drawing Sheets

FIGURE 1

```
  1  ACTGTGGACTTTCTCTGGGTGTCTCTGGTCATGCCTTACAGTATGGTGAGATCTGCTGAG    60
 61  CACTGTTGGTATTTTGGAGAAGTCTTCTGTAAAATTCACACAAGCACCGACATTATGCTG   120
121  AGCTCAGCCCTCCATTTTCCATTGTCTTTTCATCTCCATTGACCGCTACTATGCTGTGT   180
181  GATCCACTGAGATATAAAGCCAAGATGAATATCTTGGTTATTTGTGTGATGATCTTCATT   240
241  AGTTGGAGTGTCCCTGCTGTTTTTGCATTTGGAATGATCTTTCTGGAGCTAAACTTCAAA   300
301  GGCGCTGAAGAGATATATTACAAACATGTTCACTGCAGAGGAGGTTGCTCTGTCTTCTTT   360
361  AGCAAAATATCTGGGGTACTGACCTTCTTTTATATACCTGGATCTTATTATG          420
421  TTATGTGTCTATTACAGAATATATCTTATCGCTAAAGAACAGGCAAGATTAATTAGTGAT   480
481  GCCAATCAGAAGCTCCAAATTGGAATGAAAATGGAATTTCACAAAGCAAGAA          540
541  AGGAAAGCTGTGAAGACATTGGGGATTGTGATG                              573
```

```
  1  ATTGCTCGACAGCCAAAGGGACAGAGCAGCCTGTGTTTAGTTCTCTGTAGTGATGCATCT    60
 61  TTGCCACAATAGCGCGAATATTCCCACACGAACAGCAACTGGTCAAGGATGTCCGTGC    120
121  TTCGCTGTACAGCTTAATATCACTCATAATTCTAACCACTCTGGTTGGCAACTTAATAGT   180
181  AATCATTTCGATATCCCACTTCAAGCAACTTCACACGCCCACAAATTGGCTCCTTCATTC   240
241  CATGGCCGTGTCTGACTTTCTGCTGGGCGTGTCTGTCATGCCCTACAGCATGGTGAGAAC   300
301  AGTTGAGCACTGCTGGTACTTTGGGGAACTCTTCTGCAAACTTCACACCAGCACTGATAT   360
361  CATGCTGAGCTCGGCATCCATTCTCCACCTAGCCCTTCATTCCATTGACCGCTACTATGC   420
421  TGTGTGCGACCCTTTAAGATACAAAGCCAAGATCAATCTCGCCGCCATTTTTGTGATGAT   480
481  CCTCATTAGCTGGAGCCTTCCTGCTGTTTTTGCATTGGGATGATCTTCCTGGAGCTGAA   540
541  CTTAGAAGGAGTTGAGGAGCTGTATCACAATCAGTCTTCTGCCTGCGCGGCTGTTTTCC   600
601  CTTCTTCAGTAAAGTATCTGGGTACTGGCATTCATGACGTCTTTCTATATACCTGGATC   660
```

FIGURE 3B

```
 661  TGTTATGTTATTTGTTACTATAGAATATATTTCATAGCTAAAGGACAAGCAAGGTCAAT   720
 721  TAATCGTGCAAATCTTCAAGTTGGATTGGAAGGGAAAGCAGAGCGCCACAAAGCAAGGA   780
 781  AACAAAAGCCGCGAAAACCTTAGGGATCATGGTGGGCGTTTCCTCCTGTGCTGGTGCCC   840
 841  GTCTTTTTCTGCATGGTCCTGACCCTTTCCTGGGCTATGTTATCCCACCCACTCTGAA   900
 901  TGACACACTGAATTGGTTTGGGTACCTGCCTTCAACCTGCGATGGTTTATGCCTT      960
 961  TTTCTATCCCTGGTTCAGAGAGCGTTGAAGATGGTTCTCTCTTCGGTAAAATTTCCAAAA  1020
1021  AGATTCATCTAGTCTAAGTTATTTTTGTAACGCAATCCATGAAACCAGTATATTTGTA  1080
1081  GTTCTTAAGAGCAGTTGGTGA                                        1101
```

```
  1  TCAGGAATGATGCCCTTTTGCCCACAATATAATTAATATATTTCCTGTGTGAAAAACAACTGG   60
 61  TCAAATGATGTCCGTGCTTCCCTGTACAGTTAATGGTGCTCATAATTCTGACCACACTC     120
121  GTTGGCAATCTCGATAGTTATTGTTTCTATATCACACTTCAAACAACTTCATACCCCAACA   180
181  AATTGGCTCATTCATTCCATGGCCACTGTGGACTTTCTTCTGGGGTGTCTGGTCATGCCT   240
241  TACAGTATGGTGAGATCTGCTGAGCACTGTGGTATTTTGGAGAAGTCTTCTGTAAAATT   300
301  CACACAAGCACCGACATTATGCTGAGCTCAGCCTCCATTTTCCATTTGTCTTTCATCTCC   360
361  ATTGACCGCTACTATGCTGTGTGTGATCTTCATTAGTTGGAGTGTCCCTGCTGTTTTGCATTGGAATG   420
421  GTTATTTGTGTGATGATCTTCATTAGTTGGAGTGTCCCTGCTGTTTTGCATTGGAATG   480
481  ATCTTTCTGGAGCTAAACTTCAAAGGCGCTGAAGAGATATATTACAAACATGTTCACTGC   540
541  AGAGGAGGTTGCTCTGTCTTCTTTAGCAAAATATCGGGTACTGACCTTTATGACTTCT   600
601  TTTTATATACCTGGATCTATTATGTGTCTATTACAGAATATATCTTATCGCTAAA   660
```

FIGURE 5B

```
 661  GAACAGGCAAGATTAATTAGTGATGCCAATCAGAAGCTCCAAATTGGATTGGAAATGAAA   720
 721  AATGGAATTTCACAAAGCAAAGAAAGGAAAGCTGTGAAGACATTGGGGATTGTGATGGGA   780
 781  GTTTTCCTAATATGCTGGTGCCCCTTTCTCTTTATCTGTACAGTCATGGACCCTTTCTTCAC  840
 841  TACATTATTCCACCTACTTTGAATGATGTGTTGATTTGGTTTGGCTACTTGAACTCTACA   900
 901  TTTAATCCAATGGTTTATGCATTTTTCTATCCTTGGTTTAGAAAAGCACTGAAGATGATG   960
 951  CTGTTTGGTAAAATTTTCCAAAAAGATTCATCCAGGTGTAAATTATTTTTGGAATTGAGT  1020
1021  TCATAGAATTATTATATT                                            1038
```

```
Rat SNORF33    1  .MHLCHNSANISHTNSNWSRDVRASLYSLISLIITTLVGNLIVIISISH  49
                   |||    |||   .||  |||||||||||||:||||
Hum SNORF33    1  MMPFCHNIINISCVKNNWSNDVRASLYSLMVLILTTLVGNLIVISISH  50

Rat SNORF33   50  FKQLHTPTNWLLHSMAVVDFLLGCLVMPYSMVRTVEHCWYFGELFCKLHT  99
                  ||||||||||||:|||||.||||||||||||||||.||:||
Hum SNORF33   51  FKQLHTPTNWLIHSMATVDFLLGCLVMPYSMVRSAEHCWYFGEVFCKIHT  100

Rat SNORF33  100  STDIMLSSASILHLAFISIDRYYAVCDPLRYKAKINLAAIFVMILISWSL  149
                  |||||||||:|||.|||||||||||||||||||||.|:    ||| |||.
Hum SNORF33  101  STDIMLSSASIFHLSFISIDRYYAVCDPLRYKAKMNILVICVMIFISWSV  150

Rat SNORF33  150  PAVFAFGMIFLELNLEGVEELYHNQVFCLRGCFPFFSKVSGVLAFMTSFY  199
                  |||||||||||||||:|||:|:|||   ||  || |||:|||||||:||||||
Hum SNORF33  151  PAVFAFGMIFLELNFKGAEEIYYKHVHCRGGCSVFFFSKISGVLTFMTSFY  200

Rat SNORF33  200  IPGSVMLFVYYRIYFIAKGQARSINRAN..LQVGLEGESRAPQSKETKAA  247
                  ||||:||.||||||||||| |||  ||.. |:|||    ||
Hum SNORF33  201  IPGSIMLCVYYRIYLIAKEQARLISDANQKLQIGLEMKNGISQSKERKAV  250
```

FIGURE 7B

```
Rat SNORF33  248 KTLGIMVGVFLLCWCPFFFCMVLDPFLGYVIPPTLNDTLNWFGYLNSAFN 297
                 ||||:||:||:||||||:||..:|||||:||  |:|||  |||||||:||
Hum SNORF33  251 KTLGIVMGVFLICWCPFFICTVMDPFLHYIIPPTLNDVLIWFGYLNSTFN 300

Rat SNORF33  298 PMVYAFFYPWFRRALKMVLFGKIFQKDSSRSKLFL.....* 333
                 ||||||||||||:||||:||||||||||||||:|||
Hum SNORF33  301 PMVYAFFYPWFRKALKMMLFGKIFQKDSSRCKLFLELSS*  340
```

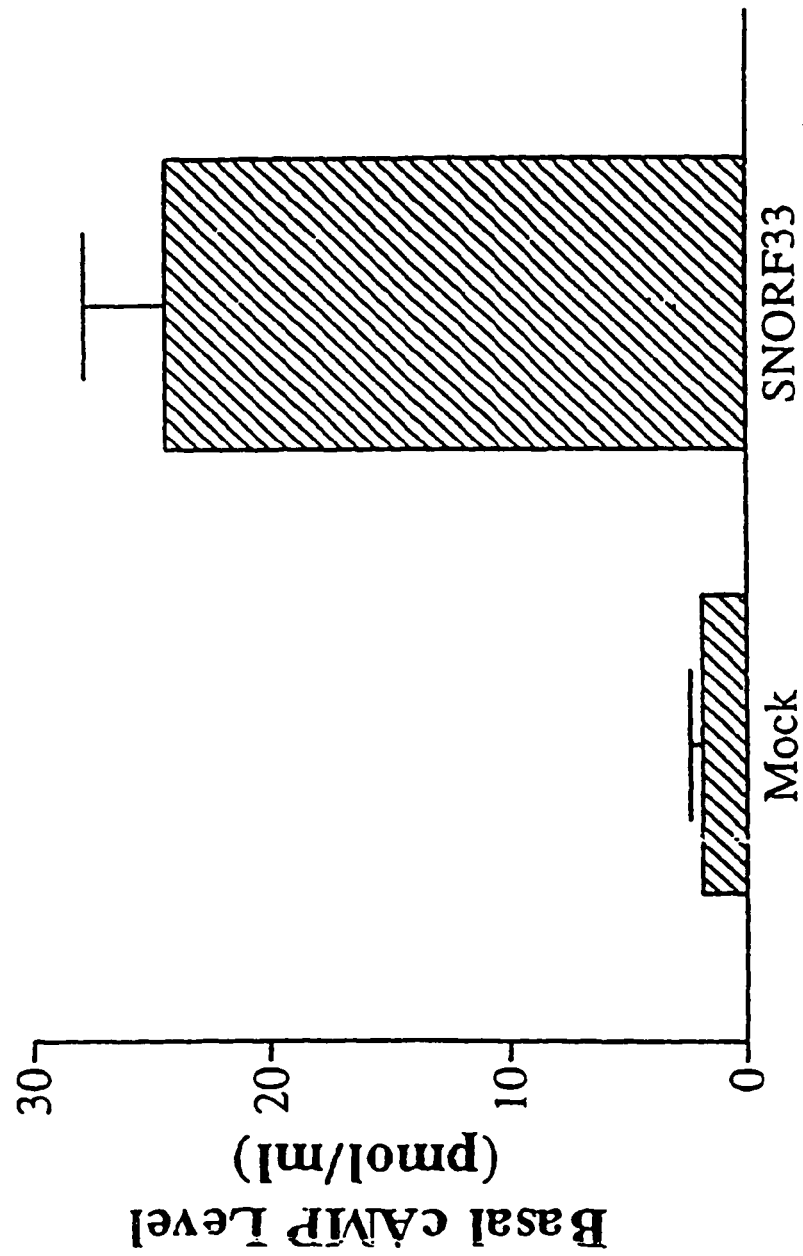

Agonist-Mediated Increase in Intracellular cAMP Levels in Mock- and rat SNORF33-Transfected Cos-7 Cells Agonist-Mediated Increase in Intracellular cAMP Levels in Mock- and rat SNORF33-Transfected Cos-7 Cells

Figure 17

```
1    GGTACTGGCGTTCATGACTTCCTTCTATATACCTGGATCTGTGTATGTTATTTGTTTACTA    60
61   TAGGATATATTTCATAGCTAAAGGACAAGCAAGTCAATCAATCGTACGAATGTTCAAGT    120
121  TGGATTGGAAGGGAAAAGCCAAGCACCACAAAGCAAGGAAACAAAAGCCGGAAGACCTT    180
181  AGGGATCATGGTGGGCGTTTTCCTCGTATGCTGGTGCCCGTTCTTTCTCTGCACGGTCCT    240
241  GGACCCTTTCCT                                                    252
```

```
  1  TGCAGTGATGCATCTTTGCCACGCTATCACAAACATTTCCCACAGAAACAGCGACTGGTC   60
 61  AAGAGAAGTCCAAGCTTCCCTGTACAGCTTAATGTCACTCATAATCCTGGCCACTCTGGT  120
121  TGGCAACTTAATAGTAATAATTTCCATATCCCATTTCAAGCAACTTCATACACCCACCAA  180
181  CTGGCTCCTTCACTCCATGGCCATTGTCGACTTTCTGCTGTGTCTGATAATGCCCTG      240
241  CAGCATGGTGAGAACTGTTGAGCGCTGTGTTTTGGGAAATCCTCTGTAAAGTTCA        300
301  CACCAGCACCGATATCATGCTGAGCTCCGCCCTCCATTTCCCACTTAGCTTTCATTTCCAT 360
361  TGACCGCTACTGTGTGCTGTGTGTGACCCTTTGAGATACAAAGCCAAGATCAATATCTCCAC 420
421  TATTCTGTGATGATCCTTCGTTAGTTGGAGCCTTCCCTGCTGTTATGCATTGGGATGAT   480
481  CTTCCCTGGAACTGAACTTAAAAGGAGTGGAAGAGCTGTATCGCAGTCAGGTCAGCGACCT 540
541  GGGCGGCTGTTCTCCCCTTCTCTTTAGTAAAGTATCTGGGGTACTGGCGTTCATGACTTCCTT 600
```

FIGURE 19B

```
601   CTATATACCTGGATCTGTGTTATGTTATTGTTTACTATAGGATATATTTCATAGCTAAAGG   660
661   ACAAGCAAGTCAATCAATCGTACGAATGTTCAAGTTGGATTGGAAGGGAAAAGCCAAGC    720
721   ACCACAAAGCAAGGAAACAAAGCCCGAAGACCTTAGGGATCATGGTGGGCCGTTTTCCT    780
781   CGTATGCTGGTGCCCGTTCTTCTCTGCACGGTCCTGGACCCTTTCCTGGGCTATGTTAT    840
841   CCCACCCTCTCTGAATGACGCACTGTATTGGTTTGGGTACTTGAATTCTGCCCTCAATCC   900
901   GATGGTTTATGCCTTTTTCTATCCCCTGGTTCAGAAGAGCCTTGAAGATGGTTCTCCTTGG   960
961   TAAAATTTCCAAAAAGATTCATCTAGGTCTAAGCTATTTTTGTAACGCAATTCATGAAA   1020
1021  CCCATGTATTT                                                   1031
```

```
Rat    SNORF33    -MhlCHnsaN  IShtnsnWSr  dVrASLYSLi  sLIILtTLVG
Mouse  SNORF33    -MhlCHaitN  IShrnsdWSr  eVqASLYSLm  sLIILaTLVG
Human  SNORF33    mMpfCHniiN  IScvknnWSn  dVrASLYSLm  vLIILtTLVG
Consensus         -M--CH---N  IS-----WS-  -V-ASLYSL-  -LIIL-TLVG Rat    SNORF33    NLIVIiSISH  FKQLHTPTNW  LlHSMAvVDF  LLGCLvMPyS
Mouse  SNORF33    NLIVIiSISH  FKQLHTPTNW  LlHSMAiVDF  LLGCLiMPcS
Human  SNORF33    NLIVIvSISH  FKQLHTPTNW  LiHSMAtVDF  LLGCLvMPyS
Consensus         NLIVI-SISH  FKQLHTPTNW  L-HSMA-VDF  LLGCL-MP-S Rat    SNORF33    MVRtvEhCWY  FGElfCKlHT  STDIMLSSAS  IlHLaFISID
Mouse  SNORF33    MVRtvErCWY  FGEilCKvHT  STDIMLSSAS  IfHLaFISID
Human  SNORF33    MVRsaEhCWY  FGEvfCKiHT  STDIMLSSAS  IfHLsFISID
Consensus         MVR--E-CWY  FGE--CK-HT  STDIMLSSAS  I-HL-FISID Rat    SNORF33    RYyAVCDPLR  YKAKiNlaaI  fVMIliSWSl  PAVfAFGMIF
Mouse  SNORF33    RYcAVCDPLR  YKAKiNistI  lVMIlvSWSl  PAVyAFGMIF
Human  SNORF33    RYyAVCDPLR  YKAKmNilvI  cVMIfiSWSv  PAVfAFGMIF
Consensus         RY-AVCDPLR  YKAK-N---I  -VMI--SWS-  PAV-AFGMIF Rat    SNORF33    LELNleGvEE  lYhnqVfclr  GCfpFFSKvS  GVLaFMTSFY
Mouse  SNORF33    LELNlkGvEE  lYrsqVsdlg  GCspFFSKvS  GVLaFMTSFY
Human  SNORF33    LELNfkGaEE  iYykhVhcrg  GCsvFFSKiS  GVLtFMTSFY
Consensus         LELN--G-EE  -Y---V----  GC--FFSK-S  GVL-FMTSFY Rat    SNORF33    IPGSvMLfVY  YRIYfIAKgQ  ARsInraN..  lQvGLEgesr
Mouse  SNORF33    IPGSvMLfVY  YRIYfIAKgQ  ARsInrtN..  vQvGLEgksq
Human  SNORF33    IPGSiMLcVY  YRIYlIAKeQ  ARlIsdaNqk  lQiGLEmkng
Consensus         IPGS-ML-VY  YRIY-IAK-Q  AR-I---N--  -Q-GLE----

Rat    SNORF33    apQSKEtKAa  KTLGImvGVF  LlCWCPFFfC  mVlDPFLgYv
Mouse  SNORF33    apQSKEtKAa  KTLGImvGVF  LvCWCPFFlC  tVlDPFLgYv
Human  SNORF33    isQSKErKAv  KTLGIvmGVF  LiCWCPFFiC  tVmDPFLhYi
Consensus         --QSKE-KA-  KTLGI--GVF  L-CWCPFF-C  -V-DPFL-Y-

Rat    SNORF33    IPPtLNDtLn  WFGYLNSafN  PMVYAFFYPW  FRrALKMvLf
Mouse  SNORF33    IPPsLNDaLy  WFGYLNSalN  PMVYAFFYPW  FRrALKMvLl
Human  SNORF33    IPPtLNDvLi  WFGYLNStfN  PMVYAFFYPW  FRkALKMmLf
Consensus         IPP-LND-L-  WFGYLNS--N  PMVYAFFYPW  FR-ALKM-L-

Rat    SNORF33    GKIFQKDSSR  sKLFL
Mouse  SNORF33    GKIFQKDSSR  sKLFL
Human  SNORF33    GKIFQKDSSR  cKLFLelss
Consensus         GKIFQKDSSR  -KLFL----
```

METHODS FOR PREPARING COMPOSITIONS USING A SNORF33 RECEPTOR

This application is a continuation of U.S. Ser. No. 09/980,145, filed Apr. 12, 2002, now U.S. Pat. No. 6,987,005, issued Jan. 17, 2006, which is a §371 National Stage filing of PCT International Application No. PCT/US00/14654, filed May 26, 2000, which claims priority of and is a continuation-in-part of U.S. Ser. No. 09/413,433, filed Oct. 6, 1999, now abandoned, which is a continuation-in-part of U.S. Ser. No. 09/322,257, filed May 28, 1999, now abandoned, the contents of all of which are hereby incorporated by reference into the subject application.

BACKGROUND OF THE INVENTION

Throughout this application various publications are referred to by partial citations within parentheses. Full citations for these publications may be found at the end of the specification immediately preceding the claims. The disclosures of these publications, in their entireties, are hereby incorporated by reference into this application in order to describe more fully the state of the art to which the invention pertains.

Neuroregulators comprise a diverse group of natural products that subverse or modulate communication in the nervous system. They include, but are not limited to, neuropeptides, amino acids, biogenic amines, lipids, and lipid metabolites, and other metabolic byproducts. Many of these neuroregulator substances interact with specific cell surface receptors, which transduce signals from the outside to the inside of the cell. G-protein coupled receptors (GPCRs) represent a major class of cell surface receptors with which many neurotransmitters interact to mediate their effects. GPCRs are characterized by seven membrane-spanning domains and are coupled to their effectors via G-proteins linking receptor activation with intracellular biochemical sequelae such as stimulation of adenylyl cyclase.

Tyramine (TYR), β-phenyl-ethylamine (PEA), tryptamine (T) and octopamine (OCT) belong to a class of amines that have low endogenous levels in tissues and thus are referred to as "trace amines" (Usdin and Sandler, 1976). For example, under physiological conditions, brain levels of T in the rat are a thousand-fold lower than those of 5-hydroxytryptamine (5-HT), a major neurotransmitter in vertebrates and invertebrates (Artigas and Gelpi, 1979).

In invertebrates, the role of "trace amines" as neurotransmitters is well established, in particular for OCT and TYR, whose physiological actions have been shown to be mediated directly via their specific receptors. Octopamine, the monohydroxylated analogue of NE, has been studied the most in this respect and is a major neurotransmitter, neurohormone and neuromodulator in many invertebrate species (Axelrod and Saavedra, 1977; David and Coulon, 1985). Because many of the octopamine-mediated responses are connected to adaptation to stressful circumstances, the octopaminergic system has been considered to be the invertebrate equivalent of the vertebrate sympathetic nervous system. Recently, the cloning of the first invertebrate (mollusc) OCT receptor has been reported and it belongs to the family of G protein coupled receptors (GPCR) (Gerhardt et al., 1997). Similarly, TYR which is the precursor of OCT, is abundant in insect brains and its distribution in different tissues does not parallel that of OCT, suggesting that TYR is not merely a precursor in the biosynthetic pathway of OCT (Juorio and Sloley, 1988; Maxwell et al., 1978). In fact, TYR and OCT have opposite effects on adenylate cyclase and glycogenolysis in cockroach fat bodies, TYR being inhibitory and OCT being stimulatory (Downer, 1979). Therefore, in addition to OCT, TYR has also been suggested to play a role as a neurotransmitter in invertebrates (Roeder, 1994). Cloning of an adenylate cyclase inhibitory *Drosophila* TYR receptor, belonging to the family of GPCRs (Saudou et al., 1990) supports this hypothesis.

The evidence for the role of "trace amines" as neurotransmitters in the mammalian system has not been carefully studied. Because of the low concentrations (<100 ng/g) of "trace amines" in mammalian tissues it has sometimes been suggested that they might occur as by-products in the synthesis of other amine neurotransmitters such as the catecholamines or 5-HT. It is now apparent that the turnover of the "trace amines" in most tissues is very rapid, as evidenced by their loss from the brain after intraventricular administration (Wu and Boulton, 1973) and by their accumulation after inhibition of their major catabolic enzyme, monoamine oxidase (MAO) (Axelrod and Saavedra, 1974; Juorio and Durden, 1984; Philips and Boulton, 1979). Due to the fact that these "trace amines" share synthetic and catabolic enzymes with the classical amines, such as 5-HT, norepinephrine (NE) and dopamine (DA), they have also been referred to as "false transmitters" (McGeer et al., 1979). These amines are thus taken up by aminergic neurons, displace monoamines from their storage sites in vesicles, and can themselves and/or other amine neurotransmitters, then be released from neurons by electrical stimulation. Therefore, in mammals, some of the physiological actions of these "trace amines" (sympathomimetic in general, pressor, cardiac stimulant and vasoconstrictor activity) are primarily indirect and are caused by a release of endogenous neurotransmitters (NE, 5-HT, DA).

However, there is a growing body of evidence suggesting that "trace amines" function independently of the classical amine neurotransmitters and mediate some of their effects via their specific receptors. Some of these are described below.

Tyramine is among the first "trace amines" subjected to experimental study. Radiolabeled TYR can be released from rat striatal slices following KCl⁻ depolarization. In reserpine pretreated rats, TYR induced a marked increase in the motor activity, which was not accompanied by a significant decrease in brain catecholamines, ruling out the possibility of indirect receptor stimulation (Stoof et al., 1976). A direct endothelium- and β2-adrenoceptor independent vasorelaxant effect of TYR on rat aortic strips has been reported (Varma and Chemtob, 1993; Varma et al., 1995). Saturable binding sites for [$^3$H]p-tyramine have been reported in rat brain, which may reflect specific TYR receptor sites (Ungar et al., 1977; Vaccaria, 1986; Vaccaria, 1988). Further studies are needed before a clear definition of specific p-tyramine binding site is available. There are no reports of m-tyramine binding sites available as yet.

β-Phenylethylamine which has a chemical structure and pharmacological and behavioral effects that closely resemble those of amphetamine (evokes stereotyped behavior, anorexia and increases locomotor activity) (Wolf and Mosnaim, 1983) and has been described as the body's natural amphetamine. β-Phenylethylamine is synthesized in and released by dopaminergic neurons of the nigrostriatal system (Greenshaw et al., 1986). Saturable, high affinity binding sites have been reported for [$^3$H]β-Phenylethylamine (Hauger et al., 1982). The highest concentration of binding sites was in the hypothalamus, where highest endogenous levels of this amine has been reported (Durden and Philips, 1973). Interestingly, saturable binding sites have also been reported for [$^3$H]amphetamine in membrane preparations from rat brain (Paul et al., 1982), the density of these binding sites being highest in the hypothalamus, as has been seen with PEA binding. These binding sites were shown not to be associated with any previously described neurotransmitter or drug receptor sites and were specific to amphetamine and related PEA derivatives. Furthermore, the relative affinities of a series of PEA derivatives for this binding site were highly correlated to their potencies as anorexic agents. These results suggest the presence of specific receptor sites in the hypothalamus that mediate the anorexic activity of amphetamine and related PEAs.

In addition to TYR and PEA, T has also been shown to produce several physiological effects that are direct and distinct from those mediated by other aminergic neurotransmitters. Tryptamine has been shown to have opposite effects to 5-HT in several Systems studied. For example, unilateral intrahypothalamic injection of T into the preoptic area of the rat causes hyperthermia, whereas 5-HT administered into the same area produces the opposite effect (Cox et al., 1981; Cox et al., 1983). Intravenous administration of T to young rats leads to behavioral stimulation and electrocortical desynchronization, whereas behavioral depression and electrical synchronization was evoked by 5-HT (Dewhurst and Marley, 1965). Also, iontophoretic application of 5-HT and T to cortical neurons has been noted to produce excitatory and inhibitory responses, respectively (Jones, 1982b,c). Injection of deuterated T into the nucleus accumbens of the rat produces sustained locomotor stimulation (Marien et al., 1987), whereas 5-HT injection into the same area produces either only a transient decrease in locomotor activity (Pijnenburg et al., 1976) or no significant effect on locomotion (Gerber et al., 1986; Jackson et al., 1975; Kitada et al., 1983; Plaznik et al., 1985). Tryptamine as well as 5-HT cause contraction of the rat stomach fundus. However, using the non-selective antagonist, phenoxybenzamine (PBZ), Winter and Gessner (1968) showed that the T-induced contractions were more resistant to PBZ blockade than 5-HT-induced contractions. Also, tetrahydro-β-carboline (THBC) antagonizes tryptamine, but not 5-HT-mediated contraction of the isolated rat tail artery (Hicks and Langer, 1983).

The presence of specific, saturable and high affinity [$^3$H]-T binding sites in the rat brain (Altar et al., 1986; Kellar and Cascio, 1982; McCormack et al., 1986; Perry, 1986) and peripheral tissue (Brüning and Rommelspacher, 1984) has been known for a few years. The pharmacological profile of [$^3$H]-T binding is distinct and does not correspond to any known neurotransmitter, transporter or MAO site (Biegon et al., 1982; Fuxe et al., 1983; Leysen et al., 1982; Meibach et al., 1980, 1982; Nakada et al., 1984; Palacios et al., 1983; Perry, 1986, 1988; Slater and Patel, 1983).

The existence of p-octopamine binding sites has been demonstrated in crude membranes obtained from fruitflies but not shown so far in vertebrates (Dudai, 1982; Dudai and Zvi, 1984; Hashemzadeh et al., 1985).

The above findings indicate that in the mammalian system, TYR, PEA and T may function as neurotransmitters in their own rights, and mediate their responses via acting at their distinctive receptors.

"Trace amines" could play a role in depression and psychiatric disorders as well as migraine. Clinical literature supports these indications. MAO inhibitors that are clinically effective for the treatment of depression in the human have been shown to produce a proportionally greater increase in "trace amine" levels compared to 5-HT levels (Boulton, 1976; Juorio, 1976). Based on a functional deficiency of "trace amines", PEA and/or T in particular, have been proposed as a possible etiological factor in depression in humans (Dewhurst, 1968a, b; Dewhurst and Marley, 1965; Sabelli and Monsnaim, 1974).

The urinary output of T has been shown to be disturbed in schizophrenic patients (Brune and Himwhich, 1962; Herkert and Keup, 1969) and in the general psychiatric population (Slingsby and Boulton, 1976). The urinary output of T seems to be positively correlated with increasing severity of psychosis (Brune and Himwhich, 1962; Herkert and Keup, 1969). Depressed patients on the other hand, exhibit decreased urinary output of T (Coppen et al., 1965) and OCT (Sandler et al., 1979).

A role of "trace amines" in migraine is implicated, since certain pharmacological agents in food, in particular TYR, are believed to provoke migraine. There are many reports that attacks of palpitation, hypertension and severe headache (the so called "cheese effect") may follow the consumption of food containing TYR in patients being treated with MAO inhibitors (see Vaughan, 1994 for review). Furthermore, clinical studies have shown that migraine sufferers had lower urinary excretion of TYR sulphate following oral TYR challenge than normal controls. The lower TYR sulfate excretion values among patients with both migraine and depression compared to those of migraine alone or depression alone suggest that comorbid migraine with depression may represent a more severe form of migraine than migraine alone (Merikangas et al., 1995). It is likely that disturbances in the same neurochemical systems, most probably the "trace amines", account for the co-occurrence of migraine and depression.

Urinary levels of PEA, TYR and indole-3-acetic acid (the acid metabolite of T) were found to be decreased in Tourette's Syndrome (TS) patients when compared to values in normal children, indicating a role of these "trace amines" in TS (Baker et al., 1993). Urinary levels of PEA have been shown to be significantly lower in patients with learning disability (LD) and in patients suffering from Attention Deficit Hyperactivity Disorder (ADHD) as compared to age-matched controls, indicating an important role of PEA in pathogenesis of LD and ADHD (Matsuishi and Yamashita, 1999). Tryptamine has also been implicated to play a role in Parkinson's disease, since Parkinsonian patients excrete abnormally high levels of T in their urine (Smith and Kellow, 1969).

Altered "trace amine" metabolism has been observed in non-psychiatric conditions such as pellagra (Sullivan, 1922), Hartnup's disease (Baron et al., 1956), phenylketonuria (Armstrong and Robinson, 1954; Perry, 1962) and thyrotoxicosis (Levine et al., 1962).

Studies in non-human species, rats and mice in particular, add further support for some of the roles of the "trace amines" described above as well as providing various additional physiological roles of "trace amines", as discussed below.

Interestingly, MAO A knock-out mice have elevated brain levels of 5-HT, NE and DA and manifest aggressive behavior similar to human males with a deletion of MAO A. In contrast, MAO B knock-out mice do not exhibit aggression and only levels of PEA are increased. Mice lacking MAO B are resistant to the Parkinsongenic neurotoxin, 1-methyl-4-phenyl-1, 2,3,6-tetra-hydropyridine (MPP$^+$) (Shih et al., 1999), indicating that PEA may provide neuroprotection. Both MAO A and MAO B knock-out mice show increased reactivity to stress suggesting a role of PEA in this condition.

A possible role for T in the protection against renal hypertension afforded by TRP has been suggested (Fregly et al., 1988). A role of OCT in hypertension has been suggested since a hypertensive strain of rats (SHR Kyoto) demonstrates considerably elevated levels of this amine in their brain (David, 1978; 1979). Housing stress has been shown in rats to cause an increase brain and adrenal T levels (Harrison and Christian, 1984) which may be the cause of cardiovascular changes (Bennett and Gardiner, 1978) and hyperactivity (Weinstock et al., 1978) observed in these animals. Therefore, T has been proposed to play a role in is the physiological, behavioral and chemical response to psychological stress.

Tryptamine's actions in the stomach and the presence of [$^3$H]-T binding sites in the stomach suggest a role for T in gastric emptying and control of secretory processes (Brüning and Rommelspacher, 1984; Cohen and Wittenauer, 1985; Winter and Gessner, 1968).

Tryptamine has also been suggested to play a role in hepatic encephalopathy where, due to liver failure, there is a massive increase in brain TRP (precursor of T) leading to a series of CNS symptoms including altered sleep patterns and personality changes and eventually resulting in coma (Sourkes, 1978).

Tryptamine has been shown to cause release from isolated rat lungs of a spasmogen, resembling slow reacting substance of anaphylaxis that has prostaglandin E-like activity (Bakhle and Smith, 1977). Therefore, T may have a function in asthma.

In summary, "trace amines" may act as neurotransmitters and neuromodulators. These amines may act via their specific receptor sites to elicit some of their physiological actions. It is not yet clear what the role of these "trace amines" is in pathological conditions such as mental and physical stress, hepatic dysfunction, hypertension and electrolyte imbalance. A primary role of "trace amines" in the etiology of mental or neurological diseases is still hypothetical. "Trace amine"-mediated effects indicate that receptors for these amines are attractive as targets for therapeutic intervention for several disorders and would be useful to develop drugs with higher specificity and fewer side effects for a wide variety of diseases.

SUMMARY OF THE INVENTION

This invention provides an isolated nucleic acid encoding a mammalian SNORF33 receptor.

This invention further provides a purified mammalian SNORF33 receptor protein.

This invention also provides a vector comprising a nucleic acid in accordance with this invention.

This invention still further provides a cell comprising a vector in accordance with this invention.

This invention additionally provides a membrane preparation isolated from a cell in accordance with this invention.

Furthermore, this invention provides a nucleic acid probe comprising at least 15 nucleotides, which probe specifically hybridizes with a nucleic acid encoding a mammalian SNORF33 receptor, wherein the probe has a sequence complementary to a unique sequence present within one of the two strands of the nucleic acid encoding the mammalian SNORF33 receptor contained in plasmid pcDNA3.1-hSNORF33-f (ATCC Patent Depository No. PTA-398), plasmid pcDNA3.1-rSNORF33-f (ATCC Patent Depository No. PTA-102), plasmid pEXJ-hSNORF33-f (ATCC Patent Depository No. PTA-570), or plasmid pEXJ-mSNORF33-f (ATCC Patent Depository No. PTA-1665).

This invention further provides a nucleic acid probe comprising at least 15 nucleotides, which probe specifically hybridizes with a nucleic acid encoding a mammalian SNORF33 receptor, wherein the probe has a sequence complementary to a unique sequence present within (a) the nucleic acid sequence shown in FIGS. 5A-5B (SEQ ID NO: 5) or (b) the reverse complement thereof.

This invention provides an antisense oligonucleotide having a sequence capable of specifically hybridizing to RNA encoding a mammalian SNORF33 receptor, so as to prevent translation of such RNA.

This invention further provides an antisense oligonucleotide having a sequence capable of specifically hybridizing to genomic DNA encoding a mammalian SNORF33 receptor, so as to prevent transcription of such genomic DNA.

This invention also provides an antibody capable of binding to a mammalian SNORF33 receptor encoded by a nucleic acid in accordance with this invention.

Moreover, this invention provides an agent capable of competitively inhibiting the binding of an antibody in accordance with this invention to a mammalian SNORF33 receptor.

This invention yet further provides a pharmaceutical composition comprising (a) an amount of an oligonucleotide in accordance with this invention capable of passing through a cell membrane and effective to reduce expression of a mammalian SNORF33 receptor and (b) a pharmaceutically acceptable carrier capable of passing through the cell membrane.

This invention also provides a pharmaceutical composition which comprises an amount of an antibody in accordance with this invention effective to block binding of a ligand to a human SNORF33 receptor and a pharmaceutically acceptable carrier.

This invention further provides a transgenic, nonhuman mammal expressing DNA encoding a mammalian SNORF33 receptor in accordance with this invention.

This invention still further provides a transgenic, nonhuman mammal comprising a homologous recombination knockout of a native mammalian SNORF33 receptor.

This invention further provides a transgenic, nonhuman mammal whose genome comprises antisense DNA complementary to DNA encoding a mammalian SNORF33 receptor in accordance with this invention so placed within such genome as to be transcribed into antisense mRNA which is complementary to and hybridizes with mRNA encoding the mammalian SNORF33 receptor so as to reduce translation of such mRNA and expression of such receptor.

This invention provides a process for identifying a chemical compound which specifically binds to a mammalian SNORF33 receptor which comprises contacting cells containing DNA encoding, and expressing on their cell surface, the mammalian SNORF33 receptor, wherein such cells do not normally express the mammalian SNORF33 receptor, with the compound under conditions suitable for binding, and detecting specific binding of the chemical compound to the mammalian SNORF33 receptor.

This invention further provides a process for identifying a chemical compound which specifically binds to a mammalian SNORF33 receptor which comprises contacting a membrane preparation from cells containing DNA encoding, and expressing on their cell surface, the mammalian SNORF33 receptor, wherein such cells do not normally express the mammalian SNORF33 receptor, with the compound under conditions suitable for binding, and detecting specific binding of the chemical compound to the mammalian SNORF33 receptor.

This invention still further provides a process involving competitive binding for identifying a chemical compound which specifically binds to a mammalian SNORF33 receptor which comprises separately contacting cells expressing on their cell surface the mammalian SNORF33 receptor, wherein such cells do not normally express the mammalian SNORF33 receptor, with both the chemical compound and a second chemical compound known to bind to the receptor, and with only the second chemical compound, under conditions suitable for binding of such compounds to the receptor, and detecting specific binding of the chemical compound to the mammalian SNORF33 receptor, a decrease in the binding of the second chemical compound to the mammalian SNORF33 receptor in the presence of the chemical compound being tested indicating that such chemical compound binds to the mammalian SNORF33 receptor.

This invention further provides a process involving competitive binding for identifying a chemical compound which specifically binds to a mammalian SNORF33 receptor which comprises separately contacting a membrane preparation from cells expressing on their cell surface the mammalian SNORF33 receptor, wherein such cells do not normally express the mammalian SNORF33 receptor, with both the chemical compound and a second chemical compound known to bind to the receptor, and with only the second chemical compound, under conditions suitable for binding of such compounds to the receptor, and detecting specific binding of the chemical compound to the mammalian SNORF33 receptor, a decrease in the binding of the second chemical compound to the mammalian SNORF33 receptor in the presence of the chemical compound being tested indicating that such chemical compound binds to the mammalian SNORF33 receptor.

This invention further provides a compound identified by one of the processes of this invention.

This invention provides a method of screening a plurality of chemical compounds not known to bind to a mammalian SNORF33 receptor to identify a compound which specifically binds to the mammalian SNORF33 receptor, which comprises (a) contacting cells transfected with, and expressing, DNA encoding the mammalian SNORF33 receptor with a compound known to bind specifically to the mammalian SNORF33 receptor; (b) contacting the cells of step (a) with the plurality of compounds not known to bind specifically to the mammalian SNORF33 receptor, under conditions permitting binding of compounds known to bind to the mammalian SNORF33 receptor; (c) determining whether the binding of the compound known to bind to the mammalian SNORF33 receptor is reduced in the presence of the plurality of compounds, relative to the binding of the compound in the absence of the plurality of compounds; and if so (d) separately determining the binding to the mammalian SNORF33 receptor of each compound included in the plurality of compounds, so as to thereby identify any compound included therein which specifically binds to the mammalian SNORF33 receptor.

This invention further provides a method of screening a plurality of chemical compounds not known to bind to a mammalian SNORF33 receptor to identify a compound which specifically binds to the mammalian SNORF33 receptor, which comprises (a) contacting a membrane preparation from cells transfected with, and expressing, DNA encoding the mammalian SNORF33 receptor with the plurality of compounds not known to bind specifically to the mammalian SNORF33 receptor under conditions permitting binding of compounds known to bind to the mammalian SNORF33 receptor; (b) determining whether the binding of a compound known to bind to the mammalian SNORF33 receptor is reduced in the presence of the plurality of compounds, relative to the binding of the compound in the absence of the plurality of compounds; and if so (c) separately determining the binding to the mammalian SNORF33 receptor of each compound included in the plurality of compounds, so as to thereby identify any compound included therein which specifically binds to the mammalian SNORF33 receptor.

This invention also provides a method of detecting expression of a mammalian SNORF33 receptor by detecting the presence of mRNA coding for the mammalian SNORF33 receptor which comprises obtaining total mRNA from the cell and contacting the mRNA so obtained with a nucleic acid probe according to this invention under hybridizing conditions, detecting the presence of mRNA hybridized to the probe, and thereby detecting the expression of the mammalian SNORF33 receptor by the cell.

This invention further provides a method of detecting the presence of a mammalian SNORF33 receptor on the surface of a cell which comprises contacting the cell with an antibody according to this invention under conditions permitting binding of the antibody to the receptor, detecting the presence of the antibody bound to the cell, and thereby detecting the presence of the mammalian SNORF33 receptor on the surface of the cell.

This invention still further provides a method of determining the physiological effects of varying levels of activity of mammalian SNORF33 receptors which comprises producing a transgenic, nonhuman mammal in accordance with this invention whose levels of mammalian SNORF33 receptor activity are varied by use of an inducible promoter which regulates mammalian SNORF33 receptor expression.

This invention additionally provides a method of determining the physiological effects of varying levels of activity of mammalian SNORF33 receptors which comprises producing a panel of transgenic, nonhuman mammals in accordance with this invention each expressing a different amount of mammalian SNORF33 receptor.

Moreover, this invention provides a method for identifying an antagonist capable of alleviating an abnormality wherein the abnormality is alleviated by decreasing the activity of a mammalian SNORF33 receptor comprising administering a compound to a transgenic, nonhuman mammal according to this invention, and determining whether the compound alleviates any physiological and/or behavioral abnormality displayed by the transgenic, nonhuman mammal as a result of overactivity of a mammalian SNORF33 receptor, the alleviation of such an abnormality identifying the compound as an antagonist.

This invention also provides an antagonist identified by the preceding method.

This invention further provides a composition, e.g. a pharmaceutical composition, comprising an antagonist according to this invention and a carrier, e.g. a pharmaceutically acceptable carrier.

This invention additionally provides a method of treating an abnormality in a subject wherein the abnormality is alleviated by decreasing the activity of a mammalian SNORF33 receptor which comprises administering to the subject an effective amount of the pharmaceutical composition according to this invention so as to thereby treat the abnormality.

In addition, this invention provides a method for identifying an agonist capable of alleviating an abnormality in a subject wherein the abnormality is alleviated by increasing the activity of a mammalian SNORF33 receptor comprising administering a compound to a transgenic, nonhuman mammal according to this invention, and determining whether the compound alleviates any physiological and/or behavioral abnormality displayed by the transgenic, nonhuman mammal, the alleviation of such an abnormality identifying the compound as an agonist.

This invention further provides an agonist identified by the preceding method.

This invention still further provides a composition, e.g. a pharmaceutical composition, comprising an agonist according to this invention and a carrier, e.g. a pharmaceutically acceptable carrier.

Moreover, this invention provides a method of treating an abnormality in a subject wherein the abnormality is alleviated by increasing the activity of a mammalian SNORF33 receptor which comprises administering to the subject an effective amount of the pharmaceutical composition according to this invention so as to thereby treat the abnormality.

Yet further, this invention provides a method for diagnosing a predisposition to a disorder associated with the activity of a specific mammalian allele which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a mammalian SNORF33 receptor and labeled with a detectable marker; (e) detecting labeled bands which have hybridized to the DNA encoding a mammalian SNORF33 receptor to create a unique band pattern specific to the DNA of subjects suffering from the disorder; (f) repeating steps (a)-(e) with DNA obtained for diagnosis from subjects not yet suffering from the disorder; and (g) comparing the unique band pattern specific to the DNA of subjects suffering from the disorder from step (e) with the band pattern from step (f) for subjects not yet suffering from the disorder so as to determine whether the patterns are the same or different and thereby diagnose predisposition to the disorder if the patterns are the same.

This invention also provides a method of preparing a purified mammalian SNORF33 receptor according to the invention which comprises: (a) culturing cells which express the mammalian SNORF33 receptor; (b) recovering the mammalian SNORF33 receptor from the cells; and (c) purifying the mammalian SNORF33 receptor so recovered.

This invention further provides a method of preparing the purified mammalian SNORF33 receptor according to the invention which comprises: (a) inserting a nucleic acid encoding the mammalian SNORF33 receptor into a suitable expression vector; (b) introducing the resulting vector into a suitable host cell; (c) placing the resulting host cell in suitable conditions permitting the production of the mammalian SNORF33 receptor; (d) recovering the mammalian SNORF33 receptor so produced; and optionally (e) isolating and/or purifying the mammalian SNORF33 receptor so recovered.

Furthermore, this invention provides a process for determining whether a chemical compound is a mammalian SNORF33 receptor agonist which comprises contacting cells transfected with and expressing DNA encoding the mammalian SNORF33 receptor with the compound under conditions permitting the activation of the mammalian SNORF33 receptor, and detecting any increase in mammalian SNORF33 receptor activity, so as to thereby determine whether the compound is a mammalian SNORF33 receptor agonist.

This invention also provides a process for determining whether a chemical compound is a mammalian SNORF33 receptor antagonist which comprises contacting cells transfected with and expressing DNA encoding the mammalian SNORF33 receptor with the compound in the presence of a known mammalian SNORF33 receptor agonist, under conditions permitting the activation of the mammalian SNORF33 receptor, and detecting any decrease in mammalian SNORF33 receptor activity, so as to thereby determine whether the compound is a mammalian SNORF33 receptor antagonist.

This invention still further provides a composition, for example a pharmaceutical composition, which comprises an amount of a mammalian SNORF33 receptor agonist determined by a process according to this invention effective to increase activity of a mammalian SNORF33 receptor and a carrier, for example, a pharmaceutically acceptable carrier. In one embodiment, the mammalian SNORF33 receptor agonist is not previously known.

Also, this invention provides a composition, for example a pharmaceutical composition, which comprises an amount of a mammalian SNORF33 receptor antagonist determined by a process according to this invention effective to reduce activity of a mammalian SNORF33 receptor and a carrier, for example, a pharmaceutically acceptable carrier.

This invention moreover provides a process for determining whether a chemical compound specifically binds to and activates a mammalian SNORF33 receptor, which comprises contacting cells producing a second messenger response and expressing on their cell surface the mammalian SNORF33 receptor, wherein such cells do not normally express the mammalian SNORF33 receptor, with the chemical compound under conditions suitable for activation of the mammalian SNORF33 receptor, and measuring the second messenger response in the presence and in the absence of the chemical compound, a change, e.g. an increase, in the second messenger response in the presence of the chemical compound indicating that the compound activates the mammalian SNORF33 receptor.

This invention still further provides a process for determining whether a chemical compound specifically binds to and inhibits activation of a mammalian SNORF33 receptor, which comprises separately contacting cells producing a second messenger response and expressing on their cell surface the mammalian SNORF33 receptor, wherein such cells do not normally express the mammalian SNORF33 receptor, with both the chemical compound and a second chemical compound known to activate the mammalian SNORF33 receptor, and with only the second chemical compound, under conditions suitable for activation of the mammalian SNORF33 receptor, and measuring the second messenger response in the presence of only the second chemical compound and in the presence of both the second chemical compound and the chemical compound, a smaller change, e.g. increase, in the second messenger response in the presence of both the chemical compound and the second chemical compound than in the presence of only the second chemical compound indicating that the chemical compound inhibits activation of the mammalian SNORF33 receptor.

Further, this invention provides a compound determined by a process according to the invention and a composition, for example, a pharmaceutical composition, which comprises an amount of a mammalian SNORF33 receptor agonist determined to be such by a process according to the invention, effective to increase activity of the mammalian SNORF33 receptor and a carrier, for example, a pharmaceutically acceptable carrier.

This invention also provides a composition, for example, a pharmaceutical composition, which comprises an amount of a mammalian SNORF33 receptor antagonist determined to be such by a process according to the invention, effective to reduce activity of the mammalian SNORF33 receptor and a carrier, for example, a pharmaceutically acceptable carrier.

This invention yet further provides a method of screening a plurality of chemical compounds not known to activate a mammalian SNORF33 receptor to identify a compound which activates the mammalian SNORF33 receptor which comprises: (a) contacting cells transfected with and expressing the mammalian SNORF33 receptor with the plurality of compounds not known to activate the mammalian SNORF33 receptor, under conditions permitting activation of the mammalian SNORF33 receptor; (b) determining whether the activity of the mammalian SNORF33 receptor is increased in the presence of one or more of the compounds; and if so (c) separately determining whether the activation of the mammalian SNORF33 receptor is increased by any compound included in the plurality of compounds, so as to thereby identify each compound which activates the mammalian SNORF33 receptor.

This invention provides a method of screening a plurality of chemical compounds not known to inhibit the activation of a mammalian SNORF33 receptor to identify a compound which inhibits the activation of the mammalian SNORF33 receptor, which comprises: (a) contacting cells transfected with and expressing the mammalian SNORF33 receptor with the plurality of compounds in the presence of a known mammalian SNORF33 receptor agonist, under conditions permitting activation of the mammalian SNORF33 receptor; (b) determining whether the extent or amount of activation of the mammalian SNORF33 receptor is reduced in the presence of one or more of the compounds, relative to the extent or amount of activation of the mammalian SNORF33 receptor in the absence of such one or more compounds; and if so (c) separately determining whether each such compound inhibits activation of the mammalian SNORF33 receptor for each compound included in the plurality of compounds, so as to thereby identify any compound included in such plurality of compounds which inhibits the activation of the mammalian SNORF33 receptor.

This invention also provides a composition, for example a pharmaceutical composition, comprising a compound identified by a method according to this invention in an amount effective to increase mammalian SNORF33 receptor activity and a carrier, for example, a pharmaceutically acceptable carrier.

This invention still further provides a composition, for example a pharmaceutical composition, comprising a compound identified by a method according to this invention in an amount effective to decrease mammalian SNORF33 receptor activity and a carrier, for example a pharmaceutically acceptable carrier.

Furthermore, this invention provides a method of treating an abnormality in a subject wherein the abnormality is alleviated by increasing the activity of a mammalian SNORF33 receptor which comprises administering to the subject a compound which is a mammalian SNORF33 receptor agonist in an amount effective to treat the abnormality.

This invention additionally provides a method of treating an abnormality in a subject wherein the abnormality is alleviated by decreasing the activity of a mammalian SNORF33 receptor which comprises administering to the subject a compound which is a mammalian SNORF33 receptor antagonist in an amount effective to treat the abnormality.

This invention also provides a process for making a composition of matter which specifically binds to a mammalian SNORF33 receptor which comprises identifying a chemical compound using a process in accordance with this invention and then synthesizing the chemical compound or a novel structural and functional analog or homolog thereof.

This invention further provides a process for preparing a composition, for example, a pharmaceutical composition which comprises admixing a carrier, for example, a pharmaceutically acceptable carrier, and a pharmaceutically effective amount of a chemical compound identified by a process of in accordance with this invention or a novel structural and functional analog or homolog thereof.

BRIEF DESCRIPTION OF THE FIGURES

FIG. 1
Nucleotide sequence including part of the sequence encoding a human SNORF33 receptor (SEQ ID NO: 1)

FIG. 2
Deduced amino acid sequence (SEQ ID NO: 2) of the human SNORF33 receptor encoded by the nucleotide sequence shown in FIG. 1 (SEQ ID NO: 1).

FIGS. 3A-3B
Nucleotide sequence including sequence encoding a rat SNORF33 receptor (SEQ ID NO: 3). Putative open reading frames including the shortest open reading frame are indicated by underlining one start (ATG) codon (at positions 53-55) and the stop codon (at positions 1049-1051). In addition, partial 5' and 3' untranslated sequences are shown.

FIGS. 4A-4B
Deduced amino acid sequence (SEQ ID NO: 4) of the rat SNORF33 receptor encoded by the longest open reading frame indicated in the nucleotide sequence shown in FIGS. 3A-3B (SEQ ID NO: 3). The seven putative transmembrane (TM) regions are underlined.

FIGS. 5A-5B
Nucleotide sequence including sequence encoding a human SNORF33 receptor (SEQ ID NO: 5). Putative open reading frames including the shortest open reading frame are indicated by underlining two start (ATG) codons (at positions 7-9 and 10-12) and the stop codon (at positions 1024-1026). In addition, partial 5' and 3' untranslated sequences are shown.

FIGS. 6A-6B
Deduced amino acid sequence (SEQ ID NO: 6) of the human SNORF33 receptor encoded by the longest open reading frame indicated in the nucleotide sequence shown in FIGS. 5A-5B (SEQ ID NO: 5). The seven putative transmembrane (TM) regions are underlined.

FIGS. 7A-7B
Alignment of the rat and human SNORF33 amino acid sequences. Conserved residues are indicated by a vertical line and similar residues are indicated by single or double dots. Gaps in the alignment are indicated by dots in the sequence.

FIG. 8
Basal cAMP levels in COS-7 cells transfected with DNA vector (Mock)- and rSNORF33 DNA. The data are presented as mean±S.E.M. Number of experiments=6-7.

(FIG. 11B) Plot of concentration-response data for tyramine, tryptamine, octopamine and 5-HT multiple batches of oocytes expressing SNORF33 and CFTR. n=4-7 oocytes for each data point. Curves were fit using the Hill equation of the form I=1 (1+(EC$_{50}$/[Agonist])$^n$).

Figure 9:
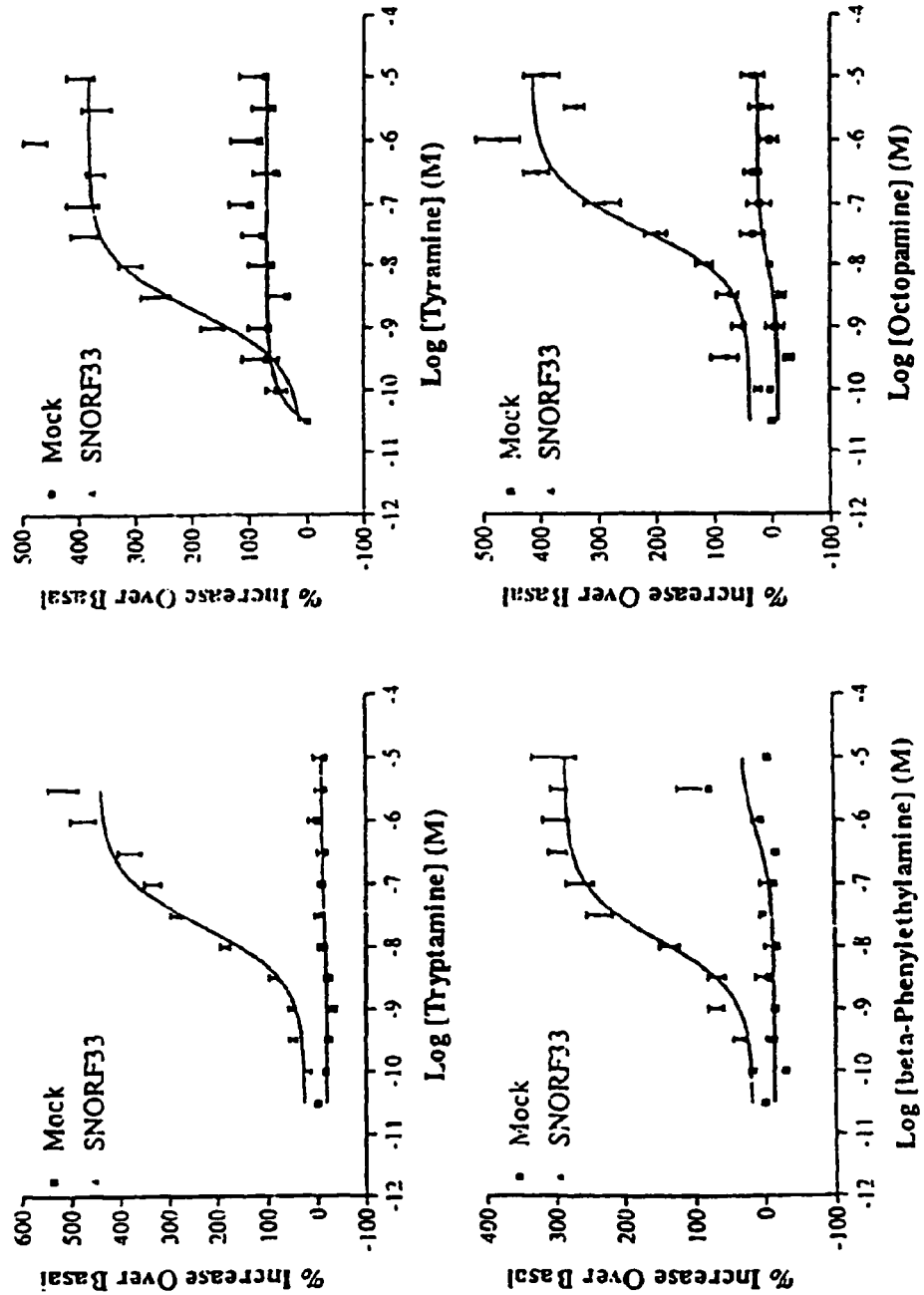
FIG. 9
Stimulation of intracellular cAMP release by agonists in DNA vector (Mock)- and rSNORF33-transfected COS-7 cells. The data are presented as mean±S.E.M. Number of experiments=3-8.

Antagonist profile of a variety of compounds tested at single doses (100 µM except where noted) for their ability to inhibit responses to an EC$_{80}$ concentration of tyramine (100 nM) in oocytes expressing SNORF33 and CFTR. Responses in the presence of test compound were normalized to the current stimulated by an application of tyramine applied in the absence of test compound.

FIG. 13

Saturation binding of [$^3$H]-TYR. COS-7 cells were transiently-transfected with rSNORF33 and membranes were prepared as described in Materials and Methods. Membranes (40-70 µg protein) were incubated at 4° C. with increasing concentrations of [$^3$H]-TYR (0.1 nM-70 nM) for 30 minutes. Non-specific binding was determined in the presence of 10 µM TYR and represented <10% of total binding. Results are representative of two independent experiments with average Kd=12.5 nM and Bmax=1400 fmol/mg protein.

FIG. 14

Representative curves for various "trace amines" displacing [$^3$H]-TYR binding to rSNORF33. The indicated compounds were evaluated in competition binding assays on membranes from rSNORF33 using [$^3$H]-TYR (7-15 nM) as the radioligand. Non-specific binding was determined in the presence of 10 µM TYR and data were fit to non-linear curves using GraphPad Prism. Ki values were determined using the Cheng-Prussoff correction.

FIG. 15

Specific binding of [$^3$H]-T to rSNORF33- and mock-transfected COS-7 cell membranes. Binding assay using 20 nM [$^3$H]-T was performed according to the Methods. The data are presented as mean+S.E.M. of quadruplicate determinations.

FIG. 16

Electrophysiological response of an oocyte expressing hSNORF33 and CFTR. Bar indicates the application of 100 µM tyramine. Break in the trace represents a 5 second gap in the recording. Oocyte was voltage clamped to −80 mV.

FIG. 17

Nucleotide sequence including part of the sequence encoding a mouse SNORF33 receptor (SEQ ID NO: 30).

FIG. 18

Deduced partial amino acid sequence (SEQ ID NO: 31) of the mouse SNORF33 receptor encoded by the nucleotide sequence shown in FIG. 17 (SEQ ID NO: 30). Putative transmembrane (TM) regions are underlined.

FIGS. 19A-19B

Nucleotide sequence including sequence encoding a mouse SNORF33 receptor (SEQ ID NO: 36). Putative open reading frames including the shortest open reading frame are indicated by underlining one start (ATG) codon (at positions 8-10) and the stop codon (at positions 1004-1006). In addition, partial 5' and 3' untranslated sequences are shown.

FIGS. 20A-20B

Deduced amino acid sequence (SEQ ID NO: 37) of the mouse SNORF33 receptor encoded by the longest open reading frame indicated in the nucleotide sequence shown in FIGS. 19A-19B (SEQ ID NO: 36). The seven putative transmembrane (TM) regions are underlined.

FIG. 21

Alignment of the deduced amino acid sequences of the rat, mouse and human SNORF33 receptors. Residues in capital letters are conserved in all three species, and dashes in the consensus illustrate non-conserved residues.

DETAILED DESCRIPTION OF THE INVENTION

This invention provides a recombinant nucleic acid comprising a nucleic acid encoding a mammalian SNORF33 receptor, wherein the mammalian receptor-encoding nucleic acid hybridizes under high stringency conditions to (a) a nucleic acid encoding a human SNORF33 receptor and having a sequence comprising the sequence of the human SNORF33 nucleic acid contained in plasmid pcDNA3.1-hS-NORF33-p (ATCC Patent Depository No. PTA-101) or (b) a nucleic acid encoding a rat SNORF33 receptor and having a sequence identical to the sequence of the rat SNORF33 receptor-encoding nucleic acid contained in plasmid pcDNA3.1-rSNORF33-f (ATCC Patent Depository No. PTA-102).

This invention further provides a recombinant nucleic acid comprising a nucleic acid encoding a human SNORF33 receptor, wherein the human SNORF33 receptor comprises an amino acid sequence identical to the sequence encoded by the nucleic acid shown in FIG. 1 (SEQ ID NO: 1).

This invention also provides a recombinant nucleic acid comprising a nucleic acid encoding a rat SNORF33 receptor, wherein the rat SNORF33 receptor comprises an amino acid sequence identical to the sequence of the rat SNORF33 receptor encoded by the shortest open reading frame indicated in FIGS. 3A-3B (SEQ ID NO: 3).

The plasmid pcDNA3.1-hSNORF33-p and plasmid pcDNA3.1-rSNORF33-f were both deposited on May 21, 1999, with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure and were accorded ATCC Patent Depository Nos. PTA-101 and PTA-102, respectively.

This invention also provides a recombinant nucleic acid comprising a nucleic acid encoding a mammalian SNORF33 receptor, wherein the mammalian receptor-encoding nucleic acid hybridizes under high stringency conditions to (a) a nucleic acid encoding a human SNORF33 receptor and having a sequence comprising the sequence of the human SNORF33 nucleic acid contained in plasmid pcDNA3.1-hS-NORF33-f (ATCC Patent Depository No. PTA-398) or plasmid pEXJ-hSNORF33-f (ATCC Patent Depository No. PTA-570).

This invention further provides a recombinant nucleic acid comprising a nucleic acid encoding a human SNORF33 receptor, wherein the human SNORF33 receptor comprises an amino acid sequence identical to the sequence encoded by the nucleic acid shown in FIGS. 5A-5B (SEQ ID NO: 5).

The plasmid pcDNA3.1-hSNORF33-f was deposited on Jul. 21, 1999, with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure and was accorded ATCC Patent Depository No. PTA-398.

The plasmid pEXJ-hSNORF33-f was deposited on Aug. 24, 1999, with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure and was accorded ATCC Patent Depository No. PTA-570.

This invention also provides a recombinant nucleic acid comprising a nucleic acid encoding a mammalian SNORF33 receptor, wherein the mammalian receptor-encoding nucleic acid hybridizes under high stringency conditions to (a) a nucleic acid encoding a mouse SNORF33 receptor and having a sequence comprising the sequence of the mouse SNORF33 nucleic acid contained in plasmid pEXJ-mS-NORF33-f (ATCC Patent Depository No. PTA-1665).

This invention further provides a recombinant nucleic acid comprising a nucleic acid encoding a mouse SNORF33 receptor, wherein the mouse SNORF33 receptor comprises an amino acid sequence identical to the sequence encoded by the nucleic acid shown in FIGS. 19A-19B (SEQ ID NO: 36).

The plasmid pEXJ-mSNORF33-f was deposited on Apr. 7, 2000, with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure and was accorded ATCC Patent Depository No. PTA-1665.

Hybridization methods are well known to those of skill in the art. For purposes of this invention, hybridization under high stringency conditions means hybridization performed at 40° C. in a hybridization buffer containing 50% formamide, 5× SSC, 7 mM Tris, 1× Denhardt's, 25 µg/ml salmon sperm DNA; wash at 50° C. in 0.1× SSC, 0.1% SDS.

Throughout this application, the following standard abbreviations are used to indicate specific nucleotide bases:

| | |
|---|---|
| A = | adenine |
| G = | guanine |
| C = | cytosine |
| T = | thymine |
| M = | adenine or cytosine |
| R = | adenine or guanine |
| W = | adenine or thymine |
| S = | cytosine or guanine |
| Y = | cytosine or thymine |
| K = | guanine or thymine |
| V = | adenine, cytosine, or guanine (not thymine) |
| H = | adenine, cytosine, or thymine (not cytosine) |
| B = | cytosine, guanine, or thymine (not adenine) |
| N = | adenine, cytosine, guanine, or thymine (or other modified base such as inosine) |
| I = | inosine |

Furthermore, the term "agonist" is used throughout this application to indicate any peptide or non-peptidyl compound which increases the activity of any of the polypeptides of the subject invention. The term "antagonist" is used throughout this application to indicate any peptide or non-peptidyl compound which decreases the activity of any of the polypeptides of the subject invention.

Furthermore, as used herein, the phrase "pharmaceutically acceptable carrier" means any of the standard pharmaceutically acceptable carriers. Examples include, but are not limited to, phosphate buffered saline, physiological saline, water, and emulsions, such as oil/water emulsions.

It is possible that the mammalian SNORF33 receptor gene contains introns and furthermore, the possibility exists that additional introns could exist in coding or non-coding regions. In addition, spliced form(s) of mRNA may encode additional amino acids either upstream of the currently defined starting methionine or within the coding region. Further, the existence and use of alternative exons is possible, whereby the mRNA may encode different amino acids within the region comprising the exon. In addition, single amino acid substitutions may arise via the mechanism of RNA editing such that the amino acid sequence of the expressed protein is different than that encoded by the original gene (Burns, et al., 1996; Chu, et al., 1996). Such variants may exhibit pharmacologic properties differing from the polypeptide encoded by the original gene.

This invention provides splice variants of the mammalian SNORF33 receptors disclosed herein. This invention further provides for alternate translation initiation sites and alternately spliced or edited variants of nucleic acids encoding the SNORF33 receptors of this invention.

This invention also contemplates recombinant nucleic acids which comprise nucleic acids encoding naturally occurring allelic variants of the SNORF33 receptors disclosed herein.

Figure 2:
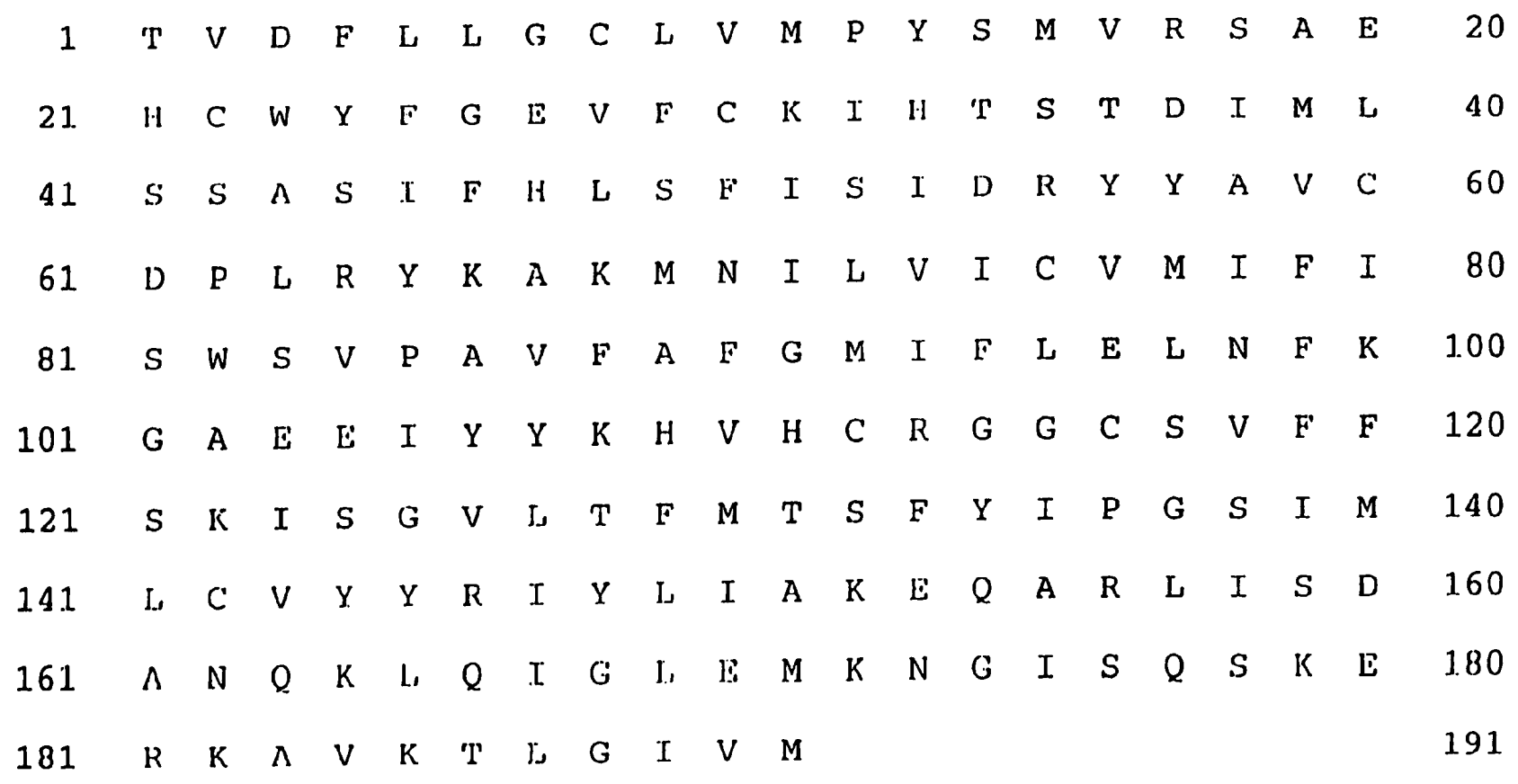

The nucleic acids of the subject invention also include nucleic acid analogs of the human SNORF33 receptor genes, wherein the human SNORF33 receptor gene comprises the nucleic acid sequence shown in FIG. 1 or contained in plasmid pcDNA3.1-hSNORF33-p (ATCC Patent Depository No. PTA-101). Nucleic acid analogs of the human SNORF33 receptor genes differ from the human SNORF33 receptor genes described herein in terms of the identity or location of one or more nucleic acid bases (deletion analogs containing less than all of the nucleic acid bases shown in FIG. 1 or contained in plasmid pcDNA3.1-hSNORF33-p (ATCC Patent Depository No. PTA-101), substitution analogs wherein one or more nucleic acid bases shown in FIG. 1 or contained in plasmid pcDNA3.1-hSNORF33-p (ATCC Patent Depository No. PTA-101), are replaced by other nucleic acid bases, and addition analogs, wherein one or more nucleic acid bases are added to a terminal or medial portion of the nucleic acid sequence) and which encode proteins which share some or all of the properties of the proteins encoded by the nucleic acid sequences shown in FIG. 1 or contained in plasmid pcDNA3.1-hSNORF33-p (ATCC Patent Depository No. PTA-101). In one embodiment of the present invention, the nucleic acid analog encodes a protein which has an amino acid sequence identical to that shown in FIG. 2 or encoded by the nucleic acid sequence contained in plasmid pcDNA3.1-hSNORF33-p (ATCC Patent Depository No. PTA-101). In another embodiment, the nucleic acid analog encodes a protein having an amino acid sequence which differs from the amino acid sequences shown in FIG. 2 or encoded by the nucleic acid contained in plasmid pcDNA3.1-hSNORF33-p (ATCC Patent Depository No. PTA-101). In a further embodiment, the protein encoded by the nucleic acid analog has a function which is the same as the function of the receptor proteins having the amino acid sequence shown in FIG. 2. In another embodiment, the function of the protein encoded by the nucleic acid analog differs from the function of the receptor protein having the amino acid sequence shown in FIG. 2. In another embodiment, the variation in the nucleic acid sequence occurs within the transmembrane (TM) region of the protein. In a further embodiment, the variation in the nucleic acid sequence occurs outside of the TM region.

Figure 4A:
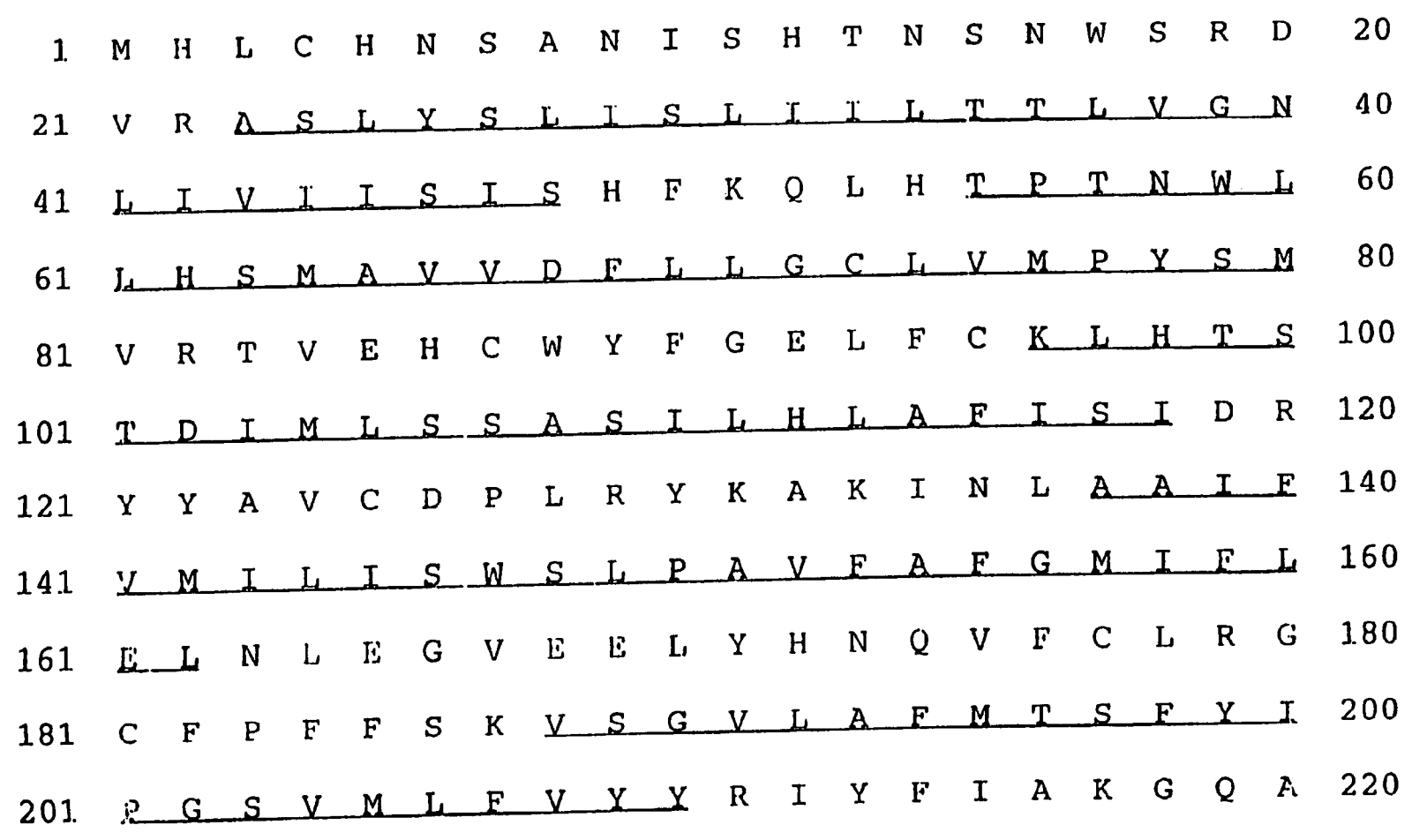
Figure 4B:
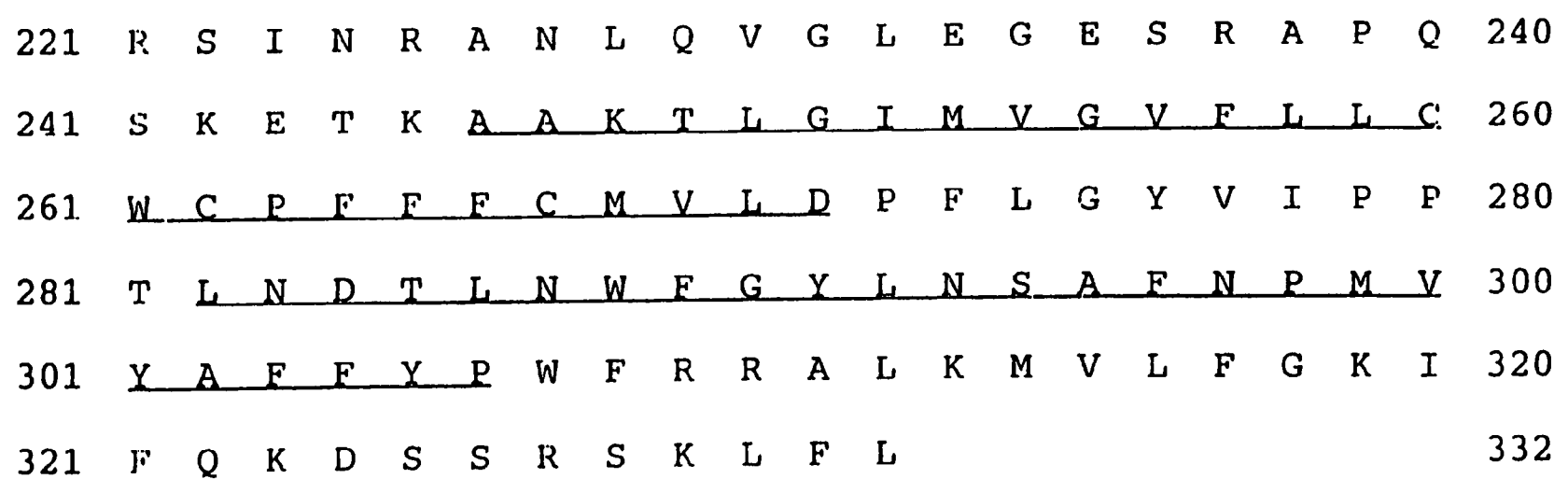

The nucleic acids of the subject invention also include nucleic acid analogs of the rat SNORF33 receptor genes, wherein the rat SNORF33 receptor gene comprises the nucleic acid sequence shown in FIGS. 3A-3B or contained in plasmid pcDNA3.1-rSNORF33-f (ATCC Patent Depository No. PTA-102). Nucleic acid analogs of the rat SNORF33 receptor genes differ from the rat SNORF33 receptor genes described herein in terms of the identity or location of one or more nucleic acid bases (deletion analogs containing less than all of the nucleic acid bases shown in FIGS. 3A-3B or contained in plasmid pcDNA3.1-rSNORF33-f (ATCC Patent Depository No. PTA-102) substitution analogs wherein one or more nucleic acid bases shown in FIGS. 3A-3B or contained in plasmid pcDNA3.1-rSNORF33-f (ATCC Patent Depository No. PTA-102), are replaced by other nucleic acid bases, and addition analogs, wherein one or more nucleic acid bases are added to a terminal or medial portion of the nucleic acid sequence) and which encode proteins which share some or all of the properties of the proteins encoded by the nucleic acid sequences shown in FIGS. 3A-3B or contained in plasmid pcDNA3.1-rSNORF33-f (ATCC Patent Depository No. PTA-102). In one embodiment of the present invention, the nucleic acid analog encodes a protein which has an amino acid sequence identical to that shown in FIGS. 4A-4B or encoded by the nucleic acid sequence contained in plasmid pcDNA3.1-rSNORF33-f (ATCC Patent Depository No. PTA-102). In another embodiment, the nucleic acid analog encodes a protein having an amino acid sequence which differs from the amino acid sequences shown in FIGS. 4A-4B or encoded by the nucleic acid contained in plasmid pcDNA3.1-rSNORF33-f (ATCC Patent Depository No. PTA-102). In a further embodiment, the protein encoded by the nucleic acid analog has a function which is the same as the function of the receptor proteins having the amino acid sequence shown in FIGS. 4A-4B. In another embodiment, the function of the protein encoded by the nucleic acid analog differs from the function of the receptor protein having the amino acid sequence shown in FIGS. 4A-4B. In another embodiment, the variation in the nucleic acid sequence occurs within the transmembrane (TM) region of the protein. In a further embodiment, the variation in the nucleic acid sequence occurs outside of the TM region.

The nucleic acids of the subject invention also include nucleic acid analogs of the human SNORF33 receptor genes, wherein the human SNORF33 receptor gene comprises the nucleic acid sequence shown in FIGS. 5A-5B or contained in plasmid pcDNA3.1-hSNORF33-f (ATCC Patent Depository No. PTA-398) or plasmid pEXJ-hSNORF33-f (ATCC Patent Depository No. PTA-570). Nucleic acid analogs of the human SNORF33 receptor genes differ from the human SNORF33 receptor genes described herein in terms of the identity or location of one or more nucleic acid bases (deletion analogs containing less than all of the nucleic acid bases shown in FIGS. 5A-5B or contained in plasmid pcDNA3.1-hSNORF33-f (ATCC Patent Depository No. PTA-398) or plasmid pEXJ-hSNORF33-f (ATCC Patent Depository No. PTA-570), substitution analogs wherein one or more nucleic acid bases shown in FIGS. 5A-5B or contained in plasmid pcDNA3.1-hSNORF33-f (ATCC Patent Depository No. PTA-398) or plasmid pEXJ-hSNORF33-f (ATCC Patent Depository No. PTA-570), are replaced by other nucleic acid bases, and addition analogs, wherein one or more nucleic acid bases are added to a terminal or medial portion of the nucleic acid sequence) and which encode proteins which share some or all of the properties of the proteins encoded by the nucleic acid sequences shown in FIGS. 5A-5B or contained in plasmid pcDNA3.1-hSNORF33-f (ATCC Patent Depository No. PTA-398) or plasmid pEXJ-hSNORF33-f (ATCC Patent Depository No. PTA-570). In one embodiment of the present invention, the nucleic acid analog encodes a protein which has an amino acid sequence identical to that shown in FIGS. 6A-6B or encoded by the nucleic acid sequence contained in plasmid pcDNA3.1-hSNORF33-f (ATCC Patent Depository No. PTA-398) or plasmid pEXJ-hSNORF33-f (ATCC Patent Depository No. PTA-570). In another embodiment, the nucleic acid analog encodes a protein having an amino acid sequence which differs from the amino acid sequences shown in FIGS. 6A-6B or encoded by the nucleic acid contained in plasmid pcDNA3.1-hSNORF33-f (ATCC Patent Depository No. PTA-398) or plasmid pEXJ-hSNORF33-f (ATCC Patent Depository No. PTA-570). In a further embodiment, the protein encoded by the nucleic acid analog has a function which is the same as the function of the receptor proteins having the amino acid sequence shown in FIGS. 6A-6B. In another embodiment, the function of the protein encoded by the nucleic acid analog differs from the function of the receptor protein having the amino acid sequence shown in FIGS. 6A-6B. In another embodiment, the variation in the nucleic acid sequence occurs within the transmembrane (TM) region of the protein. In a further embodiment, the variation in the nucleic acid sequence occurs outside of the TM region.

The nucleic acids of the subject invention also include nucleic acid analogs of the mouse SNORF33 receptor genes, wherein the mouse SNORF33 receptor gene comprises the nucleic acid sequence shown in FIGS. 19A-19B or contained in plasmid pEXJ-mSNORF33-f (ATCC Patent Depository No. PTA-1665). Nucleic acid analogs of the mouse SNORF33 receptor genes differ from the mouse SNORF33 receptor genes described herein in terms of the identity or location of one or more nucleic acid bases (deletion analogs containing less than all of the nucleic acid bases shown in FIGS. 19A-19B or contained in plasmid pEXJ-mSNORF33-f (ATCC Patent Depository No. PTA-1665) substitution analogs wherein one or more nucleic acid bases shown in FIGS. 19A-19B or contained in plasmid pEXJ-mSNORF33-f (ATCC Patent Depository No. PTA-1665), are replaced by other nucleic acid bases, and addition analogs, wherein one or more nucleic acid bases are added to a terminal or medial portion of the nucleic acid sequence) and which encode proteins which share some or all of the properties of the proteins encoded by the nucleic acid sequences shown in FIGS. 19A-19B or contained in plasmid pEXJ-mSNORF33-f (ATCC Patent Depository No. PTA-1665). In one embodiment of the present invention, the nucleic acid analog encodes a protein which has an amino acid sequence identical to that shown in FIGS. 20A-20B or encoded by the nucleic acid sequence contained in plasmid pEXJ-mSNORF33-f (ATCC Patent Depository No. PTA-1665). In another embodiment, the nucleic acid analog encodes a protein having an amino acid sequence which differs from the amino acid sequences shown in FIGS. 20A-20B or encoded by the nucleic acid contained in plasmid pEXJ-mSNORF33-f (ATCC Patent Depository No. PTA-1665). In a further embodiment, the protein encoded by the nucleic acid analog has a function which is the same as the function of the receptor proteins having the amino acid sequence shown in FIGS. 20A-20B. In another embodiment, the function of the protein encoded by the nucleic acid analog differs from the function of the receptor protein having the amino acid sequence shown in FIGS. 20A-20B. In another embodiment, the variation in the nucleic acid sequence occurs within the transmembrane (TM) region of the protein. In a further embodiment, the variation in the nucleic acid sequence occurs outside of the TM region.

This invention provides the above-described isolated nucleic acid, wherein the nucleic acid is DNA. In an embodiment, the DNA is cDNA. In another embodiment, the DNA is genomic DNA. In still another embodiment, the nucleic acid is RNA. Methods for production and manipulation of nucleic acid molecules are well known in the art.

This invention further provides nucleic acid which is degenerate with respect to the DNA encoding any of the polypeptides described herein. In an embodiment, the nucleic acid comprises a nucleotide sequence which is degenerate with respect to the nucleotide sequence shown in FIG. 1 (SEQ ID NO: 1) or the nucleotide sequence contained in the plasmid pcDNA3.1-hSNORF33-p (ATCC Patent Depository No. PTA-101), that is, a nucleotide sequence which is translated into the same amino acid sequence. In another embodiment, the nucleic acid comprises a nucleotide sequence which is degenerate with respect to the nucleotide sequence shown in FIGS. 5A-5B (SEQ ID NO: 5) or the nucleotide sequence contained in the plasmid pcDNA3.1-hSNORF33-f (ATCC Patent Depository No. PTA-398) or the plasmid pEXJ-hS-NORF33-f (ATCC Patent Depository No. PTA-570), that is, a nucleotide sequence which is translated into the same amino acid sequence.

This invention further provides nucleic acid which is degenerate with respect to the DNA encoding any of the polypeptides described herein. In an embodiment, the nucleic acid comprises a nucleotide sequence which is degenerate with respect to the nucleotide sequence shown in FIGS. 3A-3B (SEQ ID NO: 3) or the nucleotide sequence contained in the plasmid pcDNA3.1-rSNORF33-f (ATCC Patent Depository No. PTA-102), that is, a nucleotide sequence which is translated into the same amino acid sequence.

This invention also encompasses DNAs and cDNAs which encode amino acid sequences which differ from those of the polypeptides of this invention, but which should not produce phenotypic changes.

Alternately, this invention also encompasses DNAs, cDNAs, and RNAs which hybridize to the DNA, cDNA, and RNA of the subject invention. Hybridization methods are well known to those of skill in the art.

The nucleic acids of the subject invention also include nucleic acid molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs wherein one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors. The creation of polypeptide analogs is well known to those of skill in the art (Spurney, R. F. et al. (1997); Fong, T. M. et al. (1995); Underwood, D. J. et al. (1994); Graziano, M. P. et al. (1996); Guan X. M. et al. (1995)).

The modified polypeptides of this invention may be transfected into cells either transiently or stably using methods well-known in the art, examples of which are disclosed herein. This invention also provides for binding assays using the modified polypeptides, in which the polypeptide is expressed either transiently or in stable cell lines. This invention further provides a compound identified using a modified polypeptide in a binding assay such as the binding assays described herein.

The nucleic acids described and claimed herein are useful for the information which they provide concerning the amino acid sequence of the polypeptide and as products for the large scale synthesis of the polypeptides by a variety of recombinant techniques. The nucleic acid molecule is useful for generating new cloning and expression vectors, transformed and transfected prokaryotic and eukaryotic host cells, and new and useful methods for cultured growth of such host cells capable of expression of the polypeptide and related products.

This invention also provides an isolated nucleic acid encoding species homologs of the SNORF33 receptor encoded by the nucleic acid sequence shown in FIG. 1 (SEQ ID NO: 1) or encoded by the plasmid pcDNA3.1-hSNORF33-p (ATCC Patent Depository No. PTA-101). In one embodiment, the nucleic acid encodes a mammalian SNORF33 receptor homolog which has substantially the same amino acid sequence as does the SNORF33 receptor encoded by the plasmid pcDNA3.1-hSNORF33-p (ATCC Patent Depository No. PTA-101). In another embodiment, the nucleic acid encodes a mammalian SNORF33 receptor homolog which has above 75% amino acid identity to the SNORF33 receptor encoded by the plasmid pcDNA3.1-hSNORF33-p (ATCC Patent Depository No. PTA-101); preferably above 85% amino acid identity to the SNORF33 receptor encoded by the plasmid pcDNA3.1-hSNORF33-p (ATCC Patent Depository No. PTA-101); most preferably above 95% amino acid identity to the SNORF33 receptor encoded by the plasmid pcDNA3.1-hSNORF33-p (ATCC Patent Depository No. PTA-101). In another embodiment, the mammalian SNORF33 receptor homolog has above 70% nucleic acid identity to the SNORF33 receptor gene contained in plasmid pcDNA3.1-hSNORF33-p (ATCC Patent Depository No. PTA-101); preferably above 80% nucleic acid identity to the SNORF33 receptor gene contained in the plasmid pcDNA3.1-hSNORF33-p (ATCC Patent Depository No. PTA-101); more preferably above 90% nucleic acid identity to the SNORF33 receptor gene contained in the plasmid pcDNA3.1-hSNORF33-p (ATCC Patent Depository No. PTA-101). Examples of methods for isolating and purifying species homologs are described elsewhere (e.g., U.S. Pat. No. 5,602,024, WO94/14957, WO97/26853, WO98/15570).

This invention also provides an isolated nucleic acid encoding species homologs of the SNORF33 receptors encoded by the nucleic acid sequence shown in FIGS. 5A-5B (SEQ ID NO: 5) or encoded by the plasmid pcDNA3.1-hSNORF33-f (ATCC Patent Depository No. PTA-398). In one embodiment, the nucleic acid encodes a mammalian SNORF33 receptor homolog which has substantially the same amino acid sequence as does the SNORF33 receptor encoded by the plasmid pcDNA3.1-hSNORF33-f (ATCC Patent Depository No. PTA-398). In another embodiment, the nucleic acid encodes a mammalian SNORF33 receptor homolog which has above 75% amino acid identity to the SNORF33 receptor encoded by the pcDNA3.1-hSNORF33-f (ATCC Patent Depository No. PTA-398); preferably above 85% amino acid identity to the SNORF33 receptor encoded by the plasmid pcDNA3.1-hSNORF33-f (ATCC Patent Depository No. PTA-398; most preferably above 95% amino acid identity to the SNORF33 receptor encoded by the plasmid pcDNA3.1-hSNORF33-f (ATCC Patent Depository No. PTA-398). In another embodiment, the mammalian SNORF33 receptor homolog has above 70% nucleic acid identity to the SNORF33 receptor gene contained in plasmid pcDNA3.1-hSNORF33-f (ATCC Patent Depository No. PTA-398); preferably above 80% nucleic acid identity to the SNORF33 receptor gene contained in the plasmid pcDNA3.1-hSNORF33-f (ATCC Patent Depository No. PTA-398); more preferably above 90% nucleic acid identity to the SNORF33 receptor gene contained in the plasmid pcDNA3.1-hSNORF33-f (ATCC Patent Depository No. PTA-398).

This invention also provides an isolated nucleic acid encoding species homologs of the SNORF33 receptors encoded by the nucleic acid sequence shown in FIGS. 5A-5B (SEQ ID NO: 5) or encoded by the plasmid pEXJ-hS-NORF33-f (ATCC Patent Depository No. PTA-570). In one embodiment, the nucleic acid encodes a mammalian SNORF33 receptor homolog which has substantially the same amino acid sequence as does the SNORF33 receptor encoded by the plasmid pEXJ-hSNORF33-f (ATCC Patent Depository No. PTA-570). In another embodiment, the nucleic acid encodes a mammalian SNORF33 receptor homolog which has above 75% amino acid identity to the SNORF33 receptor encoded by the plasmid pEXJ-hSNORF33-f (ATCC Patent Depository No. PTA-570); preferably above 85% amino acid identity to the SNORF33 receptor encoded by the plasmid pEXJ-hSNORF33-f (ATCC Patent Depository No. PTA-570); most preferably above 95% amino acid identity to the SNORF33 receptor encoded by the plasmid pEXJ-hSNORF33-f (ATCC Patent Depository No. PTA-570). In another embodiment, the mammalian SNORF33 receptor homolog has above 70% nucleic acid identity to the SNORF33 receptor gene contained in plasmid pEXJ-hSNORF33-f (ATCC Patent Depository No. PTA-570); preferably above 80% nucleic acid identity to the SNORF33 receptor gene contained in the plasmid pEXJ-hSNORF33-f (ATCC Patent Depository No. PTA-570); more preferably above 90% nucleic acid identity to the SNORF33 receptor gene contained in the plasmid pEXJ-hSNORF33-f (ATCC Patent Depository No. PTA-570).

This invention also provides an isolated nucleic acid encoding species homologs of the SNORF33 receptors encoded by the nucleic acid sequence shown in FIGS. 3A-3B (SEQ ID NO: 3) or encoded by the plasmid pcDNA3.1-rSNORF33-f (ATCC Patent Depository No. PTA-102). In one embodiment, the nucleic acid encodes a mammalian SNORF33 receptor homolog which has substantially the same amino acid sequence as does the SNORF33 receptor encoded by the plasmid pcDNA3.1-rSNORF33-f (ATCC Patent Depository No. PTA-102). In another embodiment, the nucleic acid encodes a mammalian SNORF33 receptor homolog which has above 75% amino acid identity to the SNORF33 receptor encoded by the pcDNA3.1-rSNORF33-f (ATCC Patent Depository No. PTA-102); preferably above 85% amino acid identity to the SNORF33 receptor encoded by the plasmid pcDNA3.1-rSNORF33-f (ATCC Patent Depository No. PTA-102); most preferably above 95% amino acid identity to the SNORF33 receptor encoded by the plasmid pcDNA3.1-rSNORF33-f (ATCC Patent Depository No. PTA-102). In another embodiment, the mammalian SNORF33 receptor homolog has above 70% nucleic acid identity to the SNORF33 receptor gene contained in plasmid pcDNA3.1-rSNORF33-f (ATCC Patent Depository No. PTA-102); preferably above 80% nucleic acid identity to the SNORF33 receptor gene contained in the plasmid pcDNA3.1-rSNORF33-f (ATCC Patent Depository No. PTA-102); more preferably above 90% nucleic acid identity to the SNORF33 receptor gene contained in the plasmid pcDNA3.1-rSNORF33-f (ATCC Patent Depository No. PTA-102).

This invention also provides an isolated nucleic acid encoding species homologs of the SNORF33 receptors encoded by the nucleic acid sequence shown in FIGS. 19A-19B (SEQ ID NO:36) or encoded by the plasmid pEXJ-mSNORF33-f (ATCC Patent Depository No. PTA-1665). In one embodiment, the nucleic acid encodes a mammalian SNORF33 receptor homolog which has substantially the same amino acid sequence as does the SNORF33 receptor encoded by the plasmid pEXJ-mSNORF33-f (ATCC Patent Depository No. PTA-1665). In another embodiment, the nucleic acid encodes a mammalian SNORF33 receptor homolog which has above 75% amino acid identity to the SNORF33 receptor encoded by the pEXJ-mSNORF33-f (ATCC Patent Depository No. PTA-1665); preferably above 85% amino acid identity to the SNORF33 receptor encoded by the plasmid pEXJ-mSNORF33-f (ATCC Patent Depository No. PTA-1665); most preferably above 95% amino acid identity to the SNORF33 receptor encoded by the plasmid pEXJ-mSNORF33-f (ATCC Patent Depository No. PTA-1665). In another embodiment, the mammalian SNORF33 receptor homolog has above 70% nucleic acid identity to the SNORF33 receptor gene contained in plasmid pEXJ-mSNORF33-f (ATCC Patent Depository No. PTA-1665); preferably above 80% nucleic acid identity to the SNORF33 receptor gene contained in the plasmid pEXJ-mSNORF33-f (ATCC Patent Depository No. PTA-1665); more preferably above 90% nucleic acid identity to the SNORF33 receptor gene contained in the plasmid pEXJ-mSNORF33-f (ATCC Patent Depository No. PTA-1665).

This invention provides an isolated nucleic acid encoding a modified mammalian SNORF33 receptor, which differs from a mammalian SNORF33 receptor by having an amino acid(s) deletion, replacement, or addition in the third intracellular domain.

This invention provides an isolated nucleic acid encoding a mammalian SNORF33 receptor. In one embodiment, the nucleic acid is DNA. In another embodiment, the DNA is cDNA. In another embodiment, the DNA is genomic DNA. In another embodiment, the nucleic acid is RNA. In another embodiment, the mammalian SNORF33 receptor is a human SNORF33 receptor. In another embodiment, the human SNORF33 receptor has an amino acid sequence identical to that encoded by the plasmid pcDNA3.1-hSNORF33-p (ATCC Patent Depository No. PTA-101), the plasmid pcDNA3.1-hSNORF33-f (ATCC Patent Depository No. PTA-398) or the plasmid pEXJ-hSNORF33-f (ATCC Patent Depository No. PTA-570). In another embodiment, the human SNORF33 receptor has an amino acid sequence identical to the amino acid sequence shown in FIG. 2 (SEQ ID NO: 2) or FIGS. 6A-6B (SEQ ID NO: 6).

In an embodiment, the mammalian SNORF33 receptor is a rat SNORF33 receptor. In another embodiment, the rat SNORF33 receptor has an amino acid sequence identical to that encoded by the plasmid pcDNA3.1-rSNORF33-f (ATCC Patent Depository No. PTA-102). In another embodiment, the rat SNORF33 receptor has an amino acid sequence identical to the amino acid sequence shown in FIGS. 4A-4B (SEQ ID NO: 4).

In a further embodiment, the mammalian SNORF33 receptor is a mouse SNORF33 receptor. In another embodiment, the mouse SNORF33 receptor has an amino acid sequence identical to that encoded by the plasmid pEXJ-mSNORF33-f (ATCC Patent Depository No. PTA-1665). In another embodiment, the mouse SNORF33 receptor has an amino acid sequence identical to the amino acid sequence shown in FIGS. 20A-20B (SEQ ID NO: 37).

This invention provides a purified mammalian SNORF33 receptor protein. In one embodiment, the SNORF33 receptor protein is a human SNORF33 receptor protein. In a further embodiment, the SNORF33 receptor protein is a rat SNORF33 receptor protein. In a further embodiment, the SNORF33 receptor protein is a mouse SNORF33 receptor protein.

This invention provides a vector comprising the nucleic acid of this invention. This invention further provides a vector adapted for expression in a cell which comprises the regulatory elements necessary for expression of the nucleic acid in the cell operatively linked to the nucleic acid encoding the receptor so as to permit expression thereof, wherein the cell is a bacterial, amphibian, yeast, insect or mammalian cell. In one embodiment, the vector is a baculovirus. In another embodiment, the vector is a plasmid.

This invention provides a plasmid designated pcDNA3.1-hSNORF33-p (ATCC Patent Depository No. PTA-101). This invention also provides a plasmid designated pcDNA3.1-rSNORF33-f (ATCC Patent Depository No. PTA-102). This invention provides a plasmid designated pcDNA3.1-hSNORF33-f (ATCC Patent Depository No. PTA-398). This invention provides a plasmid pEXJ-hSNORF33-f (ATCC Patent Depository No. PTA-570). This invention also provides a plasmid designated pEXJ-mSNORF33-f (ATCC Patent Depository No. PTA-1665).

This invention further provides for any vector or plasmid which comprises modified untranslated sequences, which are beneficial for expression in desired host cells or for use in binding or functional assays. For example, a vector or plasmid with untranslated sequences of varying lengths may express differing amounts of the polypeptide depending upon the host cell used. In an embodiment, the vector or plasmid comprises the coding sequence of the polypeptide and the regulatory elements necessary for expression in the host cell.

This invention provides for a cell comprising the vector of this invention. In one embodiment, the cell is a non-mammalian cell. In one embodiment, the non-mammalian cell is a *Xenopus* oocyte cell or a *Xenopus* melanophore cell. In another embodiment, the cell is a mammalian cell. In another embodiment, the cell is a COS-7 cell, a 293 human embryonic kidney cell, a NIH-3T3 cell, a LM(tk-) cell, a mouse Y1 cell, or a CHO cell. In another embodiment, the cell is an insect cell. In another embodiment, the insect cell is an Sf9 cell, an Sf21 cell or a *Trichoplusia ni* 5B-4 cell.

In one embodiment, the mammalian cell line is the 293 cell line designated 293-ratSNORF33-31. This cell line was deposited on May 3, 2000, with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure, and was accorded PTA-1806.

In another embodiment, the mammalian cell line is the CHO cell line designated CHO-ratSNORF33-7. This cell line was deposited on May 3, 2000, with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure, and was accorded PTA-1807.

This invention provides a membrane preparation isolated from the cell in accordance with this invention.

Furthermore, this invention provides for a nucleic acid probe comprising at least 15 nucleotides, which probe specifically hybridizes with a nucleic acid encoding a mammalian SNORF33 receptor, wherein the probe has a sequence complementary to a unique sequence present within one of the two strands of the nucleic acid encoding the mammalian SNORF33 receptor contained in plasmid pcDNA3.1-hSNORF33-p (ATCC Patent Depository No. PTA-101), plasmid pcDNA3.1-rSNORF33-f (ATCC Patent Depository No. PTA-102), plasmid pcDNA3.1-hSNORF33-f (ATCC Patent Depository No. PTA-398), plasmid pEXJ-hSNORF33-f (ATCC Patent Depository No. PTA-570) or plasmid pEXJ-mSNORF33-f (ATCC Patent Depository No. PTA-1665).

This invention further provides a nucleic acid probe comprising at least 15 nucleotides, which probe specifically hybridizes with a nucleic acid encoding a mammalian SNORF33 receptor, wherein the probe has a sequence complementary to a unique sequence present within (a) the nucleic acid sequence shown in FIG. 1 (SEQ ID NO: 1) or (b) the reverse complement thereof. This invention further provides a nucleic acid probe comprising at least 15 nucleotides, which probe specifically hybridizes with a nucleic acid encoding a mammalian SNORF33 receptor, wherein the probe has a sequence complementary to a unique sequence present within (a) the nucleic acid sequence shown in FIGS. 5A-5B (SEQ ID NO: 5) or (b) the reverse complement thereof. This invention also provides a nucleic acid probe comprising at least 15 nucleotides, which probe specifically hybridizes with a nucleic acid encoding a mammalian SNORF33 receptor, wherein the probe has a sequence complementary to a unique sequence present within (a) the nucleic acid sequence shown in FIGS. 3A-3B (SEQ ID NO: 3) or (b) the reverse complement thereof. This invention also provides a nucleic acid probe comprising at least 15 nucleotides, which probe specifically hybridizes with a nucleic acid encoding a mammalian SNORF33 receptor, wherein the probe has a sequence complementary to a unique sequence present within (a) the nucleic acid sequence shown in FIGS. 19A-19B (SEQ ID NO: 36) or (b) the reverse complement thereof. In one embodiment, the nucleic acid is DNA. In another embodiment, the nucleic acid is RNA.

As used herein, the phrase "specifically hybridizing" means the ability of a nucleic acid molecule to recognize a nucleic acid sequence complementary to its own and to form double-helical segments through hydrogen bonding between complementary base pairs.

The nucleic acids of this invention may be used as probes to obtain homologous nucleic acids from other species and to detect the existence of nucleic acids having complementary sequences in samples.

The nucleic acids may also be used to express the receptors they encode in transfected cells.

The use of a constitutively active receptor encoded by SNORF33 either occurring naturally without further modification or after appropriate point mutations, deletions or the like, allows screening for antagonists and in vivo use of such antagonists to attribute a role to receptor SNORF33 without prior knowledge of the endogenous ligand.

Use of the nucleic acids further enables elucidation of possible receptor diversity and of the existence of multiple subtypes within a family of receptors of which SNORF33 is a member.

Finally, it is contemplated that this receptor will serve as a valuable tool for designing drugs for treating various pathophysiological conditions such as chronic and acute inflammation, arthritis, autoimmune diseases, transplant rejection, graft vs. host disease, bacterial, fungal, protozoan and viral infections, septicemia, AIDS, pain, psychotic and neurological disorders, including anxiety, depression, schizophrenia, dementia, mental retardation, memory loss, epilepsy, neuromotor disorders, respiratory disorders, asthma, eating/body weight disorders including obesity, bulimia, diabetes, anorexia, nausea, hypertension, hypotension, vascular and cardiovascular disorders, ischemia, stroke, cancers, ulcers, urinary retention, sexual/reproductive disorders, circadian rhythm disorders, renal disorders, bone diseases including osteoporosis, benign prostatic hypertrophy, gastrointestinal disorders, nasal congestion, dermatological disorders such as psoriasis, allergies, Parkinson's disease, Alzheimer's disease, acute heart failure, angina disorders, delirium, dyskinesias such as Huntington's disease or Gille's de la Tourette's syndrome, among others and diagnostic assays for such conditions. This receptor may also serve as a valuable tool for designing drugs for chemoprevention.

Methods of transfecting cells e.g. mammalian cells, with such nucleic acid to obtain cells in which the receptor is expressed on the surface of the cell are well known in the art.

(See, for example, U.S. Pat. Nos. 5,053,337; 5,155,218; 5,360,735; 5,472,866; 5,476,782; 5,516,653; 5,545,549; 5,556,753; 5,595,880; 5,602,024; 5,639,652; 5,652,113; 5,661,024; 5,766,879; 5,786,155; and 5,786,157, the disclosures of which are hereby incorporated by reference in their entireties into this application.)

Such transfected cells may also be used to test compounds and screen compound libraries to obtain compounds which bind to the SNORF33 receptor, as well as compounds which activate or inhibit activation of functional responses in such cells, and therefore are likely to do so in vivo. (See, for example, U.S. Pat. Nos. 5,053,337; 5,155,218; 5,360,735; 5,472,866; 5,476,782; 5,516,653; 5,545,549; 5,556,753; 5,595,880; 5,602,024; 5,639,652; 5,652,113; 5,661,024; 5,766,879; 5,786,155; and 5,786,157, the disclosures of which are hereby incorporated by reference in their entireties into this application.)

This invention further provides an antibody capable of binding to a mammalian receptor encoded by a nucleic acid encoding a mammalian receptor. In one embodiment, the mammalian receptor is a human receptor. In a further embodiment, the mammalian receptor is a rat receptor. This invention also provides an agent capable of competitively inhibiting the binding of the antibody to a mammalian receptor. In one embodiment, the antibody is a monoclonal antibody or antisera.

Methods of preparing and employing antisense oligonucleotides, antibodies, nucleic acid probes and transgenic animals directed to the SNORF33 receptor are well known in the art. (See, for example, U.S. Pat. Nos. 5,053,337; 5,155,218; 5,360,735; 5,472,866; 5,476,782; 5,516,653; 5,545,549; 5,556,753; 5,595,880; 5,602,024; 5,639,652; 5,652,113; 5,661,024; 5,766,879; 5,786,155; and 5,786,157, the disclosures of which are hereby incorporated by reference in their entireties into this application.)

This invention provides for an antisense oligonucleotide having a sequence capable of specifically hybridizing to RNA encoding a mammalian SNORF33 receptor, so as to prevent translation of such RNA. This invention further provides for an antisense oligonucleotide having a sequence capable of specifically hybridizing to genomic DNA encoding a mammalian SNORF33 receptor, so as to prevent transcription of such genomic DNA. In one embodiment, the oligonucleotide comprises chemically modified nucleotides or nucleotide analogues.

This invention also provides for an antibody capable of binding to a mammalian SNORF33 receptor encoded by a nucleic acid in accordance with this invention. In one embodiment, the mammalian SNORF33 receptor is a human SNORF33 receptor. In a further embodiment, the mammalian SNORF33 receptor is a rat or a mouse SNORF33 receptor.

Moreover, this invention provides an agent capable of competitively inhibiting the binding of an antibody in accordance with this invention to a mammalian SNORF33 receptor. In one embodiment, the antibody is a monoclonal antibody or antisera.

This invention still further provides a pharmaceutical composition comprising (a) an amount of an oligonucleotide in accordance with this invention capable of passing through a cell membrane and effective to reduce expression of a mammalian SNORF33 receptor and (b) a pharmaceutically acceptable carrier capable of passing through the cell membrane.

In one embodiment, the oligonucleotide is coupled to a substance which inactivates mRNA. In another embodiment, the substance which inactivates mRNA is a ribozyme. In another embodiment, the pharmaceutically acceptable carrier comprises a structure which binds to a mammalian SNORF33 receptor on a cell capable of being taken up by the cells after binding to the structure. In another embodiment, the pharmaceutically acceptable carrier is capable of binding to a mammalian SNORF33 receptor which is specific for a selected cell type.

This invention also provides a pharmaceutical composition which comprises an amount of an antibody in accordance with this invention effective to block binding of a ligand to a human SNORF33 receptor and a pharmaceutically acceptable carrier.

This invention further provides a transgenic, nonhuman mammal expressing DNA encoding a mammalian SNORF33 receptor in accordance with this invention. This invention provides a transgenic, nonhuman mammal comprising a homologous recombination knockout of a native mammalian SNORF33 receptor. This invention further provides a transgenic, nonhuman mammal whose genome comprises antisense DNA complementary to DNA encoding a mammalian SNORF33 receptor in accordance with this invention so placed within such genome as to be transcribed into antisense mRNA which is complementary and hybridizes with mRNA encoding the mammalian SNORF33 receptor so as to thereby reduce translation or such mRNA and expression of such receptor. In one embodiment, the DNA encoding the mammalian SNORF33 receptor additionally comprises an inducible promoter. In another embodiment, the DNA encoding the mammalian SNORF33 receptor additionally comprises tissue specific regulatory elements. In another embodiment, the transgenic, nonhuman mammal is a mouse.

Animal model systems which elucidate the physiological and behavioral roles of the SNORF33 receptor are produced by creating transgenic animals in which the activity of the SNORF33 receptor is either increased or decreased, or the amino acid sequence of the expressed SNORF33 receptor is altered, by a variety of techniques. Examples of these techniques include, but are not limited to: 1) Insertion of normal or mutant versions of DNA encoding a SNORF33 receptor, by microinjection, electroporation, retroviral transfection or other means well known to those skilled in the art, into appropriate fertilized embryos in order to produce a transgenic animal or 2) Homologous recombination of mutant or normal, human or animal versions of these genes with the native gene locus to produce transgenic animals with alterations in the regulation of expression or in the structure of these SNORF33 receptor sequences. The technique of homologous recombination is well known in the art. It replaces the native gene with the inserted gene and so is useful for producing an animal that cannot express native SNORF33 receptors but does express, for example, an inserted mutant SNORF33 receptor, which has replaced the native SNORF33 receptor in the animal's genome by recombination, resulting in underexpression of the receptor. Microinjection adds genes to the genome, but does not remove them, and so is useful for producing an animal which expresses its native SNORF33 receptors, as well as overexpressing exogenously added SNORF33 receptors, perhaps in a tissue-specific manner.

One means available for producing a transgenic animal, with a mouse as an example, is as follows: Female mice are mated, and the resulting fertilized eggs are dissected out of their oviducts. The eggs are stored in an appropriate medium such as M2 medium. DNA or cDNA encoding a SNORF33 receptor is purified from a vector by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

A second means available for producing a transgenic animal, with a mouse as an example, is as follows: Embryonic stem cells (ES cells) are harvested from the inner cell mass of mouse blastocysts. A DNA construct is generated which contains several kb of the SNORF33 gene and flanking regions, with a selectable marker, such as one conferring neomycin resistance, inserted within the SNORF33 coding region and perhaps a negatively selectable gene inserted outside the homologous region. ES cells are then transformed with this DNA construct, and homologous recombination occurs. Southern blot analysis and/or PCR analysis may be used to screen for cells that have incorporated the SNORF33 construct into the correct genomic locus. Donor females are mated, blastocysts are harvested, and selected ES cells are injected into the blastocysts. These blastocysts are then implanted into the uterus of pseudopregnant mice, as above. The heterozygous offspring from these mice are then mated to produce mice homozygous for the transgene.

This invention provides for a process for identifying a chemical compound which specifically binds to a mammalian SNORF33 receptor which comprises contacting cells containing DNA encoding, and expressing on their cell surface, the mammalian SNORF33 receptor, wherein such cells do not normally express the mammalian SNORF33 receptor, with the compound under conditions suitable for binding, and detecting specific binding of the chemical compound to the mammalian SNORF33 receptor. This invention further provides for a process for identifying a chemical compound which specifically binds to a mammalian SNORF33 receptor which comprises contacting a membrane preparation from cells containing DNA encoding and expressing on their cell surface the mammalian SNORF33 receptor, wherein such cells do not normally express the mammalian SNORF33 receptor, with the compound under conditions suitable for binding, and detecting specific binding of the chemical compound to the mammalian SNORF33 receptor.

In one embodiment, the mammalian SNORF33 receptor is a human SNORF33 receptor. In another embodiment, the mammalian SNORF33 receptor has substantially the same amino acid sequence as the human SNORF33 receptor encoded by plasmid pcDNA3.1-hSNORF33-f (ATCC Patent Depository No. PTA-398). In another embodiment, the mammalian SNORF33 receptor has substantially the same amino acid sequence as the human SNORF33 receptor encoded by plasmid pEXJ-hSNORF33-f (ATCC Patent Depository No. PTA-570). In another embodiment, the mammalian SNORF33 receptor has substantially the same amino acid sequence as that shown in FIGS. 6A-6B (SEQ ID NO: 6). In another embodiment, the mammalian. SNORF33 receptor has the amino acid sequence shown in FIGS. 6A-6B (SEQ ID NO: 6).

In another embodiment, the mammalian SNORF33 receptor is a rat SNORF33 receptor. In another embodiment, the mammalian SNORF33 receptor has substantially the same amino acid sequence as the rat SNORF33 receptor encoded by plasmid pcDNA3.1-rSNORF33-f (ATCC Patent Depository No. PTA-102). In another embodiment, the mammalian SNORF33 receptor has substantially the same amino acid sequence as that shown in FIGS. 4A-4B (SEQ ID NO: 4). In another embodiment, the mammalian SNORF33 receptor has the amino acid sequence shown in FIGS. 4A-4B (SEQ ID NO: 4).

In another embodiment, the mammalian SNORF33 receptor is a mouse SNORF33 receptor. In another embodiment, the mammalian SNORF33 receptor has substantially the same amino acid sequence as the mouse SNORF33 receptor encoded by plasmid pEXJ-mSNORF33-f (ATCC Patent Depository No. PTA-1665). In another embodiment, the mammalian SNORF33 receptor has substantially the same amino acid sequence as that shown in FIGS. 20A-20B (SEQ ID NO: 37). In another embodiment, the mammalian SNORF33 receptor has the amino acid sequence shown in FIGS. 20A-20B (SEQ ID NO: 37).

In one embodiment, the compound is not previously known to bind to a mammalian SNORF33 receptor. In one embodiment, the cell is an insect cell. In one embodiment, the cell is a mammalian cell. In another embodiment, the cell is normeuronal in origin. In another embodiment, the normeuronal cell is a COS-7 cell, 293 human embryonic kidney cell, a CHO cell, a NIH-3T3 cell, a mouse Y1 cell, or a LM(tk-) cell. In another embodiment, the compound is a compound not previously known to bind to a mammalian SNORF33 receptor. This invention provides a compound identified by the preceding process according to this invention.

This invention still further provides a process involving competitive binding for identifying a chemical compound which specifically binds to a mammalian SNORF33 receptor which comprises separately contacting cells expressing on their cell surface the mammalian SNORF33 receptor, wherein such cells do not normally express the mammalian SNORF33 receptor, with both the chemical compound and a second chemical compound known to bind to the receptor, and with only the second chemical compound, under conditions suitable for binding of such compounds to the receptor, and detecting specific binding of the chemical compound to the mammalian SNORF33 receptor, a decrease in the binding of the second chemical compound to the mammalian SNORF33 receptor in the presence of the chemical compound being tested indicating that such chemical compound binds to the mammalian SNORF33 receptor.

This invention provides a process involving competitive binding for identifying a chemical compound which specifically binds to a mammalian SNORF33 receptor which comprises separately contacting a membrane preparation from cells expressing on their cell surface the mammalian SNORF33 receptor, wherein such cells do not normally express the mammalian SNORF33 receptor, with both the chemical compound and a second chemical compound known to bind to the receptor, and with only the second chemical compound, under conditions suitable for binding of such compounds to the receptor, and detecting specific binding of the chemical compound to the mammalian SNORF33 receptor, a decrease in the binding of the second chemical compound to the mammalian SNORF33 receptor in the presence of the chemical compound being tested indicating that such chemical compound binds to the mammalian SNORF33 receptor.

In an embodiment of the present invention, the second chemical compound is a trace amine. Examples of trace amines include, but are not limited to, tryptamine (TYR), tyramine (T), octopamine (OCT), and β-phenyl-ethylamine (PEA).

In one embodiment, the mammalian SNORF33 receptor is a human SNORF33 receptor. In another embodiment, the mammalian SNORF33 receptor is a rat or a mouse SNORF33 receptor. In a further embodiment, the cell is an insect cell. In another embodiment, the cell is a mammalian cell. In another embodiment, the cell is normeuronal in origin. In another embodiment, the normeuronal cell is a COS-7 cell, 293 human embryonic kidney cell, a CHO cell, a NIH-3T3 cell, a mouse Y1 cell, or a LM(tk-) cell. In another embodiment, the compound is not previously known to bind to a mammalian SNORF33 receptor. This invention provides for a compound identified by the preceding process according to this invention.

This invention provides for a method of screening a plurality of chemical compounds not known to bind to a mammalian SNORF33 receptor to identify a compound which specifically binds to the mammalian SNORF33 receptor, which comprises (a) contacting cells transfected with, and expressing, DNA encoding the mammalian SNORF33 receptor with a compound known to bind specifically to the mammalian SNORF33 receptor; (b) contacting the cells of step (a) with the plurality of compounds not known to bind specifically to the mammalian SNORF33 receptor, under conditions permitting binding of compounds known to bind to the mammalian SNORF33 receptor; (c) determining whether the binding of the compound known to bind to the mammalian SNORF33 receptor is reduced in the presence of the plurality of compounds, relative to the binding of the compound in the absence of the plurality of compounds; and if so (d) separately determining the binding to the mammalian SNORF33 receptor of each compound included in the plurality of compounds, so as to thereby identify any compound included therein which specifically binds to the mammalian SNORF33 receptor.

This invention provides a method of screening a plurality of chemical compounds not known to bind to a mammalian SNORF33 receptor to identify a compound which specifically binds to the mammalian SNORF33 receptor, which comprises (a) contacting a membrane preparation from cells transfected with, and expressing, DNA encoding the mammalian SNORF33 receptor with the plurality of compounds not known to bind specifically to the mammalian SNORF33 receptor under conditions permitting binding of compounds known to bind to the mammalian SNORF33 receptor; (b) determining whether the binding of a compound known to bind to the mammalian SNORF33 receptor is reduced in the presence of the plurality of compounds, relative to the binding of the compound in the absence of the plurality of compounds; and if so (c) separately determining the binding to the mammalian SNORF33 receptor of each compound included in the plurality of compounds, so as to thereby identify any compound included therein which specifically binds to the mammalian SNORF33 receptor.

In one embodiment, the mammalian SNORF33 receptor is a human SNORF33 receptor. In a further embodiment, the mammalian SNORF33 receptor is a rat or a mouse SNORF33 receptor. In another embodiment, the cell is a mammalian cell. In another embodiment, the mammalian cell is non-neuronal in origin. In a further embodiment, the non-neuronal cell is a COS-7 cell, a 293 human embryonic kidney cell, a LM(tk-) cell, a CHO cell, a mouse Y1 cell, or an NIH-3T3 cell.

This invention also provides a method of detecting expression of a mammalian SNORF33 receptor by detecting the presence of mRNA coding for the mammalian SNORF33 receptor which comprises obtaining total mRNA from the cell and contacting the mRNA so obtained with a nucleic acid probe according to this invention under hybridizing conditions, detecting the presence of mRNA hybridized to the probe, and thereby detecting the expression of the mammalian SNORF33 receptor by the cell.

This invention further provides for a method of detecting the presence of a mammalian SNORF33 receptor on the surface of a cell which comprises contacting the cell with an antibody according to this invention under conditions permitting binding of the antibody to the receptor, detecting the presence of the antibody bound to the cell, and thereby detecting the presence of the mammalian SNORF33 receptor on the surface of the cell.

This invention still further provides a method of determining the physiological and behavioral effects of varying levels of activity of mammalian SNORF33 receptors which comprises producing a transgenic, nonhuman mammal in accordance with this invention whose levels of mammalian SNORF33 receptor activity are varied by use of an inducible promoter which regulates mammalian SNORF33 receptor expression.

This invention additionally provides a method of determining the physiological and behavioral effects of varying levels of activity of mammalian SNORF33 receptors which comprises producing a panel of transgenic, nonhuman mammals in accordance with this invention each expressing a different amount of mammalian SNORF33 receptor.

Moreover, this invention provides method for identifying an antagonist capable of alleviating an abnormality wherein the abnormality is alleviated by decreasing the activity of a mammalian SNORF33 receptor comprising administering a compound to a transgenic, nonhuman mammal according to this invention, and determining whether the compound alleviates any physiological and/or behavioral abnormality displayed by the transgenic, nonhuman mammal as a result of overactivity of a mammalian SNORF33 receptor, the alleviation of such an abnormality identifying the compound as an antagonist. In one embodiment, the mammalian SNORF33 receptor is a human SNORF33 receptor. In a further embodiment, the mammalian SNORF33 receptor is a rat SNORF33 receptor. The invention also provides an antagonist identified by the preceding method according to this invention. This invention further provides a Composition, e.g. a pharmaceutical composition comprising an antagonist according to this invention and a carrier, e.g. a pharmaceutically acceptable carrier. This invention provides a method of treating an abnormality in a subject wherein the abnormality is alleviated by decreasing the activity of a mammalian SNORF33 receptor which comprises administering to the subject an effective amount of the pharmaceutical composition according to this invention so as to thereby treat the abnormality.

In addition, this invention provides a method for identifying an agonist capable of alleviating an abnormality in a subject wherein the abnormality is alleviated by increasing the activity of a mammalian SNORF33 receptor comprising administering a compound to a transgenic, nonhuman mammal according to this invention, and determining whether the compound alleviates any physiological and/or behavioral abnormality displayed by the transgenic, nonhuman mammal, the alleviation of such an abnormality identifying the compound as an agonist. In one embodiment, the mammalian SNORF33 receptor is a human SNORF33 receptor. In a further embodiment, the mammalian SNORF33 receptor is a rat SNORF33 receptor. This invention provides an agonist identified by the preceding method according to this invention.

This invention provides a composition, e.g. a pharmaceutical composition comprising an agonist identified by a method according to this invention and a carrier, e.g. a pharmaceutically acceptable carrier.

Moreover, this invention provides a method of treating an abnormality in a subject wherein the abnormality is alleviated by increasing the activity of a mammalian SNORF33 receptor which comprises administering to the subject an effective amount of the pharmaceutical composition of this invention so as to thereby treat the abnormality.

Yet further, this invention provides a method for diagnosing a predisposition to a disorder associated with the activity of a specific mammalian allele which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a mammalian SNORF33 receptor and labeled with a detectable marker; (e) detecting labeled bands which have hybridized to the DNA encoding a mammalian SNORF33 receptor to create a unique band pattern specific to the DNA of subjects suffering from the disorder; (f) repeating steps (a)-(e) with DNA obtained for diagnosis from subjects not yet suffering from the disorder; and (g) comparing the unique band pattern specific to the DNA of subjects suffering from the disorder from step (e) with the band pattern from step (f) for subjects not yet suffering from the disorder so as to determine whether the patterns are the same or different and thereby diagnose predisposition to the disorder if the patterns are the same.

In one embodiment, the disorder is a disorder associated with the activity of a specific mammalian allele is diagnosed.

This invention also provides a method of preparing a purified mammalian SNORF33 receptor according to this invention which comprises: (a) culturing cells which express the mammalian SNORF33 receptor; (b) recovering the mammalian SNORF33 receptor from the cells; and (c) purifying the mammalian SNORF33 receptor so recovered.

This invention further provides a method of preparing a purified mammalian SNORF33 receptor according to this invention which comprises: (a) inserting a nucleic acid encoding the mammalian SNORF33 receptor into a suitable expression vector; (b) introducing the resulting vector into a suitable host cell; (c) placing the resulting host cell in suitable condition permitting the production of the mammalian SNORF33 receptor; (d) recovering the mammalian SNORF33 receptor so produced; and optionally (e) isolating and/or purifying the mammalian SNORF33 receptor so recovered.

Furthermore, this invention provides a process for determining whether a chemical compound is a mammalian SNORF33 receptor agonist which comprises contacting cells transfected with and expressing DNA encoding the mammalian SNORF33 receptor with the compound under conditions permitting the activation of the mammalian SNORF33 receptor, and detecting any increase in mammalian SNORF33 receptor activity, so as to thereby determine whether the compound is a mammalian SNORF33 receptor agonist.

This invention also provides a process for determining whether a chemical compound is a mammalian SNORF33 receptor antagonist which comprises contacting cells transfected with and expressing DNA encoding the mammalian SNORF33 receptor with the compound in the presence of a known mammalian SNORF33 receptor agonist, under conditions permitting the activation of the mammalian SNORF33 receptor, and detecting any decrease in mammalian SNORF33 receptor activity, so as to thereby determine whether the compound is a mammalian SNORF33 receptor antagonist.

In one embodiment, the mammalian SNORF33 receptor is a human SNORF33 receptor. In another embodiment, the mammalian SNORF33 receptor is a rat or a mouse SNORF33 receptor.

This invention still further provides a composition, for example a pharmaceutical composition, which comprises an amount of a mammalian SNORF33 receptor agonist determined by a process according to this invention effective to increase activity of a mammalian SNORF33 receptor and a carrier, for example, a pharmaceutically acceptable carrier. In one embodiment, the mammalian SNORF33 receptor agonist is not previously known.

Also, this invention provides a composition, for example a pharmaceutical composition, which comprises an amount of a mammalian SNORF33 receptor antagonist determined by a process according to this invention effective to reduce activity of a mammalian SNORF33 receptor and a carrier, for example, a pharmaceutically acceptable carrier. In one embodiment, the mammalian SNORF33 receptor antagonist is not previously known.

This invention moreover provides a process for determining whether a chemical compound specifically binds to and activates a mammalian SNORF33 receptor, which comprises contacting cells producing a second messenger response and expressing on their cell surface the mammalian SNORF33 receptor, wherein such cells do not normally express the mammalian SNORF33 receptor, with the chemical compound under conditions suitable for activation of the mammalian SNORF33 receptor, and measuring the second messenger response in the presence and in the absence of the chemical compound, a change, e.g. an increase, in the second messenger response in the presence of the chemical compound indicating that the compound activates the mammalian SNORF33 receptor.

In one embodiment, the second messenger response comprises chloride channel activation and the change in second messenger is an increase in the level of chloride current. In another embodiment, the second messenger response comprises change in intracellular calcium levels and the change in second messenger is an increase in the measure of intracellular calcium. In another embodiment, the second messenger response comprises release of inositol phosphate and the change in second messenger is an increase in the level of inositol phosphate. In another embodiment, the second messenger response comprises release of arachidonic acid and the change in second messenger is an increase in the level of arachidonic acid. In yet another embodiment, the second messenger response comprises GTPγS ligand binding and the change in second messenger is an increase in GTPγS ligand binding. In another embodiment, the second messenger response comprises activation of MAP kinase and the change in second messenger response is an increase in MAP kinase activation. In a further embodiment, the second messenger response comprises cAMP accumulation and the change in second messenger response is a reduction in cAMP accumulation.

This invention still further provides a process for determining whether a chemical compound specifically binds to and inhibits activation of a mammalian SNORF33 receptor, which comprises separately contacting cells producing a second messenger response and expressing on their cell surface the mammalian SNORF33 receptor, wherein such cells do not normally express the mammalian SNORF33 receptor, with both the chemical compound and a second chemical compound known to activate the mammalian SNORF33 receptor, and with only the second chemical compound, under conditions suitable for activation of the mammalian SNORF33 receptor, and measuring the second messenger response in the presence of only the second chemical compound and in the presence of both the second chemical compound and the chemical compound, a smaller change, e.g. increase, in the second messenger response in the presence of both the chemical compound and the second chemical compound than in the presence of only the second chemical compound indicating that the chemical compound inhibits activation of the mammalian SNORF33 receptor.

In an embodiment of the present invention, the second chemical compound is a trace amine. Examples of trace amines include, but are not limited to, tryptamine (TYR), tyramine (T), octopamine (OCT), and β-phenyl-ethylamine (PEA).

In one embodiment, the second messenger response comprises chloride channel activation and the change in second messenger response is a smaller increase in the level of chloride current in the presence of both the chemical compound and the second chemical compound than in the presence of only the second chemical compound. In another embodiment, the second messenger response comprises change in intracellular calcium levels and the change in second messenger response is a smaller increase in the measure of intracellular calcium in the presence of both the chemical compound and the second chemical compound than in the presence of only the second chemical compound. In another embodiment, the second messenger response comprises release of inositol phosphate and the change in second messenger response is a smaller increase in the level of inositol phosphate in the presence of both the chemical compound and the second chemical compound than in the presence of only the second chemical compound.

In one embodiment, the second messenger response comprises activation of MAP kinase and the change in second messenger response is a smaller increase in the level of MAP kinase activation in the presence of both the chemical compound and the second chemical compound than in the presence of only the second chemical compound. In another embodiment, the second messenger response comprises change in cAMP levels and the change in second messenger response is a smaller change in the level of cAMP in the presence of both the chemical compound and the second chemical compound than in the presence of only the second chemical compound. In another embodiment, the second messenger response comprises release of arachidonic acid and the change in second messenger response is an increase in the level of arachidonic acid levels in the presence of both the chemical compound and the second chemical compound than in the presence of only the second chemical compound. In a further embodiment, the second messenger response comprises GTPγS ligand binding and the change in second messenger is a smaller increase in GTPγS ligand binding in the presence of both the chemical compound and the second chemical compound than in the presence of only the second chemical compound.

In one embodiment, the mammalian SNORF33 receptor is a human SNORF33 receptor. In a further embodiment, the mammalian SNORF33 receptor is a rat or a mouse SNORF33 receptor. In another embodiment, the cell is an insect cell. In another embodiment, the cell is a mammalian cell. In another embodiment, the mammalian cell is normeuronal in origin. In another embodiment, the normeuronal cell is a COS-7 cell, CHO cell, 293 human embryonic kidney cell, NIH-3T3 cell or LM(tk-) cell. In another embodiment, the compound is not previously known to bind to a mammalian SNORF33 receptor.

Further, this invention provides a compound determined by a process according to this invention and a composition, for example, a pharmaceutical composition, which comprises an amount of a mammalian SNORF33 receptor agonist determined to be such by a process according to this invention effective to increase activity of the mammalian SNORF33 receptor and a carrier, for example, a pharmaceutically acceptable carrier. In one embodiment, the mammalian SNORF33 receptor agonist is not previously known.

This invention also provides a composition, for example, a pharmaceutical composition, which comprises an amount of a mammalian SNORF33 receptor antagonist determined to be such by a process according to this invention, effective to reduce activity of the mammalian SNORF33 receptor and a carrier, for example a pharmaceutically acceptable carrier. In one embodiment, the mammalian SNORF33 receptor antagonist is not previously known.

This invention yet further provides a method of screening a plurality of chemical compounds not known to activate a mammalian SNORF33 receptor to identify a compound which activates the mammalian SNORF33 receptor which comprises: (a) contacting cells transfected with and expressing the mammalian SNORF33 receptor with the plurality of compounds not known to activate the mammalian SNORF33 receptor, under conditions permitting activation of the mammalian SNORF33 receptor; (b) determining whether the activity of the mammalian SNORF33 receptor is increased in the presence of one or more of the compounds; and if so (c) separately determining whether the activation of the mammalian SNORF33 receptor is increased by any compound included in the plurality of compounds, so as to thereby identify each compound which activates the mammalian SNORF33 receptor. In one embodiment, the mammalian SNORF33 receptor is a human SNORF33 receptor. In a further embodiment, the mammalian SNORF33 receptor is a rat or a mouse SNORF33 receptor.

This invention provides a method of screening a plurality of chemical compounds not known to inhibit the activation of a mammalian SNORF33 receptor to identify a compound which inhibits the activation of the mammalian SNORF33 receptor, which comprises: (a) contacting cells transfected with and expressing the mammalian SNORF33 receptor with the plurality of compounds in the presence of a known mammalian SNORF33 receptor agonist, under conditions permitting activation of the mammalian SNORF33 receptor; (b) determining whether the extent or amount of activation of the mammalian SNORF33 receptor is reduced in the presence of one or more of the compounds, relative to the extent or amount of activation of the mammalian SNORF33 receptor in the absence of such one or more compounds; and if so (c) separately determining whether each such compound inhibits activation of the mammalian SNORF33 receptor for each compound included in the plurality of compounds, so as to thereby identify any compound included in such plurality of compounds which inhibits the activation of the mammalian SNORF33 receptor.

In one embodiment, the mammalian SNORF33 receptor is a human SNORF33 receptor. In a further embodiment, the mammalian SNORF33 receptor is a rat or a mouse SNORF33 receptor. In another embodiment, wherein the cell is a mammalian cell. In another embodiment, the mammalian cell is non-neutonal in origin. In another embodiment, the non-neuronal cell is a COS-7 cell, a 293 human embryonic kidney cell, a LM(tk-) cell or an NIH-3T3 cell.

This invention also provides a composition, for example, a pharmaceutical composition, comprising a compound identified by a method according to this invention in an amount effective to increase mammalian SNORF33 receptor activity and a carrier, for example, a pharmaceutically acceptable carrier.

This invention still further provides a composition, for example, a pharmaceutical composition, comprising a compound identified by a method according to this invention in an amount effective to decrease mammalian SNORF33 receptor activity and a carrier, for example, a pharmaceutically acceptable carrier.

Furthermore, this invention provides a method of treating an abnormality in a subject wherein the abnormality is alleviated by increasing the activity of a mammalian SNORF33 receptor which comprises administering to the subject a compound which is a mammalian SNORF33 receptor agonist in an amount effective to treat the abnormality. In one embodiment, the abnormality is a regulation of a steroid hormone disorder, an epinephrine release disorder, a gastrointestinal disorder, a cardiovascular disorder, an electrolyte balance disorder, hypertension, diabetes, a respiratory disorder, asthma, a reproductive function disorder, an immune disorder, an endocrine disorder, a musculoskeletal disorder, a neuroendocrine disorder, a cognitive disorder, a memory disorder, somatosensory and neurotransmission disorders, a motor coordination disorder, a sensory integration disorder, a motor integration disorder, Attention Deficit Hyperactivity Disorder, a dopaminergic function disorder, an appetite disorder, such as anorexia or obesity, a sensory transmission disorder, an olfaction disorder, an autonomic nervous system disorder, pain, psychotic behavior, affective disorder, migraine, circadian disorders, sleep disorders, visual disorders, urinary disorders, blood coagulation-related disorders, developmental disorders, opthalmic disorders, such as glaucoma and conjunctivitis, or ischemia-reperfusion injury-related diseases.

This invention additionally provides a method of treating an abnormality in a subject wherein the abnormality is alleviated by decreasing the activity of a mammalian SNORF33 receptor which comprises administering to the subject a compound which is a mammalian SNORF33 receptor antagonist in an amount effective to treat the abnormality. In one embodiment, the abnormality is a regulation of a steroid hormone disorder, an epinephrine release disorder, a gastrointestinal disorder, a cardiovascular disorder, an electrolyte balance disorder, hypertension, diabetes, a respiratory disorder, asthma, a reproductive function disorder, an immune disorder, an endocrine disorder, a musculoskeletal disorder, a neuroendocrine disorder, a cognitive disorder, a memory disorder, somatosensory and neurotransmission disorders, a motor coordination disorder, a sensory integration disorder, a motor integration disorder, Attention Deficit Hyperactivity Disorder, a dopaminergic function disorder, an appetite disorder, such as anorexia or obesity, a sensory transmission disorder, an olfaction disorder, an autonomic nervous system disorder, pain, psychotic behavior, affective disorder, migraine, circadian disorders, sleep disorders, visual disorders, urinary disorders, blood coagulation-related disorders, developmental disorders, opthalmic disorders, such as glaucoma and conjunctivitis, or ischemia-reperfusion injury-related diseases.

This invention also provides a process for making a composition of matter which specifically binds to a mammalian SNORF33 receptor which comprises identifying a chemical compound using a process in accordance with this invention and then synthesizing the chemical compound or a novel structural and functional analog or homolog thereof. In one embodiment, the mammalian SNORF33 receptor is a human SNORF33 receptor. In another embodiment, the mammalian SNORF33 receptor is a rat or mouse SNORF33 receptor.

This invention further provides a process for preparing a composition, for example a pharmaceutical composition which comprises admixing a carrier, for example, a pharmaceutically acceptable carrier, and a pharmaceutically effective amount of a chemical compound identified by a process in accordance with this invention or a novel structural and functional analog or homolog thereof. In one embodiment, the mammalian SNORF33 receptor is a human SNORF33 receptor. In another embodiment, the mammalian SNORF33 receptor is a rat or a mouse SNORF33 receptor.

Thus, once the gene for a targeted receptor subtype is cloned, it is placed into a recipient cell which then expresses the targeted receptor subtype on its surface. This cell, which expresses a single population of the targeted human receptor subtype, is then propagated resulting in the establishment of a cell line. This cell line, which constitutes a drug discovery system, is used in two different types of assays: binding assays and functional assays. In binding assays, the affinity of a compound for both the receptor subtype that is the target of a particular drug discovery program and other receptor subtypes that could be associated with side effects are measured. These measurements enable one to predict the potency of a compound, as well as the degree of selectivity that the compound has for the targeted receptor subtype over other receptor subtypes. The data obtained from binding assays also enable chemists to design compounds toward or away from one or more of the relevant subtypes, as appropriate, for optimal therapeutic efficacy. In functional assays, the nature of the response of the receptor subtype to the compound is determined. Data from the functional assays show whether the compound is acting to inhibit or enhance the activity of the receptor subtype, thus enabling pharmacologists to evaluate compounds rapidly at their ultimate human receptor subtypes targets permitting chemists to rationally design drugs that will be more effective and have fewer or substantially less severe side effects than existing drugs.

Approaches to designing and synthesizing receptor subtype-selective compounds are well known and include traditional medicinal chemistry and the newer technology of combinatorial chemistry, both of which are supported by computer-assisted molecular modeling. With such approaches, chemists and pharmacologists use their knowledge of the structures of the targeted receptor subtype and compounds determined to bind and/or activate or inhibit activation of the receptor subtype to design and synthesize structures that will have activity at these receptor subtypes.

Combinatorial chemistry involves automated synthesis of a variety of novel compounds by assembling them using different combinations of chemical building blocks. The use of combinatorial chemistry greatly accelerates the process of generating compounds. The resulting arrays of compounds are called libraries and are used to screen for compounds ("lead compounds") that demonstrate a sufficient level of activity at receptors of interest. Using combinatorial chemistry it is possible to synthesize "focused" libraries of compounds anticipated to be highly biased toward the receptor target of interest.

Once lead compounds are identified, whether through the use of combinatorial chemistry or traditional medicinal chemistry or otherwise, a variety of homologs and analogs are prepared to facilitate an understanding of the relationship between chemical structure and biological or functional activity. These studies define structure activity relationships which are then used to design drugs with improved potency, selectivity and pharmacokinetic properties. Combinatorial chemistry is also used to rapidly generate a variety of structures for lead optimization. Traditional medicinal chemistry, which involves the synthesis of compounds one at a time, is also used for further refinement and to generate compounds not accessible by automated techniques. Once such drugs are defined the production is scaled up using standard chemical manufacturing methodologies utilized throughout the pharmaceutical and chemistry industry.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Materials and Methods

MOPAC (Mixed Oligonucleotide Primed Amplification of cDNA)

100 ng of rat genomic DNA (Clontech, Palo Alto, Calif.) was used for degenerate MOPAC PCR using Taq DNA polymerase (Boehringer-Mannheim, Indianapolis, Ind.) and the following degenerate oligonucleotides: BB726, designed based on an alignment of the sixth transmembrane domain of select serotonin (5-HT) receptors; and BB642, designed based on an alignment of the seventh transmembrane domain of the same serotonin receptors.

The conditions for the MOPAC PCR reaction were as follows: 5 minute hold at 94° C.; 10 cycles of 30 seconds at 94° C., 1 minute at 43° C., 1 minute 45 seconds at 72° C.; 30 cycles of 30 seconds at 94° C., 1 minute at 48° C., 1 minute 45 seconds at 72° C.; 20 minute hold at 72° C.; 4° C. hold until ready for agarose gel electrophoresis.

The products were run on a 1.5% agarose TAE gel and bands of the expected size (—150 bp) were cut from the gel, purified using the QIAQUICK gel extraction kit (QIAGEN, Chatsworth, Calif.), and subcloned into the TA cloning vector (Invitrogen, San Diego, Calif.). White (insert-containing) colonies were picked and subjected to PCR using pCR2.1 vector primers JAB1 and JAB2 using the Expand Long Template PCR System and the following protocol: 94° C. hold for 3 minutes; 35 cycles of 94° C. for 1 minute, 68° C. for 1 minute 15 seconds; 2 minute hold at 68° C., 4° C. hold until the products were ready for purification. PCR products were purified by isopropanol precipitation (10 µl PCR product, 18 µl low TE, 10.5 µl 2M NaClO$_4$, and 21.5 µl isopropanol) and sequenced using the ABI Big Dye cycle sequencing protocol and ABI 377 sequencers (ABI, Foster City, Calif.). Nucleotide and amino acid sequence analyses were performed using the Wisconsin Package (GCG, Genetics Computer Group, Madison, Wis.). One PCR product from rat genomic DNA (5-HT-38-rgen-051) was determined to be a novel G protein-coupled receptor-like sequence based on database searches and its homology to other known G protein-coupled receptors (—42-48% amino acid identity to 5HT$_4$, dopamine D$_2$ and β-adrenergic receptors). This novel sequence was designated SNORF33.

Cloning of the Full-Length Coding Sequence of Rat SNORF33

A rat liver genomic phage library (2.75 million recombinants, Stratagene, LaJolla, Calif.) was screened using a $^{32}$P-labeled oligonucleotide probe, HK132, designed against the rat SNORF33 fragment.

Hybridization of nitrocellulose filter overlays of the plates was performed at high stringency: 42° C. in a solution containing 50% formamide, 5× SSC (1× SSC is 0.15M sodium chloride, 0.015M sodium citrate), 1× Denhardt's solution (0.02% polyvinylpyrrolindone, 0.02% Ficoll, 0.02% bovine serum albumin), 7 mM Tris and 25 µg/ml sonicated salmon sperm DNA. The filters were washed at 55° C. in 0.1× SSC containing 0.1% sodium dodecyl sulfate and exposed at −70° C. to Kodak BioMax MS film in the presence of an intensifying screen.

A positive signal on plate 35 was isolated on a tertiary plating. A 5.5 kb fragment, from a BglII digest of DNA isolated from this positive, was identified by Southern blot analysis, subcloned into pcDNA3.1 (Invitrogen, San Diego, Calif.) and used to transform E. coli DH5α cells (Gibco BRL, Gaithersburg Md.). Plasmid DNA from one transformant, KO26, was sequenced on both strands using an ABI 377 sequencer as described above. Sequencing of KO26 revealed an open reading frame of 996 nucleotides with approximately 3.7 kb of upstream sequence and 0.8 kb of downstream sequence. A 1.8 kb EcoRI-HindIII fragment from KO26 was subcloned into pcDNA3.1. This construct, designated BO111, contains the 996 bp coding region as well as 81 nucleotides of 5' untranslated region and 791 bp of 3' untranslated region. This construct, BO111, has been renamed pcDNA3.1-rSNORF33-f. The full length SNORF33 was determined to have significant homology with PNR (38% amino acid identity), 5HT$_{1D}$, 5HT$_4$ and dopamine D$_1$ receptors (35-36% amino acid identities) and histamine H$_1$ and α$_{1c}$ adrenergic receptors (33% amino acid identity). There were no sequences in the Genbank databases (Genembl, STS, EST, GSS, or SwissProt) that were identical to SNORF33.

Isolation of a Fragment of the Human Homologue of SNORF33

To obtain a fragment of the human homologue of SNORF33, 100 ng of human genomic DNA (Clontech, Palo Alto, Calif.) was amplified with a forward PCR primer corresponding to TMI of the rat SNORF33 (BB990) and a reverse primer corresponding to TMVII of the rat SNORF33 (BB991). PCR was performed with the Expand Long Template PCR System (Boeringer Mannheim) under the following conditions: 30 seconds at 94° C., 1 minute at 47° C. or 51° C., 1.5 minutes at 68° C. for 40 cycles, with a pre- and post-incubation of 5 minutes at 94° C. and 7 minutes at 68° C. respectively. Bands of 833 bp from 2 independent PCR reactions were isolated from a TAE gel, purified using the QIAQUICK gel extraction kit (QIAGEN, Chatsworth, Calif.), and sequenced on both strands as described above. The sequence of these two PCR products were identical and were used to design forward and reverse PCR primers (BB997, also incorporating a BamHI restriction site, and BB998, also incorporating a HindIII site) which were used to amplify a band from human genomic DNA using the following conditions: 30 seconds at 94° C., 2 minute at 68° C. for 40 cycles, with a pre- and post-incubation of 5 minutes at 94° C. and 7 minutes at 68° C., respectively. Products from 6 independent PCR reactions were digested with EcoRI and BamHI, and fragments of 590 bp were gel-purified and ligated into pcDNA3.1 (Invitrogen, San Diego, Calif.). One transformant from each PCR reaction was sequenced as above, and a consensus sequence determined. The nucleotide sequence of one product, KO28, was identical to the consensus. This construct has been renamed pcDNA3.1-hSNORF33-p.

Isolation of the Full-Length Human SNORF33 Receptor cDNA

A nucleic acid sequence encoding a human SNORF33 receptor cDNA may be isolated using standard molecular biology techniques and approaches such as those described below:

Approach #1: A human genomic library (e.g., cosmid, phage, P1, BAC, YAC) may be screened with a $^{32}$P-labeled oligonucleotide probe corresponding to the human fragment whose sequence is shown in FIG. 1 to isolate a genomic clone. The full-length sequence may be obtained by sequencing this genomic clone. If one or more introns are present in the gene, the full-length intronless gene may be obtained from cDNA using standard molecular biology techniques. For example, a forward PCR primer designed in the 5'UT and a reverse PCR primer designed in the 3'UT may be used to amplify a full-length, intronless receptor from cDNA. Standard molecular biology techniques could be used to subclone this gene into a mammalian expression vector.

Approach #2: Standard molecular biology techniques may be used to screen commercial cDNA phage libraries by hybridization under high stringency with a $^{32}$P-labeled oligonucleotide probe corresponding to the human fragment whose sequence is shown in FIG. 1. One may isolate a full-length human SNORF33 receptor by obtaining a plaque purified clone from the lambda libraries and then subjecting the clone to direct DNA sequencing. Alternatively, standard molecular biology techniques could be used to screen human cDNA plasmid libraries by PCR amplification of library pools using primers designed against the partial human sequence. A full-length clone may be isolated by Southern hybridization of colony lifts of positive pools with a $^{32}$P-oligonucleotide probe.

Approach #3: 3' and 5' RACE may be utilized to generate PCR products from cDNA expressing SNORF33 which contain the additional sequence of SNORF33. These RACE PCR products may then be sequenced to determine the additional sequence. This new sequence is then used to design a forward PCR primer in the 5'UT and a reverse primer in the 3'UT. These primers are then used to amplify a full-length SNORF33 clone from cDNA.

Cloning of the Full-Length Human SNORF33

5' and 3' RACE

To isolate the full-length human SNORF33, we chose approach #3 described above. Specifically, we utilized the Clontech Marathon cDNA Amplification kit (Clontech, Palo Alto, Calif.) for 5'/3' Rapid Amplification of cDNA ends (RACE). Nested PCR were performed according to the Marathon cDNA Amplification protocol using Marathon-Ready human kidney and stomach cDNA (Clontech). For 5'RACE, the initial PCR was performed with the supplier's Adapter Primer 1 and BB1049, a reverse primer from TMIII of the PCR fragment described above. One μl of this initial PCR reaction was re-amplified using the Adaptor Primer 2 and BB1021, a reverse primer from TMII. PCR was performed with Advantage Klentaq Polymerase (Clontech, Palo Alto, Calif.) under the following conditions: 5 minutes at 94° C.; 5 cycles of 94° C. for 30 seconds and 72° C. (initial PCR) or 70° C. (nested PCR) for 2 minutes; 5 cycles of 94° C. for 30 seconds and 70° C. (initial PCR) or 68° C. (nested PCR) for 2 minutes; 25 cycles (initial PCR) or 18 cycles (nested PCR) of 94° C. for 30 seconds and 68° C. (initial PCR) or 66° C. (nested PCR) for 2 minutes; 68° C. hold for 7 minutes, and 4° C. hold until the products were ready for analysis. For 3'RACE, the initial PCR was performed with the supplier's Adapter Primer 1 and BB1050, a forward primer from the V-VI loop of the PCR fragment described above. Two μls Of this initial PCR reaction was re-amplified using the Adaptor Primer 2 and BB1022, a forward PCR primer from TMVI.

PCR was performed with the Expand Long Template PCR System (Roche Molecular Biochemicals, Indianapolis, Ind.) under the following conditions: 5 minutes at 94° C.; 5 cycles of 94° C. for 30 seconds, 72° C. (initial PCR) or 70° C. (nested PCR) for 45 seconds, 68° C. for 2 minutes; 5 cycles of 94° C. for 30 seconds, 70° C. (initial PCR) or 68° C. (nested PCR) for 45 seconds and 68° C. for 2 minutes; 25 cycles (initial PCR) or 18 cycles (nested PCR) of 94° C. for 30 seconds and 68° C. (initial PCR) or 66° C. (nested PCR) for 45 seconds and 68° C. for 2 minutes; 68° C. hold for 7 minutes, and 4° C. hold until the products were ready for analysis. A 300 bp and a 500 bp fragment from the 5' RACE and a 350 bp fragment from the 3' RACE were isolated from a 1% agarose TAE gel using the QIAQUICK kit and sequenced using ABI 377 sequencers and BigDye termination cycle sequencing as described above. Sequences were analyzed using the Wisconsin Package (GCG, Genetics Computer Group, Madison, Wis.).

Isolation of a Full-Length Human SNORF33 Clone

After determining the full-length coding sequence of this receptor sequence, the entire coding region was amplified from human genomic DNA and human amygdala cDNA using the Expand Long Template PCR system (Roche Molecular Biochemicals, Indianapolis, Ind.). The primers for this reaction were specific to the 5' and 3' untranslated regions of SNORF33 with BamHI and HindIII restriction sites incorporated into the 5' ends of the 5' (BB1101) and 3' (BB1102) primers, respectively. The products from 7 independent PCR reactions were then digested with BamHI and HindIII, subcloned into the BamHI and HindIII sites of the expression vector pcDNA3.1 (−), and sequenced in both directions using vector- and gene-specific primers. One construct, GEN-p1c4, matched the consensus and was renamed BO113. This receptor/expression vector construct of human SNORF33 in pcDNA3.1(−) was named pcDNA3.1-hSNORF33-f. A BamHI/HindIII fragment of BO113, containing the entire SNORF33 insert, was ligated into BamHI/HindIII digested pEXJ.RHT3T7 vector. This construct, BO114, was named pEXJ-hSNORF33-f.

Isolation of a Fragment of the Mouse Homologue of SNORF33

Figure 18:
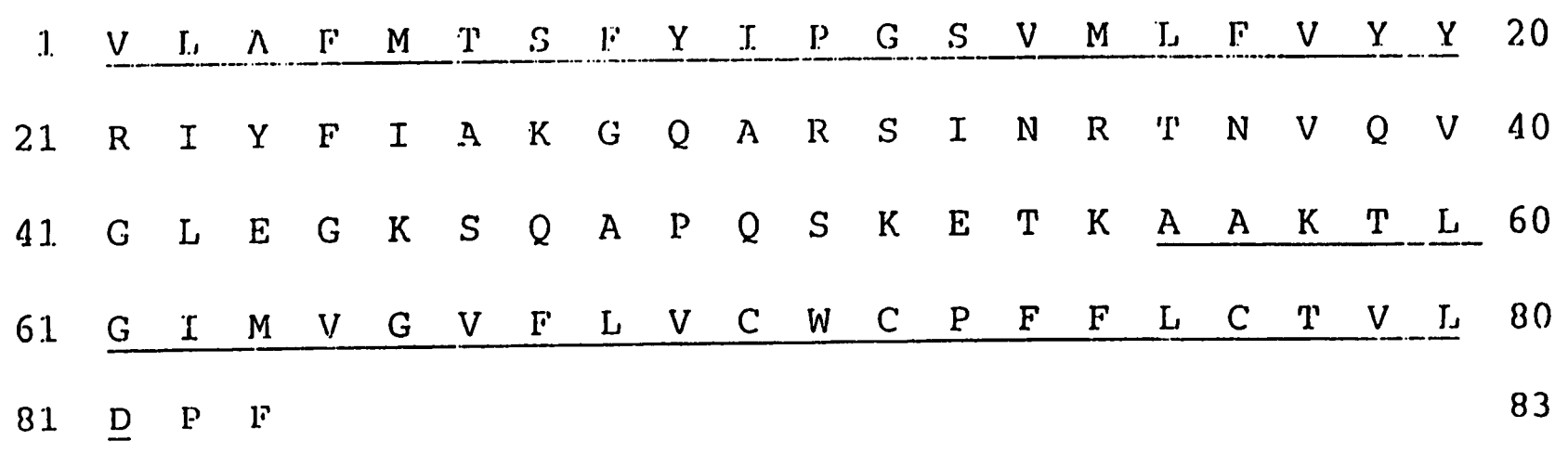

To obtain a fragment of the mouse homologue of SNORF33, 100 ng of mouse genomic DNA (Clontech, Palo Alto, Calif.) was amplified with a forward PCR primer corresponding to TMI of the rat SNORF33 (BB982) and a reverse primer corresponding to TMVII of the rat SNORF33 (BB983). PCR was performed with the Expand Long Template PCR System (Boeringer Mannheim) under the following conditions: 30 seconds at 94° C., 45 seconds at 45 to 51° C., 2 minutes at 68° C. for 37 cycles, with a pre- and post-incubation of 5 minutes at 95° C. and 7 minutes at 68° C. respectively. Bands of 800 bp from 7 independent PCR reactions were isolated from a TAE gel, purified using the QIAQUICK gel extraction kit (QIAGEN, Chatsworth, Calif.), and sequenced on both strands as described above. A consensus sequence was determined for these seven products, and was used to design forward and reverse PCR primers (BB1273, also incorporating a BamHI restriction site, and BB1274, also incorporating a HindIII site) which were used to amplify a band from mouse genomic DNA using the following conditions: 30 seconds at 94° C., 1.5 minutes at 68° C. for 32 cycles, with a pre- and post-incubation of 5 minutes at 94° C. and 7 minutes at 68° C., respectively. Products from 4 independent PCR reactions were digested with BamHI and HindIII, and fragments of 252 bp were gel-purified and ligated into pEXJ.T3T7. One transformant from each PCR reaction was sequenced as above, and all four sequences were determined to be identical. The nucleotide and amino acid sequences of one product, KO94, are shown in FIGS. 17 and 18, respectively. KO94 was renamed pEXJ.T3T7-mS-NORF33-p. It is anticipated that a molecular biologist skilled in the art may isolate the full-length mouse SNORF33 receptor using standard molecular biology techniques and approaches such as those briefly described below:

Approach #1: Pools of in-house mouse cDNA plasmid libraries may be screened by high stringency PCR with primers designed against the mouse SNORF33 partial sequence. Positive pools could be sib-selected and then colonies from a low complexity subpool could be screened by filter hybridization using an oligonucleotide probe designed against the mouse SNORF33 fragment.

Approach #2: Standard molecular biology techniques could be used to screen commercial phage cDNA or genomic libraries by filter hybridization under high stringency conditions using an oligonucleotide probe designed against the mouse SNORF33 fragment.

Approach #3: As yet another alternative method, one could utilize 5' and 3' RACE to generate PCR products from mouse cDNA expressing mouse SNORF33 which would contain the additional 5' and 3' sequences of this receptor. For example, Marathon-Ready cDNA (Clontech, Palo Alto, Calif.) could be used as instructed by the manufacturer. Nested reverse PCR primers designed against the mouse SNORF33 fragment could be used for 5' RACE and nested forward PCR primers could be used for 3' RACE. Using this new sequence, a forward PCR primer designed in the 5' untranslated region and a reverse PCR primer designed in the 3' untranslated region could be used to amplify a full-length SNORF33 receptor cDNA from either genomic DNA or mouse tissue cDNA.

Oligonucleotide primers and probes used in the identification and isolation of SNORF33:

```
JAB1:   5'-TTATGCTTCCGGCTCGTATGTTGT   (SEQ ID No: 7)
        G-3'

JAB2:   5'-ATGTGCTGCAAGGCGATTAAGTTG   (SEQ ID No: 8)
        GG-3'

BB726   5'-TNNKNTGYTGGYTNCCNTTYTTY-  (SEQ ID No: 9)
        3'

BB642   5'-ARNSWRTTNVNRTANCCNARCC-    (SEQ ID No: 10)
        3'

HK132   5'-TTCTGCATGGTCCTGGACCCTTTC   (SEQ ID No: 11)
        CTGGGCTATGTTATCCCACCCACTCTG
        AATGACACACTG-3'

BB990   5'-CATAATTCTAACCACTCTGGTTG    (SEQ ID No: 12)
        G-3'

BB991   5'-CTGAACCAGGGATAGAAAAAGG     (SEQ ID No: 13)
        C-3'

BB997   5'-TCCGTAGGATCCAATTGGCTCATT   (SEQ ID No: 14)
        CATTCCATGGCC-3'

BB998   5'-AGCTACAAGCTTGCACCAGCATAT   (SEQ ID No: 15)
        TAGGAAAACTCC-3'

BB1049  5'-CAGCATAATGTCGGTGCTTGTGT    (SEQ ID No: 16)
        G-3'

BB1021  5'-TACTGTAAGGCATGACCAGACAC    (SEQ ID No: 17)
        C-3'

BB1050  5'-ATTAGTGATGCCAATCAGAAGCTC   (SEQ ID No: 18)
        C-3'

BB1022  5'-GAAAGGAAAGCTGTGAAGACATTG   (SEQ ID No: 19)
        G-3'

BB1101  5'-GATCTAGGATCCGGAAAAGTAAAC   (SEQ ID No: 20)
        TGATTGACAGCCC-3'

BB1102  5'-CTAGCTAAGCTTGATCATCAACCG   (SEQ ID No: 21)
        ATTTGCAAAACAG-3'

BB982   5'-ACTCTGGTTGGCAACTTAATAGT-   (SEQ ID No: 32)
        3'

BB983   5'-GCATAAACCATCGGGTTGAAGGC-   (SEQ ID No: 33)
        3'

BB1273  5'-TATCGCGGATCCGGTACTGGCGTT   (SEQ ID No: 34)
        CATGACTTCCTTC-3

BB1274  5'-CCAGCTAAGCTTAGGAAAGGGTCC   (SEQ ID No: 35)
        AGGACCGTGCAG-3'
```

Cloning of the Full-Length Mouse SNORF33 3' RACE

To determine the 3' coding sequence of mouse SNORF33, we utilized the Clontech Marathon cDNA Amplification kit (Clontech, Palo Alto, Calif.) for 5'/3' Rapid Amplification of cDNA ends (RACE). Nested PCR was performed according to the Marathon cDNA Amplification protocol using Marathon-Ready mouse brain cDNA (Clontech, Palo Alto, Calif.). The initial PCR was performed with the supplier's Adapter Primer 1 and BB1296, a forward primer from TMVI of the PCR fragment described above. Two µl of this initial PCR reaction was re-amplified using the Adaptor Primer 2 and BB1297, a forward primer from the third extracellular loop and the TMVII. PCR was performed with Advantage Klentaq Polymerase (Clontech, Palo Alto, Calif.) under the following conditions: 5 minutes at 95° C.; 5 cycles of 94° C. for 30 seconds and 72° C. for 3 minutes; 5 cycles of 94° C. for 30 seconds and 70° C. for 3 minutes; 25 cycles (initial PCR) or 18 cycles (nested PCR) of 94° C. for 30 seconds and 68° C. for 3 minutes; 68° C. hold for 7 minutes, and 4° C. hold until the products were ready for analysis. A 900 bp fragment was isolated from an agarose TAE gel using the QIAQUICK kit and sequenced using ABI 377 sequencers and BigDye termination cycle sequencing as described above. Sequences were analyzed using the Wisconsin Package (GCG, Genetics Computer Group, Madison, Wis.).

Reduced Stringency PCR for 5' End

The 5' coding sequence of mouse SNORF33 was determined by amplifying mouse genomic DNA under reduced stringency with BB1301, a forward primer from the 5' untranslated region of rat SNORF33, and BB1295, a reverse primer from TM2 of the mouse SNORF33 fragment. PCR was performed with the Expand Long Template PCR system (Roche Molecular Biochemicals, Indianapolis, Ind.) under the following conditions: 5 minutes at 94° C.; 40 cycles of 94° C. for 30 seconds, 45-50.5° C. for 45 seconds, and 68° C. for 1.5 minutes; 68° C. hold for 7 minutes, and 4° C. hold until the products were ready for analysis. A 300 bp fragment was isolated from an agarose TAE gel using the QIAQUICK kit and sequenced using ABI 377 sequencers and BigDye termination cycle sequencing as described above. Sequences were analyzed using the Wisconsin Package (GCG, Genetics Computer Group, Madison, Wis.).

Isolation of a Full-Length Mouse SNORF33 Clone

After determining the full-length coding sequence of this receptor, the entire coding region was amplified from mouse genomic DNA (Clontech, Palo Alto, Calif.) using the Expand Long Template PCR system (Roche Molecular Biochemicals, Indianapolis, Ind.). The primers for this reaction were BB1307, a forward primer from the 5' untranslated region also incorporating a BamHI restriction site, and BB1308, a reverse primer specific to the 3' untranslated region. Conditions for PCR were as follows: 5 minutes at 95° C.; 32 cycles of 94° C. for 30 seconds and 68° C. for 1.5 minutes; 68° C. hold for 7 minutes, and 4° C. hold until the products were ready for analysis. The products from 6 independent PCR reactions were then digested with BamHI and XbaI, subcloned into the expression vector pEXJ and sequenced in both directions. One construct, KO114, matched the consensus and was renamed BO131. This receptor/expression vector construct of mouse SNORF33 in pEXJ was named pEXJ-mSNORF33-f.

Oligonucleotide Primers

The following is a list of primers and their associated sequences which were used in the cloning of this receptor:

```
BB1295  5'-GCTGCAGGGCATTATCAGACAGC      (SEQ ID NO: 38)
        C-3'

BB1296  5'-TCTGCACGGTCCTGGACCCTTTC      (SEQ ID NO: 39)
        C-3'

BB1297  5'-TATCCCACCCTCTCTGAATGACG      (SEQ ID NO: 40)
        C-3'

BB1301  5'-CTGGAGAAGCATTGCTCGACAGC      (SEQ ID NO: 41)
        C-3'

BB1307  5'-GTCATCGGATCCGCCCAGCCTGT      (SEQ ID NO: 42)
        GTCTAGTTCTC-3'

BB1308  5'-TCAGCTTCTAGAGGGTTGCTGGG      (SEQ ID NO: 43)
        AATTGAACTCAGG-3'
```

Isolation of Other Species Homologs of SNORF33 Receptor cDNA

A nucleic acid sequence encoding a SNORF33 receptor cDNA from other species may be isolated using standard molecular biology techniques and approaches such as those described below:

Approach #1: A genomic library (e.g., cosmid, phage, P1, BAC, YAC) generated from the species of interest may be screened with a $^{32}$P-labeled oligonucleotide probe corresponding to a fragment of the human or rat SNORF33 receptors whose sequence is shown in FIGS. 1, 3A-3B and 5A-5B to isolate a genomic clone. The full-length sequence may be obtained by sequencing this genomic clone. If one or more introns are present in the gene, the full-length intronless gene may be obtained from cDNA using standard molecular biology techniques. For example, a forward PCR primer designed in the 5'UT and a reverse PCR primer designed in the 3'UT may be used to amplify a full-length, intronless receptor from cDNA. Standard molecular biology techniques could be used to subclone this gene into a mammalian expression vector.

Approach #2: Standard molecular biology techniques may be used to screen commercial cDNA phage libraries of the species of interest by hybridization under reduced stringency with a $^{32}$P-labeled oligonucleotide probe corresponding to a fragment of the sequences shown in FIGS. 1, 3A-3B, or 5A-5B. One may isolate a full-length SNORF33 receptor by obtaining a plaque purified clone from the lambda libraries and then subjecting the clone to direct DNA sequencing. Alternatively, standard molecular biology techniques could be used to screen cDNA plasmid libraries by PCR amplification of library pools using primers designed against a partial species homolog sequence. A full-length clone may be isolated by Southern hybridization of colony lifts of positive pools with a $^{32}$P-oligonucleotide probe.

Approach #3: 3' and 5' RACE may be utilized to generate PCR products from cDNA derived from the species of interest expressing SNORF33 which contain the additional sequence of SNORF33. These RACE PCR products may then be sequenced to determine the additional sequence. This new sequence is then used to design a forward PCR primer in the 5'UT and a reverse primer in the 3'UT. These primers are then used to amplify a full-length SNORF33 clone from cDNA.

Examples of other species include, but are not limited to, dog, monkey, hamster and guinea pig.

Host Cells

A broad variety of host cells can be used to study heterologously expressed proteins. These cells include but are not limited to mammalian cell lines such as; COS-7, CHO, LM(tk$^-$), HEK293, etc.; insect cell lines such as; Sf9, Sf21, etc.; amphibian cells such as *Xenopus* oocytes; assorted yeast strains; assorted bacterial cell strains; and others. Culture conditions for each of these cell types is specific and is known to those familiar with the art.

Transient Expression

DNA encoding proteins to be studied can be transiently expressed in a variety of mammalian, insect, amphibian, yeast, bacterial and other cells lines by several transfection methods including but not limited to; calcium phosphate-mediated, DEAE-dextran mediated; liposomal-mediated, viral-mediated, electroporation-mediated, and microinjection delivery. Each of these methods may require optimization of assorted experimental parameters depending on the DNA, cell line, and the type of assay to be subsequently employed.

Stable Expression

Heterologous DNA can be stably incorporated into host cells, causing the cell to perpetually express a foreign protein. Methods for the delivery of the DNA into the cell are similar to those described above for transient expression but require the co-transfection of an ancillary gene to confer drug resistance on the targeted host cell. The ensuing drug resistance can be exploited to select and maintain cells that have taken up the DNA. An assortment of resistance genes are available including but not restricted to neomycin, kanamycin, and hygromycin. For the purposes of studies concerning the receptor of this invention, stable expression of a heterologous receptor protein is typically is carried out in, mammalian cells including but not necessarily restricted to, CHO, HEK293, LM(tk-), etc.

In addition native cell lines that naturally carry and express the nucleic acid sequences for the receptor may be used without the need to engineer the receptor complement.

Functional Assays

Cells expressing the receptor DNA of this invention may be used to screen for ligands to said receptor using functional assays. Once a ligand is identified the same assays may be used to identify agonists or antagonists of the receptor that may be employed for a variety of therapeutic purposes. It is well known to those in the art that the over-expression of a G protein-coupled receptor can result in the constitutive activation of intracellular signaling pathways. In the same manner, over-expression of the receptor in any cell line as described above, can result in the activation of the functional responses described below, and any of the assays herein described can be used to screen for agonist, partial agonist, inverse agonist, and antagonist ligands of the SNORF33 receptor.

A wide spectrum of assays can be employed to screen for the presence of receptor rSNORF33 ligands. These assays range from traditional measurements of total inositol phosphate accumulation, cAMP levels, intracellular calcium mobilization, and potassium currents, for example; to systems measuring these same second messengers but which have been modified or adapted to be of higher throughput, more generic and more sensitive; to cell based assays reporting more general cellular events resulting from receptor activation such as metabolic changes, differentiation, cell division/proliferation. Description of several such assays follow.

Cyclic AMP (cAMP) Assay

The receptor-mediated stimulation or inhibition of cyclic AMP (cAMP) formation may be assayed in cells expressing the mammalian receptors. Cells are plated in 96-well plates or other vessels and preincubated in a buffer such as HEPES buffered saline (NaCl (150 mM), $CaCl_2$ (1 mM), KCl (5 mM), glucose (10 mM)) supplemented with a phosphodiesterase inhibitor such as 5 mM theophylline, with or without protease inhibitor cocktail (For example, a typical inhibitor cocktail contains 2 µg/ml aprotinin, 0.5 mg/ml leupeptin, and 10 µg/ml phosphoramidon.) for 20 min at 37° C., in 5% $CO_2$. Test compounds are added with or without 10 mM forskolin and incubated for an additional 10 min at 37° C. The medium is then aspirated and the reaction stopped by the addition of 100 mM HCl or other methods. The plates are stored at 4° C. for 15 min, and the cAMP content in the stopping solution is measured by radioimmunoassay. Radioactivity may be quantified using a gamma counter equipped with data reduction software. Specific modifications may be performed to optimize the assay for the receptor or to alter the detection method of cAMP.

COS-7 cells were transiently transfected with rSNORF33 gene using the calcium phosphate method and plated in 96-well plates. 48 hours after transfection, cells were washed twice with Dulbecco's phosphate buffered saline (PBS) supplemented with 10 mM HEPES, 10 mM glucose, 5 mM theophylline and 10 µM pargyline and were incubated in the same buffer for 20 min at 37° C., in 95% $O_2$ and 5% $CO_2$. Test compounds were added and cells were incubated for an additional 10 min at 37° C. The medium was then aspirated and the reaction stopped by the addition of 100 mM HCl. The plates were stored at −20° C. for 2-5 days. For cAMP measurement, plates were thawed and the cAMP content in each well was measured by radioimmunoassay cAMP Scintillation Proximity Assay (Amersham Pharmacia Biotech). Radioactivity was quantified using microbeta Trilux counter (Wallac).

Arachidonic Acid Release Assay

Cells expressing the receptor are seeded into 96 well plates or other vessels and grown for 3 days in medium with supplements. $^3$H-arachidonic acid (specific activity=0.75 µCi/ml) is delivered as a 100 µL aliquot to each well and samples are incubated at 37° C., 5% $CO_2$ for 18 hours. The labeled cells are washed three times with medium. The wells are then filled with medium and the assay is initiated with the addition of test compounds or buffer in a total volume of 250 µL. Cells are incubated for 30 min at 37° C., 5% $CO_2$. Supernatants are transferred to a microtiter plate and evaporated to dryness at 75° C. in a vacuum oven. Samples are then dissolved and resuspended in 25 µL distilled water. Scintillant (300 µL) is added to each well and samples are counted for $^3$H in a Trilux plate reader. Data are analyzed using nonlinear regression and statistical techniques available in the GraphPAD Prism package (San Diego, Calif.).

Intracellular Calcium Mobilization Assays

The intracellular free calcium concentration may be measured by microspectrofluorimetry using the fluorescent indicator dye Fura-2/AM (Bush et al, 1991). Cells expressing the receptor are seeded onto a 35 mm culture dish containing a glass coverslip insert and allowed to adhere overnight. Cells are then washed with HBS and loaded with 100 µL of Fura-2/AM (10 µM) for 20 to 40 min. After washing with HBS to remove the Fura-2/AM solution, cells are equilibrated in HBS for 10 to 20 min. Cells are then visualized under the 40× objective of a Leitz Fluovert FS microscope and fluorescence emission is determined at 510 nM with excitation wavelengths alternating between 340 nM and 380 nM. Raw fluorescence data are converted to calcium concentrations using standard calcium concentration curves and software analysis techniques.

In another method, the measurement of intracellular calcium can also be performed on a 96-well (or higher) format and with alternative calcium-sensitive indicators, preferred examples of these are: aequorin, Fluo-3, Fluo-4, Fluo-5, Calcium Green-1, Oregon Green, and 488 BAPTA. After activation of the receptors with agonist ligands the emission elicited by the change of intracellular calcium concentration can be measured by a luminometer, or a fluorescence imager; a preferred example of this is the fluorescence imager plate reader (FLIPR).

Cells expressing the receptor of interest are plated into clear, flat-bottom, black-wall 96-well plates (Costar) at a density of 30,000-80,000 cells per well and allowed to incubate over night at 5% $CO_2$, 37° C. The growth medium is aspirated and 100 µL of dye loading medium is added to each well. The loading medium contains: Hank's BSS (without phenol red)(Gibco), 20 mM HEPES (Sigma), 0.1% BSA (Sigma), dye/pluronic acid mixture (e.g. 1 mM Flou-3, AM (Molecular Probes), 10% pluronic acid (Molecular Probes); (mixed immediately before use), and 2.5 mM probenecid (Sigma)(prepared fresh)). The cells are allowed to incubate for about 1 hour at 5% $CO_2$, 37° C.

During the dye loading incubation the compound plate is prepared. The compounds are diluted in wash buffer (Hank's BSS without phenol red), 20 mM HEPES, 2.5 mM probenecid to a 3× final concentration and aliquoted into a clear v-bottom plate (Nunc). Following the incubation the cells are washed to remove the excess dye. A Denley plate washer is used to gently wash the cells 4 times and leave a 100 µL final volume of wash buffer in each well. The cell plate is placed in the center tray and the compound plate is placed in the right tray of the FLIPR. The FLIPR software is setup for the experiment, the experiment is run and the data are collected. The data are then analyzed using an excel spreadsheet program.

Antagonist ligands are identified by the inhibition of the signal elicited by agonist ligands.

In another method, intracellular free calcium concentration may be measured by the fluorescence imager plate reader (FLIPR). Cells expressing the receptor of interest are plated into clear, flat-bottom, black-wall 96-well plates (Costar) at a density of 80,000-150,000 cells per well and allowed to incubate for 48 hr at 95% $O_2$/5% $CO_2$, 37° C. The growth medium is aspirated and 100 µl of loading medium containing fluo-3 dye is added to each well. The loading medium contains: Hank's BSS (without phenol red)(Gibco), 20 mM HEPES (Sigma), 0.1 or 1% BSA (Sigma), dye/pluronic acid mixture (e.g. 1 mM Flou-3, AM (Molecular Probes) and 10% pluronic acid (Molecular Probes) mixed immediately before use), and 2.5 mM probenecid (Sigma)(prepared fresh). The cells are allowed to incubate for about 1 hour at 95% $O_2$/5% $CO_2$, 37° C.

During the dye loading incubation the compound plate is prepared. The compounds are diluted in wash buffer (Hank's BSS (without phenol red), 20 mM HEPES, 2.5 mM probenecid) to a 4× final concentration and aliquoted into a clear v-bottom plate (Nunc). Following the incubation the cells are washed to remove the excess dye. A Denley plate washer is used to gently wash the cells 4 times and leave a 100 µl final volume of wash buffer in each well. The cell plate is placed in the center tray and the compound plate is placed in the right tray of the FLIPR. The FLIPR software is setup for the experiment, the experiment is run and the data are collected. The data are then analyzed using an excel spreadsheet program.

Inositol Phosphate Assay

Receptor mediated activation of the inositol phosphate (IP) second messenger pathways may be assessed by radiometric or other measurement of IP products.

For example, in a 96 well microplate format assay, cells are plated at a density of 70,000 cells per well and allowed to incubate for 24 hours. The cells are then labeled with 0.5 µCi [$^3$H]myo-inositol overnight at 37° C., 5% $CO_2$. Immediately before the assay, the medium is removed and replaced with 90 µL of PBS containing 10 mM LiCl. The plates are then incubated for 15 min at 37° C., 5% $CO_2$. Following the incubation, the cells are challenged with agonist (10 ml/well; 10× concentration) for 30 min at 37° C., 5% $CO_2$. The challenge is terminated by the addition of 100 µL of 50% v/v trichloroacetic acid, followed by incubation at 4° C. for greater than 30 minutes. Total IPs are isolated from the lysate by ion exchange chromatography. Briefly, the lysed contents of the wells are transferred to a Multiscreen HV filter plate (Millipore) containing Dowex AG1-X8 (200-400 mesh, formate form). The filter plates are prepared adding 100 µL of Dowex AG1-X8 suspension (50% v/v, water:resin) to each well. The filter plates are placed on a vacuum manifold to wash or elute the resin bed. Each well is first washed 2 times with 200 µl of 5 mM myo-inositol. Total [$^3$H]-inositol phosphate is eluted with 75 µl of 1.2M ammonium formate/0.1M formic acid solution into 96-well plates. 200 µL of scintillation cocktail is added to each well, and the radioactivity is determined by liquid scintillation counting.

GTPγS Functional Assay

Membranes from cells expressing the receptor are suspended in assay buffer (e.g., 50 mM Tris, 100 mM NaCl, 5 mM $MgCl_2$, 10 µM GDP, pH 7.4) with or without protease inhibitors (e.g., 0.1% bacitracin). Membranes are incubated on ice for 20 minutes, transferred to a 96-well Millipore microtiter GF/C filter plate and mixed with GTPγ$^{35}$S (e.g., 250,000 cpm/sample, specific activity —1000 Ci/mmol) plus or minus unlabeled GTPγS (final concentration=100 µM). Final membrane protein concentration≈90 µg/ml. Samples are incubated in the presence or absence of test compounds for 30 min. at room temperature, then filtered on a Millipore vacuum manifold and washed three times with cold (4° C.) assay buffer. Samples collected in the filter plate are treated with scintillant and counted for $^{35}$S in a Trilux (Wallac) liquid scintillation counter. It is expected that optimal results are obtained when the receptor membrane preparation is derived from an appropriately engineered heterologous expression system, i.e., expression system resulting in high levels of expression of the receptor and/or expressing G-proteins having high turnover rates (for the exchange of GDP for GTP). GTPγS assays are well-known to those skilled in the art, and it is contemplated that variations on the method described above, such as are described by Tian et al. (1994) or Lazareno and Birdsall (1993), may be used.

Microphysiometric Assay

Because cellular metabolism is intricately involved in a broad range of cellular events (including receptor activation of multiple messenger pathways), the use of microphysiometric measurements of cell metabolism can in principle provide a generic assay of cellular activity arising from the activation of any receptor regardless of the specifics of the receptor's signaling pathway.

General guidelines for transient receptor expression, cell preparation and microphysiometric recording are described elsewhere (Salon, J. A. and Owicki, J. A., 1996). Typically cells expressing receptors are harvested and seeded at 3×10$^5$ cells per microphysiometer capsule in complete media 24 hours prior to an experiment. The media is replaced with serum free media 16 hours prior to recording to minimize non-specific metabolic stimulation by assorted and ill-defined serum factors. On the day of the experiment the cell capsules are transferred to the microphysiometer and allowed to equilibrate in recording media (low buffer RPMI 1640, no bicarbonate, no serum (Molecular Devices Corporation, Sunnyvale, Calif.) containing 0.1% fatty acid free BSA), during which a baseline measurement of basal metabolic activity is established.

A standard recording protocol specifies a 100 µl/min flow rate, with a 2 min total pump cycle which includes a 30 sec flow interruption during which the acidification rate measurement is taken. Ligand challenges involve a 1 min 20 sec exposure to the sample just prior to the first post challenge rate measurement being taken, followed by two additional pump cycles for a total of 5 min 20 sec sample exposure. Typically, drugs in a primary screen are presented to the cells at 10 µM final concentration. Follow up experiments to examine dose-dependency of active compounds are then done by sequentially challenging the cells with a drug concentration range that exceeds the amount needed to generate responses ranging from threshold to maximal levels. Ligand samples are then washed out and the acidification rates reported are expressed as a percentage increase of the peak response over the baseline rate observed just prior to challenge.

MAP Kinase Assay

MAP kinase (mitogen activated kinase) may be monitored to evaluate receptor activation. MAP kinase is activated by multiple pathways in the cell. A primary mode of activation involves the ras/raf/MEK/MAP kinase pathway. Growth factor (tyrosine kinase) receptors feed into this pathway via SHC/Grb-2/SOS/ras. Gi coupled receptors are also known to activate ras and subsequently produce an activation of MAP kinase. Receptors that activate phospholipase C (such as Gq/G11-coupled) produce diacylglycerol (DAG) as a consequence of phosphatidyl inositol hydrolysis. DAG activates protein kinase C which in turn phosphorylates MAP kinase.

MAP kinase activation can be detected by several approaches. One approach is based on an evaluation of the phosphorylation state, either unphosphorylated (inactive) or phosphorylated (active). The phosphorylated protein has a slower mobility in SDS-PAGE and can therefore be compared with the unstimulated protein using Western blotting. Alternatively, antibodies specific for the phosphorylated protein are available (New England Biolabs) which can be used to detect an increase in the phosphorylated kinase. In either method, cells are stimulated with the test compound and then extracted with Laemmli buffer. The soluble fraction is applied to an SDS-PAGE gel and proteins are transferred electrophoretically to nitrocellulose or Immobilon. Immunoreactive bands are detected by standard Western blotting technique. Visible or chemiluminescent signals are recorded on film and may be quantified by densitometry.

Another approach is based on evaluation of the MAP kinase activity via a phosphorylation assay. Cells are stimulated with the test compound and a soluble extract is prepared. The extract is incubated at 30° C. for 10 min with gamma-$^{32}$P-ATP, an ATP regenerating system, and a specific substrate for MAP kinase such as phosphorylated heat and acid stable protein regulated by insulin, or PHAS-I. The reaction is terminated by the addition of $H_3PO_4$ and samples are transferred to ice. An aliquot is spotted onto Whatman P81 chromatography paper, which retains the phosphorylated protein. The chromatography paper is washed and counted for $^{32}$P in a liquid scintillation counter. Alternatively, the cell extract is incubated with gamma-$^{32}$P-ATP, an ATP regenerating system, and biotinylated myelin basic protein bound by streptavidin to a filter support. The myelin basic protein is a substrate for activated MAP kinase. The phosphorylation reaction is carried out for 10 min at 30° C. The extract can then by aspirated through the filter, which retains the phosphorylated myelin basic protein. The filter is washed and counted for $^{32}$P by liquid scintillation counting.

Cell Proliferation Assay

Receptor activation of the receptor may lead to a mitogenic or proliferative response which can be monitored via $^3$H-thymidine uptake. When cultured cells are incubated with $^3$H-thymidine, the thymidine translocates into the nuclei where it is phosphorylated to thymidine triphosphate. The nucleotide triphosphate is then incorporated into the cellular DNA at a rate that is proportional to the rate of cell growth. Typically, cells are grown in culture for 1-3 days. Cells are forced into quiescence by the removal of serum for 24 hrs. A mitogenic agent is then added to the media. Twenty-four hours later, the cells are incubated with $^3$H-thymidine at specific activities ranging from 1 to 10 µCi/ml for 2-6 hrs. Harvesting procedures may involve trypsinization and trapping of cells by filtration over GF/C filters with or without a prior incubation in TCA to extract soluble thymidine. The filters are processed with scintillant and counted for $^3$H by liquid scintillation counting. Alternatively, adherent cells are fixed in MeOH or TCA, washed in water, and solubilized in 0.05% deoxycholate/0.1 N NaOH. The soluble extract is transferred to scintillation vials and counted for $^3$H by liquid scintillation counting.

Alternatively, cell proliferation can be assayed by measuring the expression of an endogenous or heterologous gene product, expressed by the cell line used to transfect the receptor, which can be detected by methods such as, but not limited to, florescence intensity, enzymatic activity, immunoreactivity, DNA hybridization, polymerase chain reaction, etc.

Promiscuous Second Messenger Assays

It is not possible to predict, a priori and based solely upon the GPCR sequence, which of the cell's many different signaling pathways any given receptor will naturally use. It is possible, however, to coax receptors of different functional classes to signal through a pre-selected pathway through the use of promiscuous $G_\alpha$ subunits. For example, by providing a cell based receptor assay system with an endogenously supplied promiscuous $G_\alpha$ subunit such as $G_{\alpha 15}$ or $G_{\alpha 16}$ or a chimeric $G_\alpha$ subunit such as $G_{\alpha qz}$, a GPCR, which might normally prefer to couple through a specific signaling pathway (e.g., $G_s$, $G_i$, $G_q$, $G_o$, etc.), can be made to couple through the pathway defined by the promiscuous $G_\alpha$ subunit and upon agonist activation produce the second messenger associated with that subunit's pathway. In the case of $G_{\alpha 15}$, $G_{\alpha 16}$ and/or $G_{\alpha qz}$ this would involve activation of the $G_q$ pathway and production of the second messenger $IP_3$. Through the use of similar strategies and tools, it is possible to bias receptor signaling through pathways producing other second messengers such as $Ca^{++}$, cAMP, and $K^+$ currents, for example (Milligan, 1999).

It follows that the promiscuous interaction of the exogenously supplied $G_\alpha$ subunit with the receptor alleviates the need to carry out a different assay for each possible signaling pathway and increases the chances of detecting a functional signal upon receptor activation.

Methods for Xenopus Oocytes Preparation, mRNA Injection and Electrophysiological Recording Female Xenopus laevis (Xenopus-1, Ann Arbor, Mich.) were anesthetized in 0.2% tricain (3-aminobenzoic acid ethyl ester, Sigma Chemical Corp.) and a portion of ovary was removed using aseptic technique (Quick and Lester, 1994). Oocytes were defolliculated, using 3 mg/ml collagenase (Worthington Biochemical Corp., Freehold, N.J.) in a solution containing 82.5 mM NaCl, 2 mM KCl, 1 mM $MgCl_2$ and 5 mM HEPES, pH 7.5, and injected (Nanoject, Drummond Scientific, Broomall, Pa.) 24 h later with 50-70 nl of individual mRNAs or mRNA mixtures (see below).

Elevation of intracellular cAMP is monitored in oocytes by expression of the cystic fibrosis transmembrane conductance regulator (CFTR) whose $Cl^-$-selective pore opens in response to phosphorylation by protein kinase A (Riordan, 1993). To prepare RNA transcripts for expression in oocytes, a template was created by PCR using 5' and 3' primers derived from the published sequence of the CFTR gene (Riordan, 1993). The 5' primer included the sequence coding for T7 polymerase so that transcripts could be generated directly from the PCR products without cloning. Oocytes were injected with 10 ng of CFTR mRNA in addition to 10-15 ng mRNA for SNORF33. Electrophysiological recordings were made after a 2-3 day incubation at 18° C.

Dual electrode voltage clamp ("GeneClamp", Axon Instruments Inc., Foster City, Calif.) was performed using 3 M KCl-filled glass microelectrodes having resistances of 1-3 Mohms. Unless otherwise specified, oocytes were voltage clamped at a holding potential of –80 mV. During recordings, oocytes were bathed in continuously flowing (1-3 ml/min) medium containing 96 mM NaCl, 2 mM KCl, 1.8 mM $CaCl_2$, 1 mM $MgCl_2$, and 5 mM HEPES, pH 7.5 (ND96). Drugs were applied either by local perfusion from a 10 µl glass capillary tube fixed at a distance of 0.5 mm from the oocyte, or for calculation of steady-state $EC_{50}$s of agonists and for all antagonist experiments, by switching from a series of gravity fed perfusion lines. Experiments were carried out at room temperature. All values are expressed as mean±standard error of the mean.

Methods for Recording Currents in Xenopus Oocytes

Oocytes are harvested from Xenopus laevis and injected with mRNA transcripts as previously described (Quick and Lester, 1994; Smith et al., 1997). The test receptor of this invention and Gα subunit RNA transcripts are synthesized using the T7 polymerase ("Message Machine," Ambion) from linearized plasmids or PCR products containing the complete coding region of the genes. Oocytes are injected with 10 ng synthetic receptor RNA and incubated for 3-8 days at 17 degrees. Three to eight hours prior to recording, oocytes are injected with 500 pg promiscuous Gα subunits mRNA in order to observe coupling to $Ca^{++}$ activated $Cl^-$ currents. Dual electrode voltage clamp (Axon Instruments Inc.) is performed using 3 M KCl-filled glass microelectrodes having resistances of 1-2 MOhm. Unless otherwise specified, oocytes are voltage clamped at a holding potential of −80 mV. During recordings, oocytes are bathed in continuously flowing (1-3 ml/min) medium containing 96 mM NaCl, 2 mM KCl, 1.8 mM $CaCl_2$, 1 mM $MgCl_2$, and 5 mM HEPES, pH 7.5 (ND96). Drugs are applied either by local perfusion from a 10 µl glass capillary tube fixed at a distance of 0.5 mm from the oocyte, or by switching from a series of gravity fed perfusion lines.

Other oocytes may be injected with a mixture of receptor mRNAs and synthetic mRNA encoding the genes for G-protein-activated inward rectifier channels (GIRK1 and GIRK4, U.S. Pat. Nos. 5,734,021 and 5,728,535 or GIRK1 and GIRK2) or any other appropriate combinations (see, e.g., Inanobe et al., 1999). Genes encoding G-protein inwardly rectifying $K^+$ (GIRK) channels 1, 2 and 4 (GIRK1, GIRK2, and GIRK4) may be obtained by PCR using the published sequences (Kubo et al., 1993; Dascal et al., 1993; Krapivinsky et al., 1995 and 1995b) to derive appropriate 5' and 3' primers. Human heart or brain cDNA may be used as template together with appropriate primers.

Heterologous expression of GPCRs in *Xenopus* oocytes has been widely used to determine the identity of signaling pathways activated by agonist stimulation (Gundersen et al., 1983; Takahashi et al., 1987). Activation of the phospholipase C (PLC) pathway is assayed by applying test compound in ND96 solution to oocytes previously injected with mRNA for the mammalian receptor (with or without promiscuous G proteins) and observing inward currents at a holding potential of −80 mV. The appearance of currents that reverse at −25 mV and display other properties of the $Ca^{++}$-activated $Cl^-$ (chloride) channel is indicative of mammalian receptor-activation of PLC and release of IP3 and intracellular $Ca^{++}$. Such activity is exhibited by GPCRs that couple to $G_q$ or $G_{11}$.

Measurement of inwardly rectifying $K^+$ (potassium) channel (GIRK) activity may be monitored in oocytes that have been co-injected with mRNAs encoding the mammalian receptor plus GIRK subunits. GIRK gene products co-assemble to form a G-protein activated potassium channel known to be activated (i.e., stimulated) by a number of GPCRs that couple to $G_i$ or $G_o$ (Kubo et al., 1993; Dascal et al., 1993). Oocytes expressing the mammalian receptor plus the GIRK subunits are tested for test compound responsivity by measuring $K^+$ currents in elevated $K^+$ solution containing 49 mM $K^+$.

Membrane Preparations

Cell membranes expressing the receptor protein of this invention are useful for certain types of assays including but not restricted to ligand binding assays, GTP-g-S binding assays, and others. The specifics of preparing such cell membranes may in some cases be determined by the nature of the ensuing assay but typically involve harvesting whole cells and disrupting the cell pellet by sonication in ice cold buffer (e.g. 20 mM Tris HCl, mM EDTA, pH 7.4 at 4° C.). The resulting crude cell lysate is cleared of cell debris by low speed centrifugation at 200×g for 5 min at 4° C. The cleared supernatant is then centrifuged at 40,000×g for 20 min at 4° C., and the resulting membrane pellet is washed by suspending in ice cold buffer and repeating the high speed centrifugation step. The final washed membrane pellet is resuspended in assay buffer. Protein concentrations are determined by the method of Bradford (1976) using bovine serum albumin as a standard. The membranes may be used immediately or frozen for later use.

Generation of Baculovirus

The coding region of DNA encoding the human receptor disclosed herein may be subcloned into pBlueBacIII into existing restriction sites or sites engineered into sequences 5' and 3' to the coding region of the polypeptides. To generate baculovirus, 0.5 µg of viral DNA (BaculoGold) and 3 µg of DNA construct encoding a polypeptide may be co-transfected into 2×10⁶ *Spodoptera frugiperda* insect Sf9 cells by the calcium phosphate co-precipitation method, as outlined by Pharmingen (in "Baculovirus Expression Vector System: Procedures and Methods Manual"). The cells then are incubated for 5 days at 27° C.

The supernatant of the co-transfection plate may be collected by centrifugation and the recombinant virus plaque purified. The procedure to infect cells with virus, to prepare stocks of virus and to titer the virus stocks are as described in Pharmingen's manual.

Generation of Baculovirus

The coding region of DNA encoding the human receptor disclosed herein may be subcloned into pBlueBacIII into existing restriction sites or sites engineered into sequences 5' and 3' to the coding region of the polypeptides. To generate baculovirus, 0.5 µg of viral DNA (BaculoGold) and 3 µg of DNA construct encoding a polypeptide may be co-transfected into 2×10⁶ *Spodoptera frugiperda* insect Sf9 cells by the calcium phosphate co-precipitation method, as outlined by Pharmingen (in "Baculovirus Expression Vector System: Procedures and Methods Manual"). The cells then are incubated for 5 days at 27° C.

The supernatant of the co-transfection plate may be collected by centrifugation and the recombinant virus plaque purified. The procedure to infect cells with virus, to prepare stocks of virus and to titer the virus stocks are as described in Pharmingen's manual.

Labeled Ligand Binding Assays

Cells expressing the receptors of this invention may be used to screen for ligands for said receptors, for example, by labeled [$^3$H]-TYR and [$^3$H]-T binding assays. The same assays may be used to identify agonists or antagonists of the receptors that may be employed for a variety of therapeutic purposes.

[$^3$H]-TYR and [$^3$H]-T binding assays were performed essentially as described by Mallard et al. (1992), with minor modifications. Radioligand binding assays were performed by diluting membranes prepared from cells expressing the receptor (with co-expression of the rat G-protein alpha S subunit for human SNORF33) in 25 mM Gly-Gly buffer (Sigma, pH=7.4 @ 0° C.) containing 5 mM ascorbate and 10 µM pargyline (final protein concentration in assay=100-300 µg/ml). Membranes were then incubated with either [$^3$H]-TYR (American Radiochemicals, specific activity 60 mCi/µmole) or [$^3$H]-T (Amersham, specific activity 98 mCi/µmole) in the presence or absence of competing ligands on ice for 30 min in a total volume of 250 µl in 96 well microtiter plates. The bound ligand was separated from free by filtration through GF/B filters presoaked in 0.5% polyethyleneimine (PEI), using Tomtec (Wallac) or Brandel Cell Harvester vacuum filtration device. After addition of Ready Safe (Beckman) scintillation fluid, bound radioactivity was quantitated using a Trilux (Wallac) scintillation counter (approximately 20% counting efficiency of bound counts). Data was fit to non-linear curves using GraphPad Prism.

In this manner, agonist or antagonist compounds that bind to the receptor may be identified as they inhibit the binding of the labeled ligand to the membrane protein of cells expressing the said receptor. Non-specific binding was defined as the amount of radioactivity remaining after incubation of membrane protein in the presence of 10 μM of the unlabeled amine corresponding to the radioligand used. In equilibrium saturation binding assays, membrane preparations or intact cells transfected with the receptor are incubated in the presence of increasing concentrations of the labeled compound to determine the binding affinity of the labeled ligand. The binding affinities of unlabeled compounds may be determined in equilibrium competition binding assays, using a fixed concentration of labeled compound in the presence of varying concentrations of the displacing ligands.

Localization of mRNA Coding for Human, Rat and Mouse SNORF33.

Quantitative RT-PCR using a fluorogenic probe with real time detection: Quantitative RT-PCR using fluorogenic probes and a panel of mRNA extracted from human, rat and mouse tissue was used to characterize the localization of SNORF33 human, rat and mouse RNA. This assay utilizes two oligonucleotides for conventional PCR amplification and a third specific oligonucleotide probe that is labeled with a reporter at the 5' end and a quencher at the 3' end of the oligonucleotide. In the instant invention, FAM (6-carboxyfluorescein), JOE (6 carboxy-4,5-dichloro-2,7-dimethoxyfluorescein) and VIC (PE Biosystems, Foster City Calif.) were the three reporters that were utilized and TAMRA (6-carboxy-4,7,2,7'-tetramethylrhodamine) was the quencher. As amplification progresses, the labeled oligonucleotide probe hybridizes to the gene sequence between the two oligonucleotides used for amplification. The nuclease activity of Taq, or rTth thermostable DNA polymerases is utilized to cleave the labeled probe. This separates the quencher from the reporter and generates a fluorescent signal that is directly proportional to the amount of amplicon generated. This labeled probe confers a high degree of specificity. Non-specific amplification is not detected as the labeled probe does not hybridize. All experiments were conducted in a PE7700 Sequence Detection System (Perkin Elmer, Foster City Calif.).

Quantitative RT-PCR: For the detection of RNA encoding SNORF33, quantitative RT-PCR was performed on RNA extracted from tissue. Reverse transcription and PCR reactions were carried out in 50 μl volumes using rTth DNA polymerase (Perkin Elmer). Primers with the following sequences were used:

SNORF33 Human:

```
Forward primer:
SNORF33h 41F
5'-CATGGCCACTGTGGACTTTCT-3'          (SEQ ID NO: 22)

Reverse primer
SNORF33h 158R
5'-GTCGGTGCTTGTGTGAATTTTACA-3'       (SEQ ID NO: 23)

Fluorogenic oligonucleotide probe:
SNORF33h-90T
5' (6-FAM)-ATGGTGAGATCTGCTGAGCACTG ((SEQ ID NO: 24)
TTGGTATT-(TAMRA) 3'
```

SNORF33 Rat:

```
forward primer
SNORF33R-1067F
5'-TGCATGGTCCTGGACCCT-3'             (SEQ ID NO: 25)

reverse primer
SNORF33R.seq-1163R
5'-TCGGGTTGAAGGCAGAGTTC-3'           (SEQ ID NO: 26)
```

```
Fluorogenic oligonucleotide probe:
SNORF33R-1089T
5' (6-FAM)-TGGGCTATGTTATCCCACCCACT  (SEQ ID No: 27)
CTGAAT-(TAMRA) 3'
```

SNORF33 Mouse:

```
forward primer
snorf33mouse frag-602F
5'-AAAGCCGCGAAGACCTTAGG-3'           (SEQ ID NO: 44)

reverse primer
snorf33mouse frag-683R
5'-GGTCCAGGACCGTGCAGA-3'             (SEQ ID NO: 45)

Fluorogenic oligonucleotide probe:
snorf33mouse frag-638T
5' (6-FAM)-TTCCTCGTATGCTGGTGCCCGTT  (SEQ ID NO: 46)
CTTT-(TAMRA)-3'
```

Using these primer pairs, amplicon length is 117 bp for human SNORF33, 96 bp for rat SNORF33 and 81 bp for mouse SNORF33. Each RT-PCR reaction contained 50-100 ng RNA. Oligonucleotide concentrations were: 500 nM of forward and reverse primers, and 200 nM of fluorogenic probe. Concentrations of reagents in each reaction were: 300 μM each of dGTP; dATP; dCTP; 600 μM UTP; 3.0 mM Mn(OAc)2; 50 mM Bicine; 115 mM potassium acetate, 8% glycerol, 5 units rTth DNA polymerase, and 0.5 units of uracil N-glycosylase. Buffer for RT-PCR reactions also contained a fluor used as a passive reference (ROX: Perkin Elmer proprietary passive reference I). All reagents for RT-PCR (except mRNA and oligonucleotides) were obtained from Perkin Elmer (Foster City, Calif.). Reactions were carried using the following thermal cycler profile: 50° C. 2 min., 60° C. 30 min., 95° C. 5 min., followed by 40 cycles of: 94° C. 20 sec., 62° C. 1 min.

Standard curves for quantitation of human, rat and mouse SNORF33 were constructed using human or mouse genomic DNA or rat stomach RNA. Negative controls consisted of mRNA blanks, as well as primer and mRNA blanks. To confirm that the mRNA was not contaminated with genomic DNA, PCR reactions were carried out without reverse transcription using Taq DNA polymerase. Integrity of RNA was assessed by amplification of mRNA coding for cyclophilin or glyceraldehyde 3-phosphate dehydrogenase (GAPDH). Following reverse transcription and PCR amplification, data was analyzed using Perkin Elmer sequence detection software. The fluorescent signal from each well was normalized using an internal passive reference, and data was fitted to a standard curve to obtain relative quantities of SNORF33 mRNA expression.

Chromosomal Localization of Human SNORF33

Chromosomal localization of the human SNORF33 receptor gene was established using a panel of radiation hybrids prepared by the Stanford Human Genome Center (SHGC) and distributed by Research Genetics, Inc. The "Stanford G3" panel of 83 radiation hybrids was analyzed by PCR using the same primers, probes and thermal cycler profiles as used for localization. 20 ng of DNA was used in each PCR reaction. Data was submitted to the RH Server (SHGC) which linked the SNORF 33 gene sequence to specific markers. NCBI LocusLink and NCBI GeneMap '99 were used to further analyze gene localization. Chromosomal localization of SNORF 33 was compared with other normal genes and genes associated with morbidity using: Online Mendelian Inheritance in Man, OMIM (TM), McKusick-Nathans Institute for Genetic Medicine, Johns Hopkins University (Baltimore, Md.) and National Center for Biotechnology Information, National Library of Medicine (Bethesda, Md.), 2000. World Wide Web URL: http://www.ncbi.nlm.nih.gov/omim/.

In Situ Hybridization Experiments for SNORF33 mRNA

Tissue Preparation for neuroanatomical studies: Male Sprague-Dawley rats (Charles Rivers, Rochester, N.Y.) were euthanized using $CO_2$, decapitated, and their brains and select peripheral tissues immediately removed and rapidly frozen on crushed dry ice. Coronal sections of brain tissue and peripheral tissues were cut at 11 µm using a cryostat and thaw-mounted onto poly-L-lysine-coated slides and stored at −20° C. until use. Prior to hybridization, the tissues were fixed in 4% paraformaldehyde/PBS pH 7.4 followed by two washes in PBS (Specialty Media, Lavallette, N.J.). Tissues were then treated in 5 mM dithiothreitol, rinsed in DEPC-treated water, acetylated in 0.1 M triethanolamine containing 0.25% acetic anhydride, rinsed twice in 2× SSC, delipidated with chloroform then dehydrated through a series of graded alcohols. All reagents were purchased from Sigma (St. Louis, Mo.).

In Situ Hybridization Histochemistry

Oligonucleotide probes, BB1009/1010, corresponding to nucleotides 115-159 of the rat SNORF33 cDNA, were used to characterize the distribution of each receptor's respective mRNA. The oligonucleotides were synthesized using an Expedite Nucleic Acid Synthesis System (PerSeptive Biosystems, Framingham, Mass.) and purified using 12% polyacrylamide gel electrophoresis.

The sequences of the rat SNORF33 oligonucleotides are:

```
Sense probe:
BB1009:         5'-CAC ACG AAC AGC (SEQ ID NO: 28)
                AAC TGG TCA AGG
                GAT CGT GCT TCG
                CTG TAC-3'

Antisense probe:
B1010:          5'-GTA CAG CGA AGC (SEQ ID No: 29)
                ACG GAC ATC CCT
                TGA CCA GTT GCT
                GTT CGT GTG-3'
```

Probes were 3'-end labeled with [$^{35}$S]dATP (1200 Ci/mmol, NEN, Boston, Mass.) to a specific activity of $10^9$ dpm/µg using terminal deoxynucleotidyl transferase (Pharmacia, Piscataway, N.J.). In situ hybridization was done with modification of the method described by Durkin, et al. (1995).

Nonradioactive In Situ Hybridization Histochemistry

Male Sprague-Dawley rats (200-250 g) (Charles, Rivers) and male 1295S6/SVEV mice (20 g) (Taconic Farms, Germantown, N.Y.) were anesthetized using a 1:5 mixture of Rompun/ketamine (100 mg/ml) (Bayer Agricultural Division Shawnee Mission, KA, Sigma, St. Louis, Mo.). The rats and mice were transcardially perfused with 5 mM phosphate-buffered saline (PBS) pH7.4 (250 ml or 100 ml, respectively) followed by 4% paraformaldehyde/PBS, (250 or 75 ml, respectively). Their brains were dissected, immersed in 4% paraformaldehyde/PBS at 4° C. from between 2 (mice) to 4 (rats) hours, followed by immersion in 30% sucrose at 4° C. overnight to cryoprotect, cut into several blocks, frozen on crushed dry ice, and stored at −20° C. until use. Tissues were sectioned at 30 µm using a freezing microtome, stored in DEPC treated PBS at 4° C. until use, and then processed free-floating in 6 well plates.

A 310 base pair SacI-KpnI fragment derived from rat SNORF33 cDNA (KO34) was subcloned in a pBleuscript vector and used as a template to generate digoxigenin-labeled transcripts in either orientation using T3/T7 transcript kits (Roche Molecular Biochemicals). An antisense riboprobe labeled with digoxigenin was transcribed by T7 RNA polymerase (Roche Molecular Biochemicals) using the template linearized by SacI (Roche Molecular Biochemicals). T3 RNA polymerase (Promega) using the same template linearized by KpnI (Roche Molecular Biochemicals) generated the sense strand riboprobe. For the mouse riboprobes, a 251 base pair HindIII-BamHI fragment derived from mouse SNORF33 cDNA (KO94) was subcloned into pEXJRHT3T7 vector and used as a template to generate digoxigenin-labeled transcripts in either orientation using T3/T7 transcript kits. An antisense riboprobe labeled with digoxigenin was transcribed by T7 RNA polymerase using the template linearized by BamI. T3 RNA polymerase using the same template linearized by HindIII (Roche Molecular Biochemicals) generated the sense strand riboprobe.

The labeling reactions for the rat and mouse riboprobes were carried out as outlined in the DIG/Genius System, (Roche Molecular Biochemicals, Indianapolis, Ind.). Briefly, digoxigenin-labeled riboprobes, were transcribed at 37° C. for 2 hours in 20 µl transcription mix that contained 1 µg linearized template, transcription buffer (Tris-MgCl-spermidine), 1 mM each of ATP, CTP, and GTP, 0.65 mM UTP, 0.35 mM digoxigenin labeled UTP (Roche Molecular Biochemicals), the appropriate RNA Polymerase and Molecular Grade Water (Research Products International Corp., Mount Prospect, Ill.). Following transcription, the reaction was stopped by the addition of 200 mM EDTA and 4 mM lithium chloride followed by ethanol precipitation. Probes were reconstituted in Molecular Grade Water and stored at −20° C. until use.

Tissues were rinsed in DEPC-PBS twice for 5 min, DEPC-PBS containing 100 mM glycine twice for 5 min, DEPC-PBS containing 0.3% Triton X-100 for 15 min, then washed in DEPC-PBS twice for 5 min. The sections were hybridized in buffer containing 40% formamide, 10% Dextran sulfate, 4×SSC, 10 mM DTT, Denhardt's 1×, 1 mg/ml Salmon Sperm DNA, 1 mg/ml yeast tRNA and Molecular Grade Water, and 5 to 7 ng/µl digoxigenin-labeled riboprobe. Each of the 6 wells contained 4 ml of probe/hybridization buffer and the free-floating tissues were immersed in the buffer and allowed to hybridize overnight at 42° C. for the rat and 52° C. for the mouse. The following morning, sections were washed twice in 2× SSC at 37° C. for 15 min, twice in 1× SSC at 37° C. for 15 min, followed by 20 µg/ml RNase A in NTE buffer (500 mM NaCl, 10 mM Tris, 1 mM EDTA, pH 8.0) at 37° C. for 30 min, and two washes 0.1× SSC at 37° C. for 15 min.

For rat immunological detection, the sections were washed twice in TNT (100 mM Tris-HCl, 150 mM NaCl and 0.05% Tween 20, pH 7.4), preincubated for 30 min in TNB (100 mM Tris-HCl, 150 mM NaCl, 0.5% Blocking Reagent, pH 7.4) (NEN TSA Biotin System), and then incubated for 2 hours in TNB buffer containing anti-digoxigenin-POD (1:25) (Roche Molecular Biochemicals). The sections were washed twice in TNT, incubated 10 min in Biotinylated Tyramide (1:50) in amplification diluent (NEN TSA Biotin System), washed twice in TNT, then incubated 1 hour in Strepavidin-POD (1:100) (NEN TSA Biotin System) diluted in TNB. Sections were rinsed in PBS followed by 0.1 M Tris-HCl, pH 7.4, until color detection. DAB (20 mg) (Sigma, St. Louis, Mo.) was dissolved in 40 ml 0.1 M Tris-HCl, pH 7.4, and 20 µl 30% $H_2O_2$ was added immediately before use. The color reaction was allowed to continue for 6 min then stopped by rinsing in $dH_2O$. Sections were mounted onto slides using Mounting Media (40% EtOH:gelatin), allowed to air dry for 1 hour, counterstained with hematoxlin, dehydrated through a series of alcohols, cleared in Histo-Clear (National Diagnostics, Atlanta, Ga.) then coverslipped with Cytoseal 60 (Stephans Scientific, Kalamazoo, Mich.).

For immunologic detection in the mouse, tissue sections were rinsed in Buffer 1, (0.1 M Tris-HCl, 0.15 M NaCl, 0.1% Triton X-100, pH 7.5), pre-incubated in Blocking Solution (0.1% Triton X-100 and 2% normal sheep serum) for 30 min and then incubated for 2 hours in Blocking Solution containing anti-digoxigenin-AP Fab fragment (1:500) (Roche Molecular Biochemicals) followed by two 10 min washes in Buffer 1. To develop the blue color, sections were rinsed in Detection Buffer (0.1 M Tris-HCl, 0.15 M NaCl, 0.05 M $MgCl_2$, pH 9.5) for 10 min and incubated overnight in Detection Buffer containing 0.5 mM NBT, 0.1 mM BCIP, and 1 mM levamisole. After color development, the reaction was stopped in TE, pH 8.0, the sections washed three times in $dH_2O$, mounted onto slides using mounting media (40% EtOH:gelatin), counterstained in 0.02% Fast Green then coverslipped using Aqua Mount7 (Lerner Laboratories, Pittsburgh, Pa.).

Controls

Probe specificity was established by performing in situ hybridization on COS-7 cells transiently transfected with eukaryotic expression vectors containing the rat and mouse SNORF33 DNA or no insert for transfection, as described in the above Methods section. Prior to hybridization, the cells were fixed in 4% paraformaldehyde, treated with 0.2% Triton X-100, and washed in PBS.

Quantification

The strength of the hybridization signal obtained in various region of the rat and mouse brain was graded as absent (−), weak (+) moderate (++), intense (+++). These were qualitative evaluations for the rat and mouse SNORF33 mRNA distribution based on the relative intensity of the chromogen (3,3=-Diaminobenzidine or alkaline phosphatase) observed in individual cells at the microscopic level.

RESULTS AND DISCUSSION

Isolation of a Full-Length Rat SNORF33 Receptor 100 ng rat genomic DNA was subjected to MOPAC PCR with two degenerate primers designed based on the sixth and seventh transmembrane domains of select serotonin receptors. One product from this reaction, 5-HT-38-rgen-051, was found to be a novel DNA sequence not found in the Genbank databases (Genembl, STS, EST, GSS), which had 42-48% amino acid identity to $5HT_4$, dopamine $D_2$ and β-adrenergic receptors. This novel sequence was designated SNORF33.

The full-length rat SNORF33 sequence was acquired by screening a rat genomic phage library with a SNORF33 specific oligonucleotide probe. Southern blot analysis of a single isolated plaque identified a 5.5 kb fragment which was subcloned (KO26) and sequenced. Sequencing of KO26 revealed an open reading frame of 996 bp that is predicted to encode a protein of 332 amino acids. A 1.8 kb fragment of KO26, including the 996 bp open reading frame, was subcloned into pcDNA3.1, resulting in the construct named BO111. The nucleotide sequence of rat SNORF33 and its translated amino acid sequence are represented in FIGS. 3A-3B and 4A-4B, respectively. An allelic variant of this receptor was also identified. In this variant, an adenine replaces a thymine at position 561 in FIGS. 3A-3B. This results in an amino acid change from leucine to glutamine at position 170 in FIGS. 4A-4B.

Hydrophobicity (Kyte-Doolittle) analysis of the amino acid sequence of the full-length clone indicates the presence of seven hydrophobic regions, which is consistent with the seven transmembrane domains of a G protein-coupled receptor. The seven expected transmembrane domains are indicated in FIG. 4. A comparison of nucleotide and peptide sequences of rat SNORF33 with sequences contained in the Genbank, EMBL and SwissProtPlus databases reveals that the amino acid sequence of this clone is most related to the $5HT_4$-like pseudogene (44% amino acid identity) and PNR (GenBank accession number 2465432; 38% amino acid identity), $5HT_{1D}$, $5HT_4$ and dopamine $D_1$ receptors (35-36% amino acid identities) and histamine $H_1$ and $\alpha_{1c}$ adrenergic receptors (33% amino acid identity). There were no sequences in the Genbank databases (Genembl, STS, EST, GSS, or SwissProt) that were identical to SNORF33.

SNORF33 has one potential protein kinase C (PKC) phosphorylation motif at serine 325 in the carboxy-terminal tail. It also has three potential N-linked glycosylation sites at asparagines 9 and 14 in the amino-terminal tail and at asparagine 283 in the seventh transmembrane domain.

Isolation of the Human SNORF33 Homologue

A fragment of the human homologue of SNORF33 was amplified from human genomic DNA by low stringency PCR using oligonucleotide primers designed against the rat SNORF33. The sequence of this fragment was then used to generate human SNORF33 PCR primers which were used to amplify under high stringency a SNORF33 fragment from human genomic DNA. This fragment, KO28, contains 573 nucleotides of human SNORF33, from TMII to the beginning of TMVI. The nucleotide and amino acid sequences of the human SNORF33 fragment are shown in FIGS. 1 and 2, respectively. The human SNORF33 fragment shares 79% nucleotide and amino acid identity with the rat SNORF33.

Isolation of the Full-Length Human SNORF33

Figure 6A:
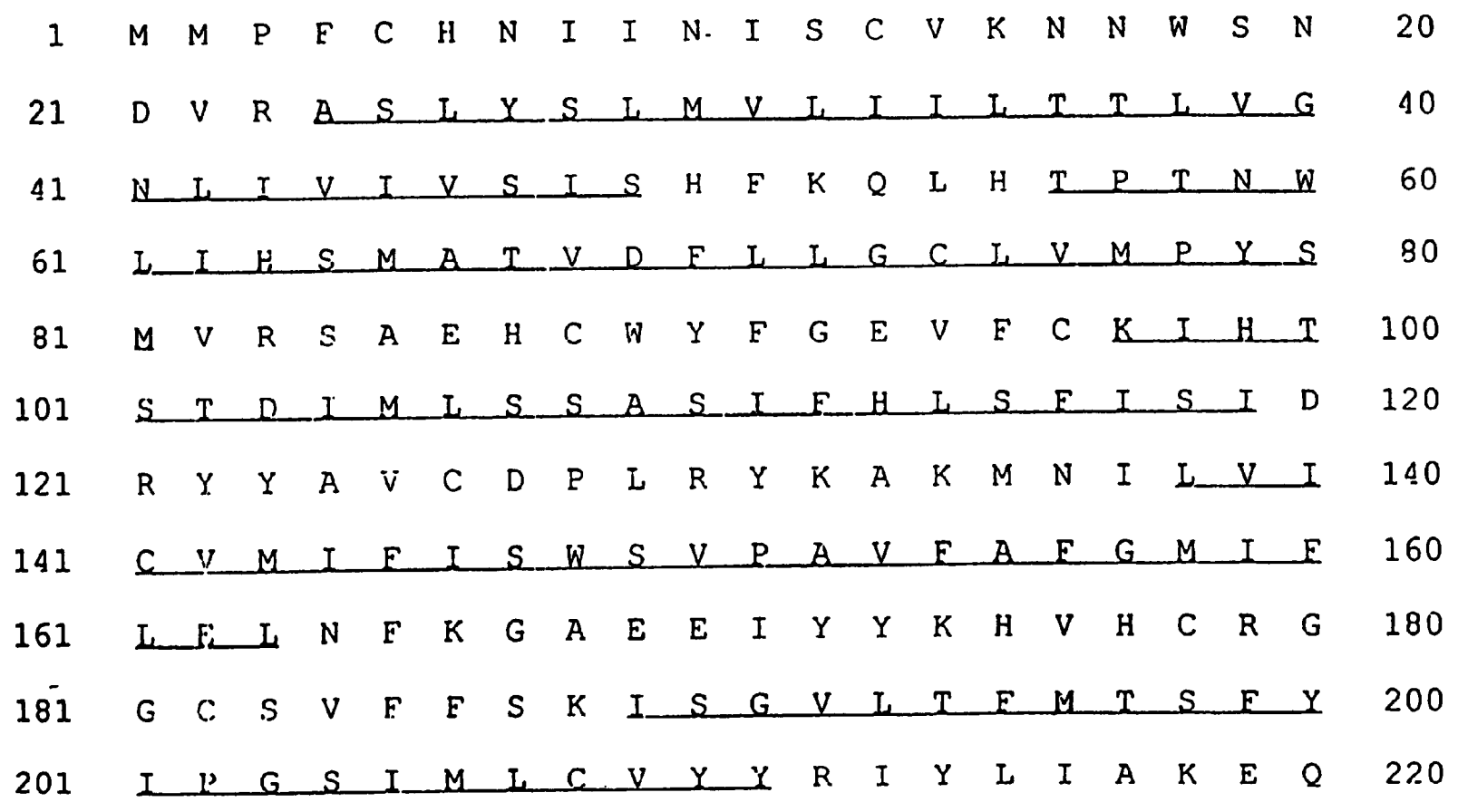
Figure 6B:
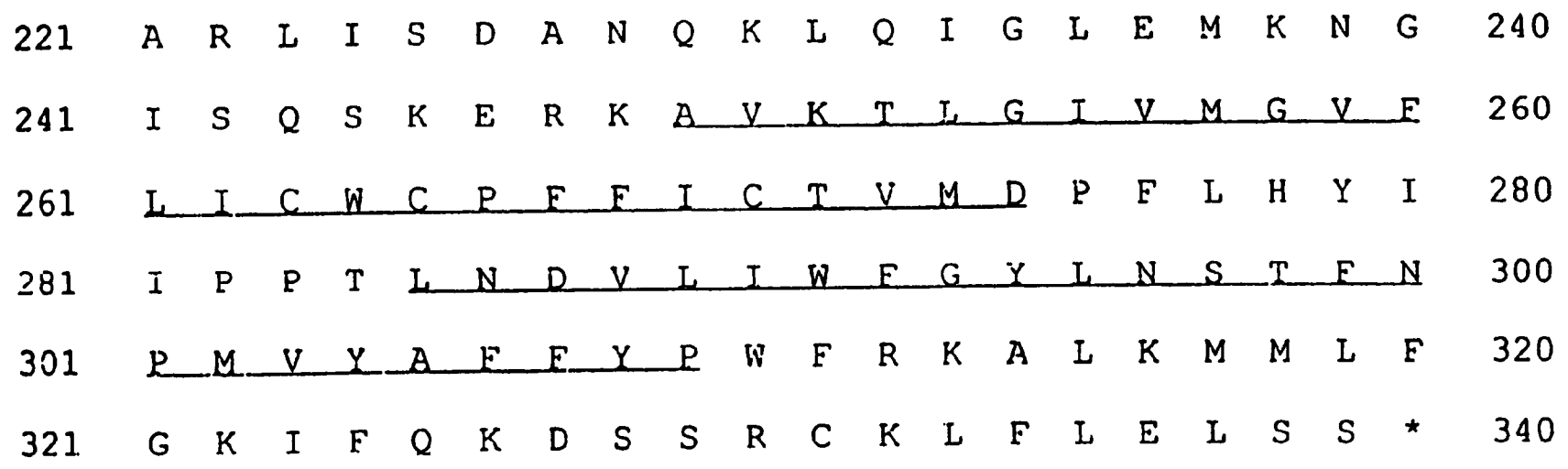

To obtain the full-length human SNORF33, 5' and 3' RACE was performed on human kidney and stomach cDNA. The 5' RACE reaction yielded a 500 bp band that contained sequence information through the first transmembrane domain and a putative in-frame initiating methionine-coding sequence. The 3' RACE reaction yielded a 350 bp band that contained sequence for an in-frame stop codon downstream from the region coding for the seventh transmembrane domain. Two primers, BB1101 and BB1102, were used to amplify the entire coding sequence from human genomic DNA and human amygdala cDNA using the Expand Long Template PCR system. The primers for this reaction were specific to the 5' and 3' untranslated regions of SNORF33 with BamHI and HindIII restriction sites incorporated into the 5' ends of the 5' and 3' primers, respectively. The products of these reactions were subcloned into pcDNA3.1 and sequenced. The full-length human SNORF33 in pcDNA3.1, BO113, was named pcDNA3.1-hSNORF33-f. A BamHI/HindIII fragment of BO113, containing the entire SNORF33 insert, was ligated into a BamHI/HindIII digested pEXJ.RHT3T7 vector. This construct, BO114, was named pEXJ-hSNORF33-f. The largest open reading frame in human SNORF33 is 1017 nucleotides (FIGS. 5A-5B), and predicts a protein a protein of 339 amino acids (FIGS. 6A-6B). A comparison of the rat and human SNORF33 sequences reveals 79% nucleotide identity and 78% amino acid identity (FIGS. 7A-7B). Hydrophobicity (Kyte-Doolittle) analysis of the amino acid sequence of the full-length clone indicates the presence of seven hydrophobic regions, which is consistent with the seven transmembrane domains of a G protein-coupled receptor (FIGS. 6A-6B).

A comparison of nucleotide and peptide sequences of human SNORF33 with sequences contained in the Genbank, EMBL, and SwissProtPlus databases reveals that the amino acid sequence of this clone is most related to the 5HT$_4$-like pseudogene (46% amino acid identity) and PNR (GenBank accession number 2465432; 40% amino acid identity), 5HT1$_D$ and 5HT4 receptors (35-38% amino acid identities) and histamine H1, dopamine D1 and α1c adrenergic receptors (33-34% amino acid identities). There were no sequences in the Genbank databases (Genembl, STS, EST, GSS, or SwissProt) that were identical to SNORF33.

Human SNORF33 has one potential protein kinase C (PKC) phosphorylation motif at serine 328 in the carboxy-terminal tail. It also has three potential N-linked glycosylation sites at asparagines 10 and 17 in the amino-terminal tail and at asparagine 296 in the seventh transmembrane domain.

Isolation of the Mouse SNORF33 Homologue

A fragment of the mouse homologue of SNORF33 was amplified from mouse genomic DNA by low stringency PCR using oligonucleotide primers designed against the rat SNORF33. The sequence of this fragment was then used to generate mouse SNORF33 PCR primers which were used to amplify under high stringency a SNORF33 fragment from mouse genomic DNA. This fragment, KO94, contains 252 nucleotides of mouse SNORF33, from TMV to the beginning of the third extracellular loop. The amino acid and nucleotide sequences of the mouse SNORF33 fragment are shown in FIGS. 17 and 18. The mouse SNORF33 fragment shares 93% nucleotide and 92% amino acid identity with the rat SNORF33 receptor. The mouse SNORF33 fragment shares 78% nucleotide and 72% amino acid identity with the human SNORF33 receptor.

Isolation of the Full-Length Mouse SNORF33

Figure 20A:
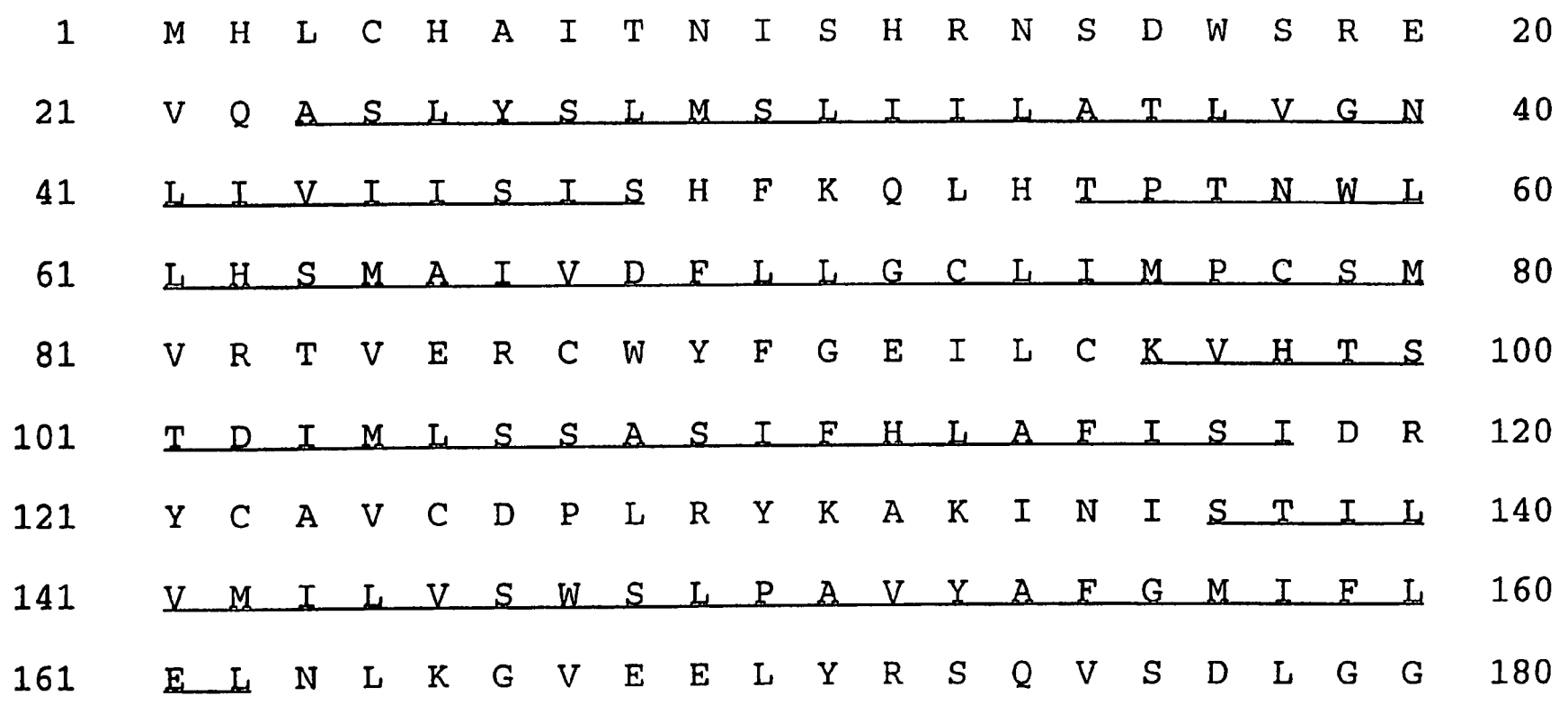
Figure 20B:
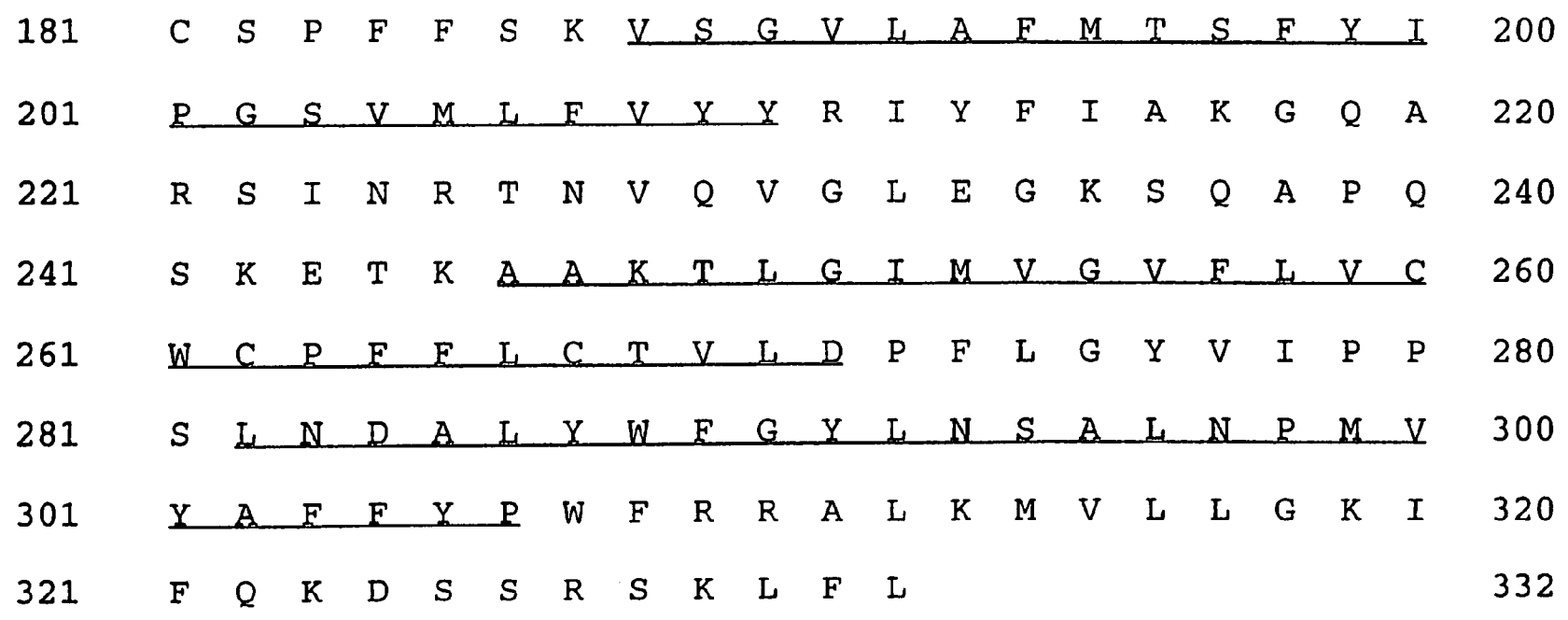

The 3' RACE reaction yielded a 900 bp band that contained sequence information through an in-frame stop codon downstream from the region coding for the seventh transmembrane domain. Reduced stringency PCR using one rat SNORF33 primer and one mouse SNORF33 primer yielded a 300 bp fragment which contained sequence information through an in-frame initiating methionine. Two primers, BB1307 and BB1308, were used to amplify the entire coding sequence from mouse genomic DNA. The full-length mouse SNORF33 in pEXJ, BO131, was named pEXJ-mSNORF33-f. The largest open reading frame in mouse SNORF33 is 996 nucleotides (FIGS. 19A-19B), and predicts a protein of 332 amino acids (FIGS. 20A-20B). A comparison of the mouse and rat SNORF33 sequences reveals 90% nucleotide identity and 87% amino acid identity. A comparison of the mouse and human SNORF33 sequences reveals 79% nucleotide identity and 76% amino acid identity. An amino acid alignment of the three species of SNORF33 is shown in FIG. 21. Hydrophobicity (Kyte-Doolittle) analysis of the amino acid sequence of the full-length clone indicates the presence of seven hydrophobic regions, which is consistent with the seven transmembrane domains of a G protein-coupled receptor (FIGS. 20A-20B).

Figure 10:
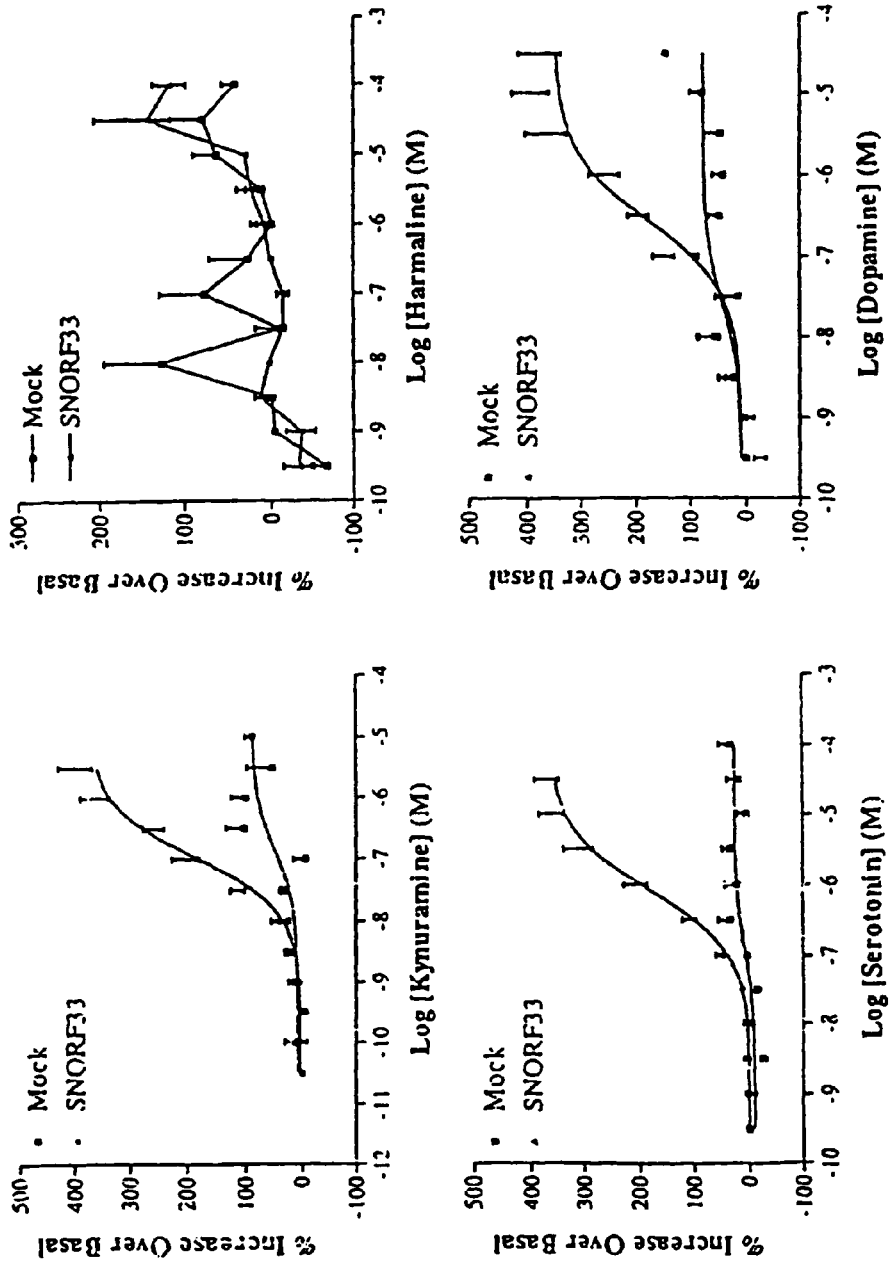
FIG. 10
Effect of pharmacological agents on intracellular cAMP levels in DNA vector (Mock)- and rSNORF33-transfected COS-7 cells. The data are presented as mean±S.E.M. Number of experiments=3-8.

Increase in Intracellular cAMP Levels:

COS-7 cells were transiently transfected with rSNORF33 and vector DNA (mock) as described in Materials and Methods. Activation of rSNORF33 receptor by various ligands resulted in enhancement of intracellular cAMP levels (FIG. 9, FIG. 10, Table 1) but not intracellular Ca$^{++}$ release (measured by FLIPR). In contrast, these ligands had no or significantly less effect on cAMP levels in vector-transfected cells (FIG. 9, FIG. 10). Interestingly, the basal cAMP levels of rSNORF33-transfected cells were significantly higher than mock-transfected cells (FIG. 8). These results suggest that rSNORF33 receptor is positively coupled to adenylyl cyclase, most probably via Gs-class of G-proteins.

Several "trace amines" displayed high potencies of approximately 10-20 nM for stimulating cAMP levels in rSNORF33-transfected cells with the following rank order of potencies TYR>PEA>T. Another "trace amine", OCT, displayed about an order of magnitude lower potency as compared to the above amines (Table 1).

Amphetamine which belongs to the structural class of phenylethylamines showed relatively high potency in the cAMP assay (see Table 1), in fact, it is only about 2-fold less potent than TYR and PEA. Amphetamines are well known for their CNS stimulating and appetite suppressing properties and they are the most potent anorectic compounds known in man as well as in other species. It is noteworthy that the (R)-enantiomer of amphetamine is more active than the (S)- at the rSNORF33, whereas the reverse is true for in vivo CNS stimulating effects of amphetamine on locomotion and neurotransmitter release.

Tryptamine has been shown to have relatively high affinity (1-100 nM Ki values) at several cloned 5-HT receptors. 5-Hydroxytryptamine was found to be 70-fold less potent than the three "trace amines" mentioned above, in activating rSNORF33 (Table 1). Furthermore, TYR and OCT, which have low affinity for 5-HT receptors, activated rSNORF33 with relatively high potencies (Table 1). Similarly, rSNORF33 does not display adrenergic, dopaminergic or histaminergic pharmacology since DA was a much weaker agonist than the three most potent "trace amines" (Table 1) and NE and histamine were inactive at the cloned rSNORF33 receptor (data not shown). Indeed, rSNORF33 displays a unique pharmacological profile unlike any other cloned or native aminergic receptor described previously.

Unexpectedly, several compounds, notably desipramine and fluoxetine, which produce their physiological effects indirectly by inhibiting uptake of neurotransmitters, acted as direct agonists at rSNORF33 (Table 1). Desipramine and fluoxetine are very effective antidepressants clinically. Since the above mentioned drugs activate rSNORF33, it is possible that some of their physiological effects described are mediated via their actions at rSNORF33.

TABLE 1

Agonist Potencies For Stimulation Of rSNORF33 Receptors As Measured By Intracellular cAMP Release In SNORF33-Transfected COS-7 Cells.

| Compounds | Mean* EC$_{50}$ ± S.E.M.[#] (nM) |
|---|---|
| Tyramine (TYR) | 9 ± 6 |
| Tryptamine (T) | 17 ± 4 |
| β-Phenylethylamine (PEA) | 10 ± 1 |
| (R)-Amphetamine | 17 ± 7 |
| (S)-Amphetamine | 43 ± 11 |
| Kynuramine | 90 ± 20 |
| Methamphetamine | 115 ± 66 |
| Octopamine (OCT) | 135 ± 54 |
| 5-Fluoro-Tryptamine | 232 ± 38 |
| Dopamine (DA) | 273 ± 22 |
| 5-Methoxy-Tryptamine | 414 ± 161 |
| 5-Methyl-Tryptamine | 752 ± 285 |
| Serotonin (5-HT) | 1240 ± 526 |
| Phenylpropanolamine (PPA) | 1798 ± 1376 |
| Desipramine | 4300 ± 1868 |
| Fluoxetine | 5521 ± 3521 |

*calculated using results from 3–8 experiments
[#]S.E.M.; Standard Error of Mean Activation of Currents in SNORF33 Expressing *Xenopus* Oocytes The activity of rSNORF33 was tested in oocytes co-injected with mRNA encoding rSNORF33 and mRNA encoding CFTR. Initially, a broad panel of candidate agonists were tested. From this broad panel, OCT and, more weakly, DA and 5-HT, elicited Cl⁻ currents at 100 µM. Subsequently, several other biogenic amines, including TYR and T (1-100 µM), also produced this activity. These responses were specific to the expression of rSNORF33 since no such currents were observed in other oocytes injected with only mRNA encoding the CFTR channel. Similar currents were observed in oocytes challenged with DA and expressing the dopamine $D_1$ receptor, which is known to stimulate adenylyl cyclase. The "trace amines" did not stimulate Cl⁻ currents in oocytes lacking CFTR, indicating that the $G_{\alpha_q}$-mediated phospholipase C pathway was not activated. Responses also were not evoked in oocytes expressing chimeric G-proteins which are able to couple $G_{\alpha_i}$- and $G_{\alpha_o}$-coupled GPCRs to the phospholipase C pathway. Taken together, these observations support the conclusion that rSNORF33 encodes a GPCR which binds several trace biogenic amines and stimulates the production of cAMP, presumably via activation of $G_{\alpha_s}$.

Figure 11A:
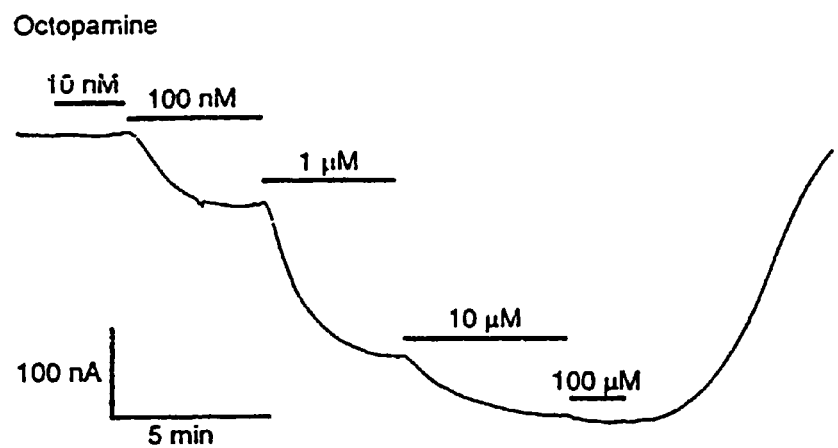
FIGS. 11A and 11B
(FIG. 11A) Example of a cumulative concentration-response to octopamine in an oocyte expressing SNORF33 and CFTR. Oocyte was voltage clamped to −80 mV and drug was applied at increasing concentrations as indicated by the horizontal bars.
Figure 11B:
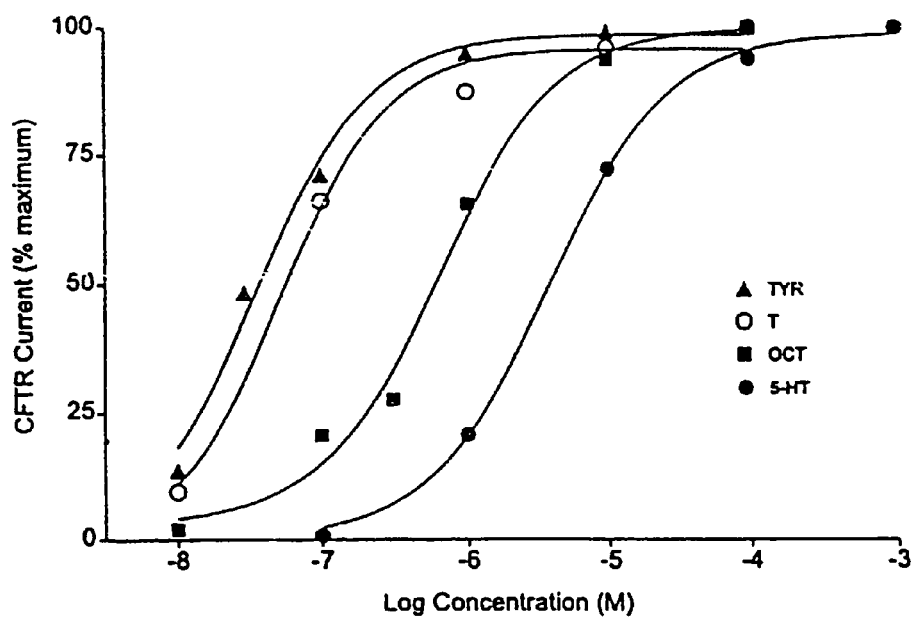

Quantitative pharmacology was performed on the selected agonists TYR, T, OCT and 5-HT. The effect of stepwise increasing the concentration of agonist on the amplitude of Cl⁻ current is shown in FIG. 11A. Averaged concentration-effect data for selected agonists are shown in FIG. 11B. Calculated $EC_{50}$ values for the four agonists were 37±4.4 nM for TYR, 54±10 nM for T, 635±151 nM for OCT and 3776±3.17 nM for 5-HT. This rank order of potencies is consistent with those obtained for the CAMP responses mediated by rSNORF33 in COS-7 cells and provides support for rSNORF33 being a TYR receptor.

Figure 12:
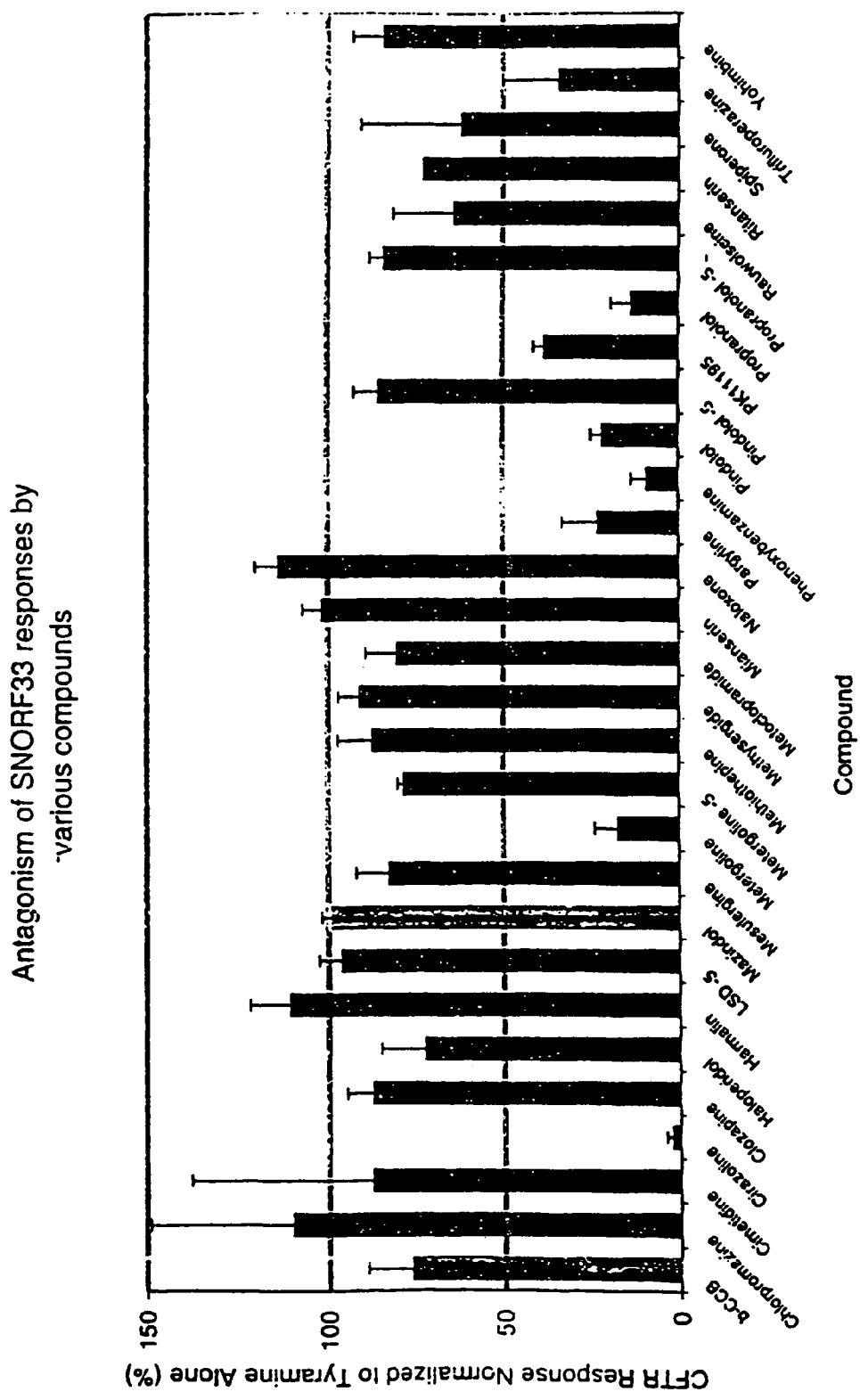
FIG. 12

A series of compounds, which included ligands for several biogenic amine receptors, were tested for their ability to antagonize responses elicited by 100 nM TYR (FIG. 12). At the test concentration (100 µM except where noted), most of the compounds had little or no significant antagonist activity (<50% inhibition).

Phenoxybenzamine, which irreversibly blocks several biogenic amine receptors, including T receptors in the rat stomach (Winter and Gessner, 1968), also produced an irreversible inhibition of rSNORF33. Thus, rSNORF33 shares several of the pharmacological properties of T receptors found in the rat brain and periphery.

Antagonists effective at invertebrate OCT and/or TYR receptors, such as mianserin, yohimbine and rauwolscine, did not significantly inhibit TYR stimulation of rSNORF33. This result correlates with the observation that two other compounds that act as antagonists at OCT receptors, phentolamine and cyproheptadine, actually produced an agonist effect. Thus, rSNORF33 is pharmacologically distinct from invertebrate OCT and TYR receptors.

The most potent inhibition was affected by the alpha-1 adrenergic agonist, cirazoline, which produced a greater than 90% inhibition of the response to TYR. It is noteworthy that cirazoline also has additional high affinity for imidazoline receptors. Test compounds having the ability to significantly block the activity of rSNORF33 also included two β-adrenoceptor antagonists, propanolol and pindolol, and the 5-HT receptor antagonist, metergoline. Thus, rSNORF33 shares some of the pharmacological properties of adrenergic, imidazoline and serotonergic receptors.

Figure 16:
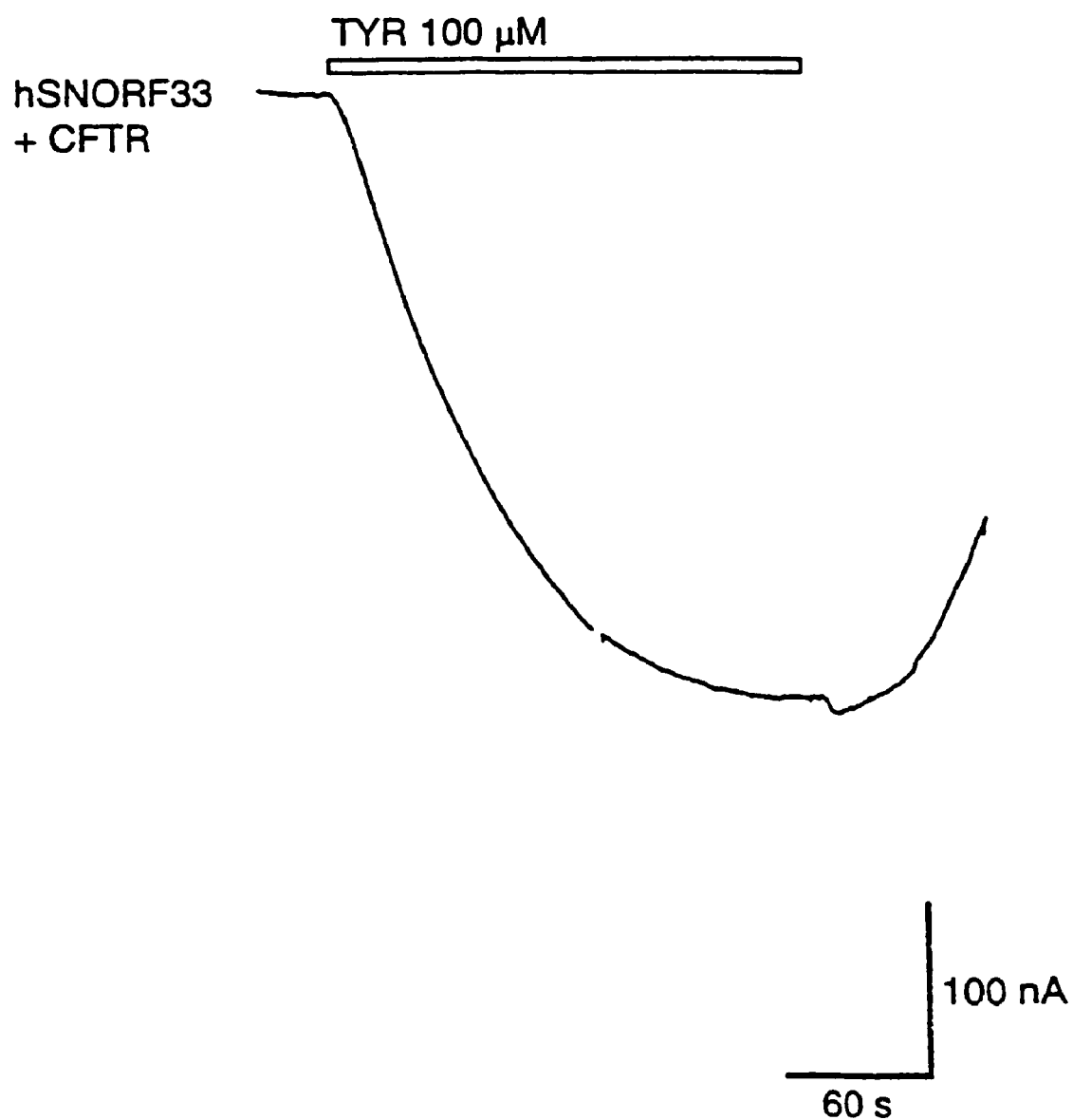

Human SNORF33 mRNA was transcribed and injected into *Xenopus* oocytes. Three days later, under voltage clamp, currents were measured in response to the application of 100 µM tyramine (FIG. 16). These currents were dependent upon co-expression of the CFTR ion channel, suggesting that they were caused by a receptor mediated elevation of cAMP. Thus, the human homolog, hSNORF33, is a functional receptor strongly stimulated by tyramine.

Receptor Binding

Receptor binding was performed on rSNORF33- and mock-transfected COS-7 membranes using [³H]-TYR and [³H]-T as a radioligand described in the Materials and Methods.

Figure 13:
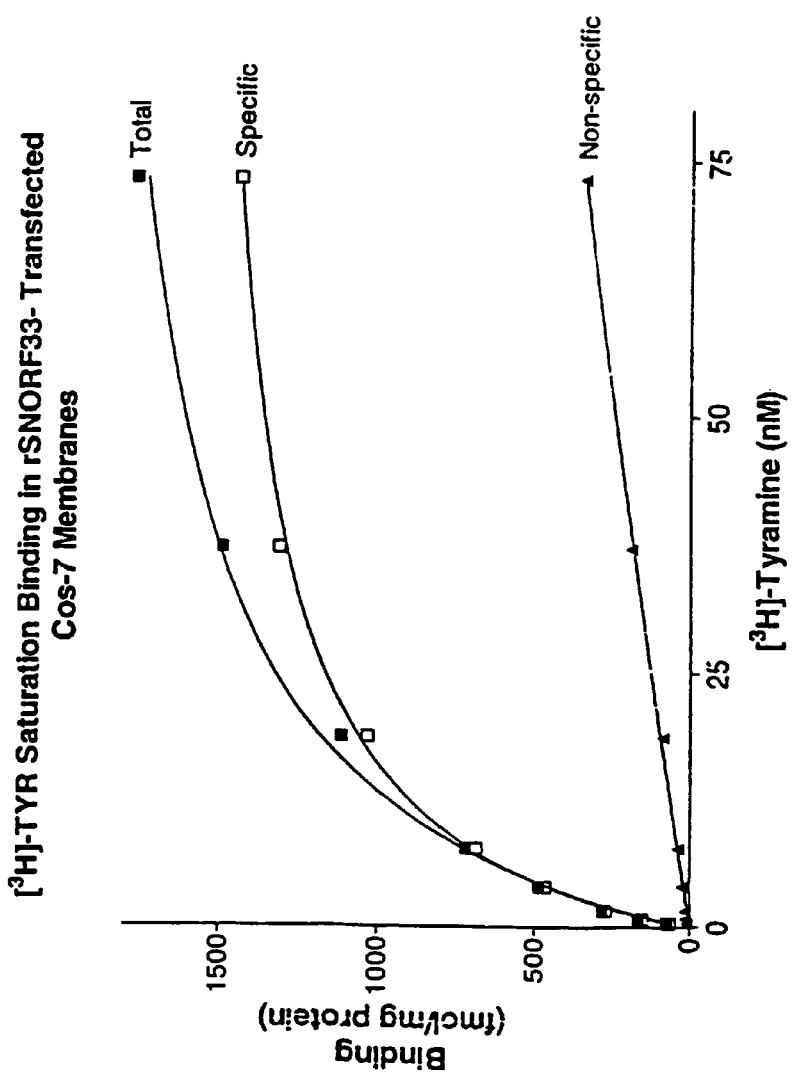
Figure 14:
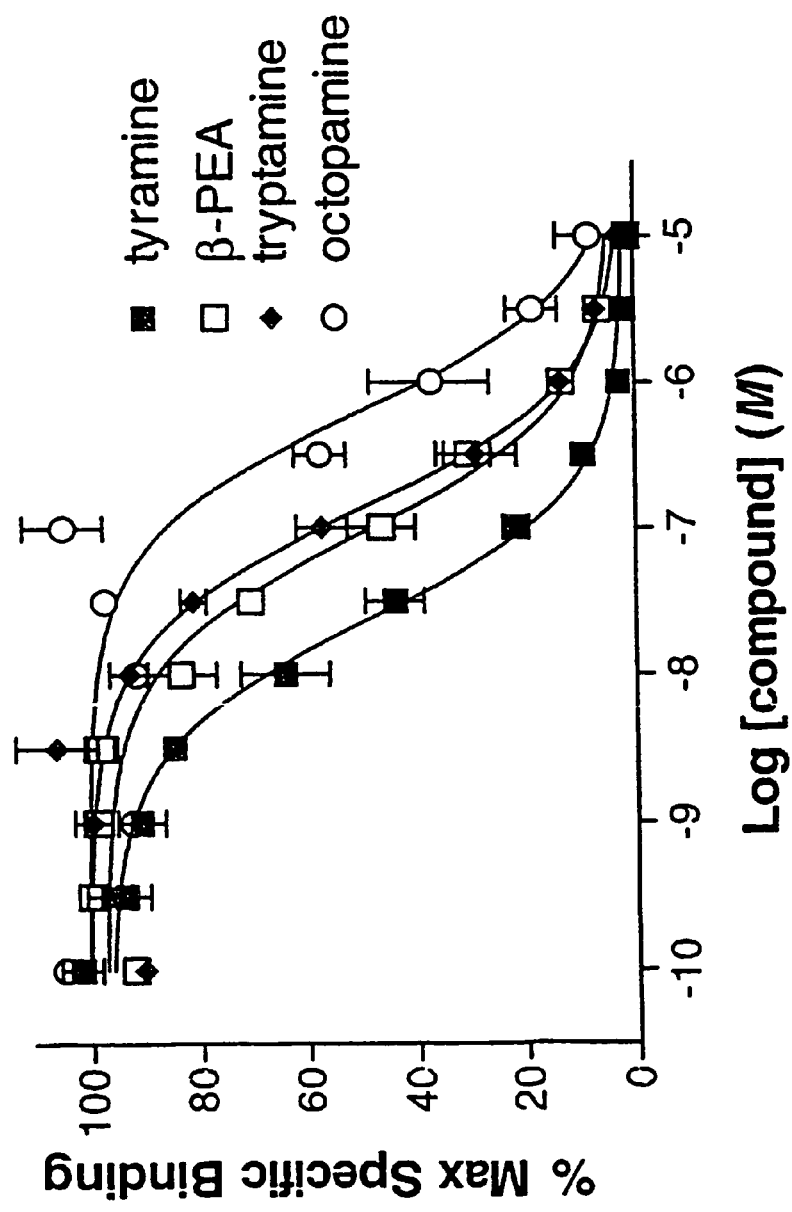

Binding of [³H]-TYR to the rSNORF33 membranes was saturable (FIG. 13) and of high affinity (Kd=12.5 and 14.8 nM, Bmax=1400 and 1164 fmol/mg protein, n=2). No specific binding sites were present in the mock-transfected membranes. Displacement of [³H]-TYR binding allowed the estimation of binding affinity of a number of compounds for rSNORF33 (FIG. 14 and Table 2). The Ki values obtained for compounds displacing [³H]-TYR binding were in good agreement with the potency values obtained for the compounds in the cAMP assay. The trace amines displaced [³H]-TYR binding with a rank order similar to that observed in the functional assays, TYR>β-PEA>T>OCT. In agreement with the results of the functional assay, the (R)-enantiomer of amphetamine demonstrated greater affinity for displacing binding of [³H]-TYR than the (S)-enantiomer.

Figure 15:
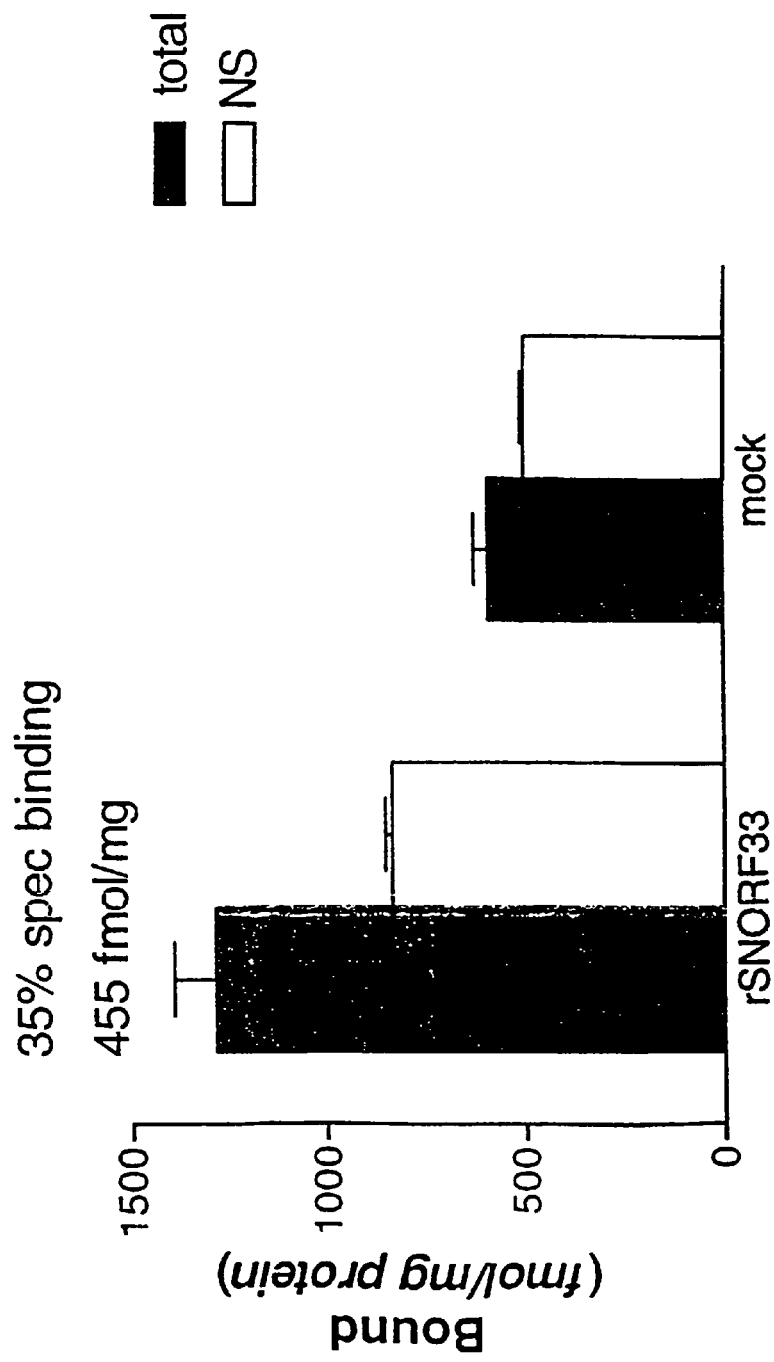

[³H]-T binding was also explored at the cloned rSNORF33. At 20 nM radioligand concentration, [³H]-T displayed much poorer binding signal (35% specific binding, FIG. 15) as compared with [³H]-TYR (90% specific binding at the same concentration, FIG. 13) on rSNORF33. This is consistent with both the weaker potency and affinity of T relative to TYR in functional (Table 1) and competition binding studies (Table 2), respectively.

In summary, the pharmacological profile of rSNORF33 described here using functional assays (cAMP release and the oocyte electrophysiological assay), shares several of the pharmacological properties of the TYR and T binding sites described in the literature, namely, relatively high affinity for TYR, PEA, T and kynuramine and low affinity for other classical neurotransmitters such as 5-HT, NE, DA and histamine. However, it is difficult to directly correlate the pharmacological profile of rSNORF33 with that obtained in the literature for the rat, since the cloning of a rat or mammalian TYR receptor has not been published as yet. Furthermore, the described TYR and T receptor pharmacology observed in the native systems may not be that of a single TYR or T receptor subtype but may comprise those of several subtypes, whereas drug responses mediated by rSNORF33 shown here are via a single cloned receptor transfected in a heterologous system devoid of any other endogenous TYR and T receptor responses. Moreover, correlation with the cloned TYR or OCT receptor from invertebrates may also be misleading since species differences in amino acid sequence may result in significant differences in the pharmacological profile (e.g. the pharmacological profile of the cloned *Drosophila* 5-HT receptor, 5-HT$_{Drol}$ (Witz et al., 1990) does not correlate with any of the known cloned or native mammalian 5-HT receptors). As more information becomes available the relationship between the cloned rat TYR receptor and native "trace amine" binding sites will be clarified.

Since both in functional and binding assays TYR shows the highest potency and affinity, respectively, among the trace amines studied, rSNORF33 is therefore being classified as a TYR receptor.

TABLE 2

Affinities for displacement of [³H]-tyramine at rSNORF33 in transfected COS-7 membranes

| Compound | Mean* Ki + S.D.M.# (nM) |
|---|---|
| tyramine | 13 ± 4 |
| tryptamine | 70 ± 14 |
| β-phenylethylamine | 56 ± 21 |
| (R)-amphetamine | 48 ± 28 |
| piperazine | 82 ± 14 |
| m-CPP** | 83 ± 25 |
| (S)-amphetamine | 226 ± 56 |
| 5-Methoxy-Tryptamine | 209 ± 68 |
| kynuramine | 485 ± 9 |
| methamphetamine | 391 ± 246 |
| octopamine | 310 ± 71 |
| 3-OH-PEA | 529 ± 236 |
| dopamine | 1154 ± 190 |
| serotonin (5-HT) | 976 ± 120 |

*calculated using results from 2–4 experiments
**m-CPP is 1-(3-chlorophenyl)piperazine dihydrochloride
S.D.M.; Standard Deviation of Mean Saturation Binding of [³H]-TYR to Mouse and Human SNORF33

Membranes from COS-7 cells expressing mouse SNORF33 and membranes expressing human SNORF33 were characterized for binding of [³H]-TYR as described in Materials and Methods. Binding of [³H]-TYR (0.4-84 nM) was time dependent and saturable for both receptors. The human SNORF33 membranes bound [³H]-TYR with Kd=27.9, 11.8 nM and Bmax 440, 603 fmol/mg protein. The mouse SNORF33 membranes bound [³H]-TYR with Kd=16.2, 7.3 nM and Bmax=1090, 848 fmol/mg protein. At —15 nM [³H]-TYR, specific binding accounted for approximately 94% and 70% of total binding for mouse and human SNORF33, respectively. No specific binding of [³H]-TYR was seen on membranes from mock-transfected cells (data not shown). Thus both mouse and human SNORF33 bind [³H]-TYR with high affinity similar to rat SNORF33 (FIG. 13), albeit expression of human SNORF33 is significantly less than the other species.

Displacement of [³H]-TYR binding allowed the estimation of binding affinity of a number of compounds for human SNORF33 (Table 3). Although human SNORF33 binds [³H]-TYR with high affinity, the rank order of affinity for the trace amines (β-PEA>TYR>OCT>T) was different from that observed for rat SNORF33. This difference is mainly due to the relatively low affinity of human SNORF33 for T (tryptamine) (Tables 2 and 3). The trace amine compounds also stimulated human SNORF33 receptors transiently expressed in COS-7 cells to induce a robust (approximately 7-fold) increase in intracellular cAMP (Table 4). Similar to the rank order of binding affinities, the potencies of the trace amine compounds at the human SNORF33 was β-PEA>TYR>OCT>T. For all of the compounds tested at human SNORF33, the EC50 values obtained from functional studies (Table 4) are significantly higher than the Ki values (binding affinities) derived from binding assays (Table 3). The human SNORF33 receptor may therefore not couple well to the activation pathways in COS-7 cells. However, the rank order of potency for the compounds listed in Table 4 is in agreement with their binding affinities at the human SNORF33 receptor.

Binding affinities (Ki values) were also determined for the trace amines at the mouse SNORF33 receptor: TYR (19 nM, 20 nM), β-PEA (19 nM, 47 nM) and T (140 nM, 140 nM). These compounds are also full agonists at mouse SNORF33 in the cAMP assay with the rank order of potency TYR=β-PEA>T. In addition, similar to their lack of interaction with the human SNORF33 receptor, m-CPP and piperazine also displace [3H]TYR weakly from mouse SNORF33 (average Ki values 3550 nM and 1950 nM, respectively n=2).

In addition to endogenous trace amine compounds, a number of biologically active, synthetic compounds interact with rat and human SNORF33 receptors (see Tables 1-4) including (R) amphetamine, (S) amphetamine and methamphetamine. Consistent with their anorectic activity in both rat and humans, these compounds demonstrate high affinity and potency at both the cloned rat and human SNORF33 receptors. The activity of these compounds at the cloned SNORF33 receptors indicates that SNORF33 is involved in anorectic functions.

Additional pharmacological differences between rat and human SNORF33 have been noted. m-CPP, an active metabolite of the antidepressant trazodone, binds with high affinity to rat SNORF33 (Ki=83 nM) while no displacement of [³H] TYR binding was seen at human SNORF33 up to 10 μM. Similarly, piperazine demonstrates high affinity for rat SNORF33 (Ki 82 nM), but not human SNORF33 (Ki>10 μM).

Cells Stably Expressing Rat SNORF33

Several stable rat SNORF33 clones with varying expression levels were created. One clone each in HEK293 and CHO cell hosts expressing —1600 and 300 fmol/mg protein, respectively, were isolated for further studies. The stable rat SNORF33/HEK293 cells demonstrated a robust increase in CAMP (—4-fold) in response to TYR (data not shown). The parent cell line (untransfected) showed no TYR-induced increase in cAMP.

TABLE 3

Affinities for displacement of [³H]-tyramine at human SNORF33 in transfected COS-7 membranes

| Compound | Mean* Ki ± S.D.M.# (nM) | n |
|---|---|---|
| β-phenylethylamine | 8 ± 6 | 4 |
| (R)-amphetamine | 39 ± 16 | 3 |
| tyramine | 51 ± 11 | 3 |
| (S)-amphetamine | 57 ± 36 | 3 |
| 3-OH-PEA | 79 ± 16 | 2 |
| methamphetamine | 189 ± 102 | 3 |
| octopamine | 417 ± 285 | 2 |
| dopamine | 422 ± 11 | 2 |
| tryptamine | 1133 ± 372 | 3 |
| kynuramine | 1395 ± 810 | 3 |
| m-CPP* | >10 μM | 2 |
| piperazine | >10 μM | 2 |

*m-CPP is 1-(3-chlorophenyl)piperazine dihydrochloride

TABLE 4

Agonist Potencies For Stimulation Of human SNORF33 Receptors As Measured By Intracellular cAMP Release In SNORF33-Transfected COS-7 Cells.

| Compound | Mean EC50 ± S.D.M. (nM) | n |
|---|---|---|
| β-phenylethylamine | 216 ± 149 | 5 |
| (R)-amphetamine | 378 ± 182 | 3 |
| tyramine | 214 ± 85 | 4 |
| (S)-amphetamine | 249 ± 66 | 3 |
| octopamine | 4093 ± 95 | 2 |
| tryptamine | 24,000 ± 3000 | 2 |

Detection of mRNA Coding for Human SNORF33 mRNA was isolated from multiple tissues (listed in Table 5) and assayed as described. Quantitative RT-PCR using a fluorgenic probe demonstrated expression of mRNA encoding human SNORF33 in most tissues assayed (Table 5). Highest levels of human SNORF33 mRNA are found in the kidney, stomach, fetal kidney, small intestine, and fetal lung. Most nervous system structures showed little expression of SNORF33 mRNA as compared to peripheral organs. The notable exception to this is the level of SNORF33 mRNA detected in the amygdala, where mRNA levels are 19% of those detected in the highest expressing tissue, the kidney. Other regions of the human CNS expressing lower levels of SNORF33 mRNA include the hippocampus, the substantia nigra as well as other regions listed in Table 5.

The high levels of human SNORF33 RNA expressed in kidney implicate it in electrolyte regulation and potentially hypertension. It is not known at this time at what site(s) in the kidney this receptor exerts its effects.

Other organs with high levels of SNORF33 mRNA are stomach, and small intestine. The localization to these structures is consistent with functions relating to gastrointestinal motility or absorption. It is not known at this time if human SNORF33 mRNA is localized to ganglion cells, smooth muscle or to mucosal/submucosal layers. Although detected in low levels, the presence of SNORF33 mRNA in multiple regions of the CNS including the amygdala (where levels are highest in the CNS) imply a role in modulating fear, phobias and depression. Its presence in other functionally diverse areas, implies a diffuse regulatory function or regional functionality for this receptor.

Human SNORF33 mRNA appears to be developmentally regulated in the lung. There is an 18-fold decrease in mRNA encoding human SNORF33 in adult lung as compared to fetal tissue. This implicates human SNORF33 as a potential factor involved in the growth and/or maturation of lungs. The time course of this increase has not been examined and would be important in understanding the function of this receptor.

In summary, the distribution of human SNORF33 mRNA implies renal and gastrointestinal regulatory functions. Its presence in the amygdala suggests modulatory function involving depression and mood disorders. Other CNS structures, although containing low levels of SNORF33 mRNA imply a broad regulatory function in the CNS.

Detection of mRNA Coding for Rat SNORF33

The tissue showing the highest levels of SNORF33 mRNA is the testes (Table 6). Levels in the testes are more than ten fold higher than any other tissue (see Table 6). This strongly suggests a role in endocrine regulation or reproductive function.

Dorsal root ganglia are the second highest expressing tissues, expressing 8% of the amount found in the testes. The thalamus, spinal cord and the medulla contain lower levels of SNORF33, however, they are the highest levels detected in the CNS. The presence of SNORF33 mRNA in primary sensory neurons, and these CNS regions suggests a modulatory role in pain or sensory transmission. Additionally, it may play a role in modulating autonomic centers present in the medulla.

Rat SNORF33 mRNA is also detected in the gastrointestinal tract. It is detected in the stomach, duodenum, and colon. As in the human, the localization to these structures is consistent with functions relating to gastrointestinal motility or absorption. Detailed localization using in situ hybridization in the stomach have been completed and a description follows. Other areas assayed expressing SNORF33 RNA include adipose tissue, kidney, urinary bladder, liver, lung, pancreas and other areas (see Table 6).

Adipose tissue is the third highest-expressing tissue in the periphery (testes and stomach being the two highest expressing in the periphery), showing 2% of the amount found in the testes.

In summary, the localization of high levels of SNORF33 to the rat testes suggests a role in reproductive function or endocrine regulation. The high levels present in the dorsal root ganglia, along with detectable levels in the spinal cord, thalamus and medulla strongly suggest a role in sensory transmission. As in the human, there is a suggestion of renal and gastrointestinal regulatory functions. The presence of SNORF33 mRNA in adipose tissue and its coupling to stimulation of cAMP, suggests that this receptor may increase lipolysis, fat mobilization and metabolism, resulting in reduction in body weight, analogous to the action of other cAMP-stimulatory receptors (e.g. $\beta_3$-adrenergic on this tissue.

Other peripheral organs and CNS structures, although containing low levels of SNORF33, mRNA imply a broad regulatory role for this receptor.

Detection of mRNA Coding for Mouse SNORF33

A limited panel of tissue dissected from mice (Table 7) was assayed to detect the presence of SNORF33 RNA. Highest levels of SNORF33 RNA in mice are found in stomach. Other organs expressing high levels of SNORF33 are the hypothalamus, liver, amygdala and medulla (Table 7). There are considerable differences in the relative levels of SNORF 33 among the three species assayed. In fact, the only tissue expressing high levels of SNORF33 RNA in all three species is the stomach. One region with the most notable differences is the kidney. The human kidney expresses highest levels of SNORF33 assayed. In contrast, rat and mouse kidney, express low, although detectable, levels of SNORF33 RNA. Other species differences are shown in Table 7.

Chromosomal Localization of Human SNORF33

Human SNORF33 has been placed on SHGC-1836 which maps to chromosome 6q21. This places SNORF33 near other GPCRs expressed on chromosome 6 including: PNR, 5-HT4 pseudogene, GPR58, GPR57, GPR6 and the neuromedin B receptor.

TABLE 5

Distribution of mRNA coding for human SNORF33 receptors using qRT-PCR
mRNA encoding human SNORF33 is expressed as % of highest expressing tissue, kidney.

| Region | qRT-PCR % of max | Potential applications |
| --- | --- | --- |
| heart | 1.19 | Cardiovascular indications |
| kidney | 100 | Hypertension, electrolyte balance |
| liver | 9.71 | Diabetes |
| lung | 2.45 | Respiratory disorders, asthma |
| pancreas | 1.34 | Diabetes, endocrine disorders |
| pituitary | 2.04 | Endocrine/neuroendocrine regulation |
| placenta | 0.44 | Gestational abnormalities |
| small intestine | 44.22 | Gastrointestinal disorders |
| spleen | 1.98 | Immune disorders |
| stomach | 88.02 | Gastrointestinal disorders |
| striated muscle | 4.3 | Musculoskeletal disorders |
| amygdala | 19.18 | Depression, phobias, anxiety, mood disorders |
| caudate-putamen | 0.55 | Modulation of dopaminergic function |
| cerebellum | 2.04 | Motor coordination |
| hippocampus | 3.28 | Cognition/memory |

TABLE 5-continued

Distribution of mRNA coding for human SNORF33 receptors using qRT-PCR
mRNA encoding human SNORF33 is expressed as % of highest expressing tissue, kidney.

| Region | qRT-PCR % of max | Potential applications |
|---|---|---|
| hypothalamus | not detected | Appetite/obesity, neuroendocrine regulation, |
| spinal cord | 1.05 | Analgesia, Sensory Modulation and Transmission, Modulation of Autonomic Function |
| substantia nigra | 3.06 | Modulation of dopaminergic function. Modulation of motor coordination. |
| thalamus | Not detected | Sensory integration disorders |
| whole brain | 0.41 | |
| fetal brain | 1.34 | Developmental disorders |
| fetal lung | 42.98 | Developmental disorders |
| fetal kidney | 63.64 | Developmental disorders |
| fetal liver | 5.12 | Developmental disorders |

TABLE 6

Summary of distribution of mRNA coding for rat SNORF33 receptors
mRNA encoding rat SNORF33 is expressed as % of highest expressing tissue (testes).

| Tissue | qRT-PCR % of max | Potential applications |
|---|---|---|
| adipose | 2.05 | metabolic disorders |
| adrenal cortex | not detected | regulation of steroid hormones |
| adrenal medulla | not detected | regulation of epinephrine release |
| amygdala | 0.05 | depression, phobias, anxiety, mood disorders |
| aorta | 0.07 | cardiovascular indications |
| celiac plexus | 0.49 | modulation of autonomic function |
| cerebellum | trace | motor coordination |
| cerebral cortex | not detected | Sensory and motor integration, cognition |
| choroid plexus | trace | regulation of cerebrospinal fluid |
| colon | 0.91 | gastrointestinal disorders |
| dorsal root ganglia | 7.58 | sensory transmission |
| duodenum | 1.80 | gastrointestinal disorders |
| heart | 0.06 | cardiovascular indications |
| hippocampus | not detected | cognition/memory |
| hypothalamus | 0.10 | appetite/obesity, neuroendocrine regulation |
| kidney | 0.05 | electrolyte balance, hypertension |
| liver | 0.32 | diabetes |
| lung | 0.21 | respiratory disorders, asthma |
| medulla | 0.71 | analgesia, modulation of autonomic function, sensory transmission and modulation |
| nucleus accumbens | not detected | regulation of dopaminergic function, drug addiction, neuropsychiatric disorders |
| olfactory bulb | 0.05 | olfaction |
| ovary | Trace | reproductive function |
| pancreas | 0.09 | diabetes, endocrine disorders |
| pineal | trace | regulation of melatonin release |
| pituitary | not detected | endocrine/neuroendocrine regulation |
| retina | 0.10 | visual disorders |
| spinal cord | 0.27 | analgesia, sensory modulation and transmission |
| spleen | 0.05 | immune disorders |
| stomach | 6.92 | gastrointestinal disorders |
| striated muscle | 0.1 | musculoskeletal disorders |
| striatum | not detected | modulation of dopaminergic function, motor disorders |
| substantia nigra | not detected | modulation of dopaminergic function, modulation of motor coordination |
| testes | 100 | reproductive function |
| thalamus | 5.80 | sensory integration disorders |
| thymus | 0.23 | immune disorders |
| trigeminal ganglia | not detected | sensory transmission |
| urinary bladder | 0.76 | urinary incontinence |
| uterus | not detected | reproductive disorders |
| vas deferens | 0.27 | reproductive function |

TABLE 7

Comparison of mRNA levels coding for human, rat and mouse SNORF33 RNA
To facilitate comparison, levels of SNORF33 RNA are expressed as % of RNA detected in stomach.

| | % of stomach | | |
|---|---|---|---|
| Tissue | rat | mouse | human |
| adipose | 31.09 | 0.94 | not assayed |
| amygdala | 0.92 | 23.14 | 21.69 |
| cerebellum | trace | 1.19 | 2.25 |
| cerebral cortex | 0.00 | 3.50 | not assayed |
| heart | 0.90 | 0.54 | 1.41 |
| hypothalamus | 1.50 | 24.58 | not detected |
| kidney | 0.74 | 0.43 | 113.52 |
| liver | 4.68 | 58.05 | 10.99 |
| lung | 3.05 | 11.11 | 2.82 |
| medulla | 10.10 | 36.03 | not assayed |
| stomach | 100.00 | 100.00 | 100.00 |
| testes | 1426.05 | 3.04 | not assayed |

In Situ Hybridization Experiments for SNORF33 mRNA

The expression of SNORF33 mRNA was examined in a variety of selected rat peripheral tissues, namely, lung, stomach, spleen, liver, kidney, and testes. The kidney and testes were devoid of any hybridization signal for SNORF33 mRNA.

Throughout the body of the stomach a moderate hybridization signal for SNORF33 mRNA was detected over enteric ganglion cells within the muscularis layer located between the outer longitudinal and inner circular layers. A moderate signal was also observed to be related to the cells lining the lumen of the stomach.

[$^3$H]-T binding sites have been reported to be present in the stomach fundus (Brüning and Rommelspacher, 1984). Several 5-HT receptor subtypes have been pharmacologically identified in the rat enteric ganglia, and/or stomach fundus, namely 5-HT$_{2B}$, 5-HT$_3$, 5-HT$_4$ and 5-HT$_{1P}$ and all of these except 5-HT$_{1P}$, have been cloned. The pharmacological profile of SNORF33 does not match the profile of any of these receptors (Table 1, FIG. 12 and Boess and Martin, 1994). These data support the existence of multiple neuronal target sites for "trace amines" in the stomach fundus and suggest a 5-HT-independent effect for "trace amines" on stomach.

In the spleen, cells positive for SNORF33 mRNA were observed to be located primarily in the red pulp and around the marginal zone of the white pulp. Silver grains were detected over monocytes and scattered eosinophils. Monocytes present in the blood are sequestered in the spleen where they are transformed into macrophages and maintain their phagocytic activity in the spleen. Monocytes that have been removed from the circulation are isolated in the white pulp, the marginal zone and the red pulp. Monocyte/macrophages are active in pinocytosis and phagocytosis. They are involved in the production of antibodies and in cell-mediated immune responses, for example transplant rejections and delayed hypersensitivity reactions. Macrophages are involved in processing and presenting an antigen to lymphocytes thus triggering the proliferation of T- and B-lymphocytes. Eosinophils are motile phagocytotic granulocytes that may also be stored in the spleen. Eosinophils normally constitute 2 to 4% of the circulating white blood cells with a distinctive function in that they kill the larvae of parasites. In the rat, eosinophils are released from the blood to the spleen where they finalize their maturation before they enter the general circulation or can be stored and rapidly delivered to the circulation when needed.

The infusion of T through the pulmonary circulation of isolated lungs of the rat results in the release of a spasmogen resembling slow reacting substance of anaphylaxis and a PGE-like activity. The pharmacology of the release receptor was shown to closely resemble T receptors in the rat stomach strip (Bakhle et al., 1977). The localization of SNORF33 mRNA in the lung appeared to be restricted to monocytes. In the lung's alveolar interstitium there is a resident macrophage population, in addition to scavenging alveolar macrophages moving through the alveolar fluid along the epithelial surface, which keeps the lung clear of pathogens.

SNORF33 mRNA was identified in scattered monocytes throughout the parenchyma of the liver. The liver is essential for life and it functions as an endocrine and exocrine gland, during certain diseases it is a site of hematopoesis. The liver contains an abundance of phagocytes and is a principal filter for foreign particulate matter, especially bacteria from the alimentary tract.

The identification of SNORF33 mRNA in leucocytes in the above mentioned peripheral tissues suggests a potential role for this receptor as part of the host defense and immune systems of the body.

Overall, the results of the localization studies using in situ hybridization and quantitative RT-PCR are in agreement. In situ hybridization histochemistry demonstrates SNORF33 (rat) present in enteric ganglion cells as well as mucosal cells in the stomach. Other areas expressing SNORF33 mRNA include immune cells in the spleen, lung, and stomach. Quantitative RT-PCR detected SNORF33 mRNA in these areas, as well as others. The broader distribution of rat SNORF33 mRNA using quantitative RT-PCR reflects higher sensitivity of quantitative RT-PCR, with the concomitant loss of information regarding tissue architecture. Regional expression patterns within a tissue affect visualization of mRNA using in situ hybridization. If the SNORF 33 mRNA is distributed diffusely throughout a broad area it is less likely to be detected by in situ hybridization. In contrast, if a tissue has low levels of SNORF33 RNA concentrated in a restricted area, in situ will be able detect this RNA with a high degree of anatomical precision.

TABLE 8

Rat and mouse SNORF33 mRNA distribution in the CNS using in situ Hybridization with digoxigenin-labeled riboprobes.

| Region | Mouse | Rat | Potential Application |
|---|---|---|---|
| Olfactory bulb | | | Modulation of olfactory sensation |
| internal granule layer | + | + | |
| glomerular layer | + | + | |
| external plexiform layer | + | + | |
| mitral cell layer | +++ | − | |
| anterior olfactory n | + | + | |
| olfactory tubercle | + | + | |
| islands of Calleja | − | − | |
| Telencephalon | | | Sensory integration |
| taenia tecta | + | + | |
| frontal cortex | ++ | + | |
| orbital cortex | + | − | |
| agranular insular cortex | ++ | + | |
| anterior cingulate cortex | + | + | |
| retrosplenial cortex | + | + | |
| parietal cortex | + | + | Processing of visual stimuli |
| occipital cortex | + | + | |
| temporal cortex | + | + | Processing of auditory stimuli |
| entorhinal cortex | ++ | + | Processing of visceral information |
| dorsal endopiriform n | + | − | |
| horizontal diagonal band | ++ | + | |
| piriform cortex | +++ | ++ | Integration/transmission of incoming olfactory information |
| Basal Ganglia | | | |
| accumbens n | + | + | Modulation of dopaminergic function |
| caudate-putamen | + | + | Sensory/ motor integration |
| globus pallidus | − | − | |
| entopeduncular n | + | − | |
| Septum | | | |
| medial septum | + | + | Cognitive enhancement via cholinergic system |
| lateral septum, dorsal | + | + | Modulation of integration of stimuli associated with adaptation |
| lateral septum, intermediate | + | + | |
| ventral pallidum | ++ | + | |
| Amygdala | | | Anxiolytic (activation - reduction in panic attacks) appetite, depression |

TABLE 8-continued

Rat and mouse SNORF33 mRNA distribution in the CNS using in situ Hybridization with digoxigenin-labeled riboprobes.

| Region | Mouse | Rat | Potential Application |
|---|---|---|---|
| lateral n | + | ND | |
| basolateral n | + | + | |
| medial amygdaloid n | + | − | Olfactory amygdala |
| basomedial n | + | − | |
| central n | − | − | |
| anterior cortical n | + | + | |
| posteromedial cortical n | + | + | |
| bed n stria terminalis | + | + | |
| Hippocampus | | | Memory consolidation and retention |
| CA1, Ammon's horn | + | − | |
| CA2, Ammon's horn | − | − | |
| CA3, Ammon's horn | + | − | Facilitation of LTP |
| subiculum | + | + | |
| parasubiculum | − | − | |
| presubiculum | − | − | |
| dentate gyrus | ++ | + | |
| polymorph dentate gyrus | + | + | |
| Hypothalamus | | | |
| magnocellular preoptic n | + | + | |
| median preoptic n | + | | |
| median preoptic area | − | + | Regulation of gonadotropin secretion and reproductive behaviors |
| suprachiasmatic n | ND | + | Circadian rhythm |
| perifornical area | + | ND | Appetite/obesity |
| paraventricular n | ++ | + | Appetite/obesity |
| arcuate n | ++ | + | Appetite/obesity |
| anterior hypoth | + | + | Appetite/obesity |
| lateral hypothalamus | + | + | Appetite/obesity |
| dorsomedial n | + | + | Appetite/obesity |
| ventromedial n | + | + | Appetite/obesity |
| periventricular n | + | + | Endocrine regulation |
| supraoptic n | ++ | − | Synthesis of oxytocin and arginine vasopressin |
| medial mammillary n | + | + | |
| Thalamus | | | Analgesia/Modulation of sensory information |
| paraventricular n | ++ | + | Modulation of motor and behavioral responses to pain |
| paratenial n | ND | + | |
| centromedial n | ++ | − | Modulation of motor and behavioral responses to pain |
| paracentral n | + | + | |
| anterodorsal n | + | + | Modulation of eye movement |
| mediodorsal n | + | + | Modulation of information between limbic structures of the ventral forebrain and prefrontal cortex |
| laterodorsal n | + | + | |
| reuniens n | − | − | Modulation of thalamic input to ventral hippocampus and entorhinal cortex |
| reticular thalamic n | ++ | ND | Alertness/sedation |
| rhomboid n | + | − | |
| medial habenula | + | + | Anxiety/sleep disorders/analgesia in chronic pain |
| lateral habenula | + | + | |
| ventrolateral n | + | + | Nociception |
| ventromedial n | + | − | Nociception |
| ventral posterolateral n | ++ | − | Nociception |
| zona incerta | + | − | |
| medial geniculate | + | + | Modulation of auditory system |
| Mesencephalon | | | |
| superior colliculus | + | + | Modulation of vision |
| inferior colliculus | + | + | |
| central gray | + | − | Nociception |
| dorsal raphe | + | + | |
| mesencephalic trigeminal n | ++ | + | |
| trochlear n | ++ | ND | |
| oculomotor n | | + | |
| red n | + | + | |
| ventral tegmental area | + | + | Modulation of the integration of motor behavior and adaptive responses |
| substantia nigra, reticular | + | − | Motor control |
| substantia nigra, compact | + | + | |
| interpeduncular n | ND | + | Nociception |
| Myelencephalon | | | Nociception |
| raphe magnus | + | − | |
| raphe pallidus | + | + | |
| principal trigeminal | + | ND | Nociception |
| spinal trigeminal n | + | + | Nociception |
| pontine reticular n | + | + | |
| lateral reticular n | +++ | + | |
| parvicellular reticular n | − | + | |
| locus coeruleus | + | − | Modulation of NA transmission |
| parabrachial n | + | + | Modulation of visceral sensory information |
| Barrington = s n | + | ND | |
| motor trigeminal n | +++ | ND | |
| medial vestibular n | + | + | Maintenance of balance and equilibrium |
| spinal vestibular n | + | + | |
| trapezoid n | + | + | |

TABLE 8-continued

Rat and mouse SNORF33 mRNA distribution in the CNS using in situ Hybridization with digoxigenin-labeled riboprobes.

| Region | Mouse | Rat | Potential Application |
|---|---|---|---|
| external cuneate n | + | + | Medullary somatosensory relay nucleus. Receives collaterals of primary afferents from DRG cells |
| gigantocellular reticular n | ++ | + | Inhibition and disinhibition of brainstem |
| prepositus hypoglossal n | ND | + | Position and movement of the eyes/ Modulation of arterial pressure and heart rate |
| nucleus soltary tract | + | + | Hypertension |
| gracile n | + | ND | |
| 10 or dorsal motor n | +++ | + | |
| 12 or hypoglossal n | +++ | + | Modulation of proprioceptive information from jaw muscles, mastication. Oromotor nucleus |
| ambiguus n | ++ | + | Medullary motor nucleus |
| A5 noradrenaline cells | ND | – | |
| 7 or facial n | + | + | Oromotor nucleus |
| inferior olivary n | + | + | |
| Cerebellum | | | Motor coordination Autism |
| granule cells | + | + | |
| Purkinje cells | +++ | + | |
| molecular layer | + | + | |
| Deep cerebellar nuclei | + | – | |
| Spinal cord | | | Analgesia |
| dorsal horn | + | + | |
| lamina X | + | + | |
| ventral horn | ++ | – | |
| Circumventricular organs | | | |
| subfornical organ | + | + | |
| area postrema | ND | + | |

The strength of the hybridization signal for each of the respective mRNAs obtained in various regions of the rat and mouse brain was graded as absent (–), weak (+), moderate (++), or intense (+++).
ND = not determined Results of Localization Controls The specificity of the hybridization of the rat and mouse SNORF33 riboprobes was verified by performing in situ hybridization on transiently transfected COS-7 cells as described in Methods for tissue sections. The results indicate that the hybridization of rat and mouse riboprobes was selective for the SNORF33 mRNA. Specifically, the rat and mouse SNORF33 antisense riboprobes hybridized only to the COS-7 cells transfected with rat and mouse SNORF33 cDNA, respectively. The rat and mouse sense riboprobes did not hybridize to their respective cDNAs, and neither antisense nor sense riboprobes hybridized to the mock-transfected cells.

In the tissue sections, the rat and mouse antisense riboprobes resulted in a hybridization signal. No hybridization signal was observed in the tissues when the rat and mouse sense riboprobes were used.

Localization of SNORF33 mRNA in Rat CNS

The anatomical distribution of SNORF33 receptor mRNA in the rat and mouse CNS was determined by in situ hybridization using digoxigenin-labeled riboprobes. The low levels of SNORF33 mRNA expression in the rat brain required enzymatic amplification through use of the TSA Biotin System. The higher level of SNORF33 mRNA expression in the mouse brain did not require use of the amplification system, thus direct immunodetection of the digoxigenin-labeled riboprobe was performed. By light microscopy the chromogen precipitate (DAB (brown color) for the rat or BCIP (blue color) for the mouse), was observed to be distributed in the cytoplasm of neuronal profiles. The results demonstrate that the mRNA for the SNORF33 receptor is widely distributed throughout the rat and mouse CNS (Table 8). The expression of mouse SNORF33 mRNA was determined to be more extensive than the rat expression. As a result of the lower level of SNORF33 mRNA expression in the rat CNS, and possible technical limitations of the in situ hybridization technique the distribution of rat SNORF33 mRNA may have been underestimated in some regions of the brain.

Throughout the rat brain SNORF33 mRNA expression levels were weak and fairly uniform in intensity. SNORF33 mRNA was detectable in the olfactory bulb, the cerebral cortex, septum, basal ganglia, hypothalamus, thalamus, mesencephalic nuclei, the brain stem, cerebellum and the spinal cord. Alternatively, the expression of SNORF33 mRNA in the mouse brain was not uniform, with several regions exhibiting higher expression levels, specifically, the mitral cell layer of the olfactory bulb, piriform cortex, dorsal motor nucleus of vagus, motor trigeminal nucleus, cerebellar Purkinje cells, lateral reticular nucleus, and ventral horn of the spinal cord. Moderate expression was observed in the frontal, entorhinal and agranular cortices, the ventral pallidum, the thalamus, the hypothalamus, the hypoglossal ambiguus and the gigantocellular reticular nuclei. Lower expression levels of SNORF33 mRNA were detected in the septum, basal ganglia, amygdala, myencephalon, and the dorsal horn of the spinal cord.

The distribution and expression levels of SNORF33 mRNA in selected regions of rat and mouse CNS by in situ hybridization is in concordance with the reported qRT-PCR data (Tables 6 and 8). Notable exceptions were in the rat cerebral cortex and the cerebellum where SNORF33 mRNA was detected by in situ hybridization but not by qRT-PCR.

Discussion

The SNORF33 receptor could potentially play a role in mediating a variety of physiological processes. One possible role for the SNORF33 receptor might be in modulating sensory information as suggested by the in situ hybridization experiments which identified the expression of SNORF33 receptor mRNA in the relay nuclei of several sensory pathways, specifically the olfactory and visual pathways.

Another indication for the SNORF33 receptor might be the ability to modulate nociceptive information because of the presence of SNORF33 transcripts in somatic sensory neurons of the trigeminal complex and dorsal root ganglia (Table 6) and also in the target regions of nociceptive primary afferent fibers, including the superficial layers of the spinal trigeminal nucleus and dorsal horn of the spinal cord. Again, in each of these loci the SNORF33 might be in a position to potentially modulate the influence of incoming excitatory nociceptive primary afferents.

Another conceivable role for the SNORF33 receptor may be in modulating the integration of motor behavior and adaptive responses resulting from the localization of SNORF33 mRNA in the Basal Ganglia and the ventral tegmental area.

SNORF33 receptor mRNA was identified in several regions of the cerebellar circuit. SNORF33 transcripts were observed in the inhibitory GABAergic Purkinje cells, the red nucleus, the reticular formation and the ventral nuclei of the thalamus, suggesting that the SNORF33 receptor may be important in mediating planned movements.

The expression of SNORF33 receptor transcripts throughout the telencephalon suggests a potential modulatory role in the processing of somatosensory and limbic system (entorhinal cortex) information, in addition to modulating visual (parietal cortex) and auditory stimuli (temporal cortex) as well as cognition. Furthermore, modulation of patterns of integrated behaviors, such as defense, ingestion, aggression, reproduction and learning could also be attributed to this receptor owing to its expression in the amygdala.

The expression in the thalamus suggests a possible regulatory role in the transmission of somatosensory (nociceptive) information to the cortex and the exchange of information between the forebrain and midbrain limbic system (habenula).

The presence of SNORF33 receptor mRNA in the hypothalamus suggests a potential modulatory role in food intake, reproduction, the expression of emotion and possibly neuroendocrine regulation.

REFERENCES

Altar, C. A. et al., "Autoradiographic localisation and pharmacology of unique [3H]-tryptamine binding sites in rat brain", *Neurosci.* 17: 263-273 (1986).

Armstrong, M. D. and Robinson, K. S., "On the excretion of indole derivatives in phenylketonuria", *Arch. Biochem. Biophys.* 52: 287-290 (1954).

Artigas, F. and Gelpi, E., "A new mass fragmentographic method for the simultaneous analysis of tryptophan, tryptamine, indole-3-acetic acid, serotonin and 5-hydroxyindole-3-acetic acid in the same sample of rat brain", *Anal. Biochem.* 92: 233-242 (1979).

Axelrod, J. and Saavedra, J. M., "Octopamine, phenylethanolamine, phenylethylamine and tryptamine in the brain", In *Aromatic Amino Acids in the Brain*, Ciba Foundation Symposium 2 (New Series), Elsevier-Excerpta Medica, North-Holland, Amsterdam, pp. 51-59 (1974).

Axelrod, J. and Saavedra, J. M., "Octopamine", *Nature, Lond.* 265: 501-504 (1977).

Baker, G. B. and Dyck, L. E., "Neuronal transport of amines in vitro" In *Neuromethods Vol. 2: Amines and their Metabolites* (Boulton, A. A. et al., Eds.), pp. 457-534. Humana Press, Clifton, N.J. (1985).

Baker, G. B. et al., "Trace amines and Tourette's syndrome", *Neurochem. Res.* 18: 951-956 (1993).

Bakhle, Y. S. and Smith, T. W., "Release of spasmogens from rat isolated lungs by tryptamines", *Eur. J. Pharmac.* 46: 31-39 (1977).

Barchas, J. D. et al., "Tryptolines: Formation from tryptamine and 5MTHF by human platelets" *Arch. Gen. Psychiat.* 174: 862-865 (1974).

Baron, D. N. et al., "Hereditary pellagra-like skin rash with temporary cerebellar ataxia, constant renal amino-aciduria, and other bizarre biochemical features", *Lancet* 271: 421-423 (1956).

Bennett, J. P. and Gardiner, S. M., "Corticosteroid involvement in the changes in noradrenergic responsiveness of tissues from rats made hypertensive by short-term isolation", *Br. J. Pharmacol.* 64: 129-136 (1978).

Biegon, A. et al., "Quantitative autoradiography of serotonin receptors in the rat brain", *Brain Res.* 242: 197-204 (1982).

Boess, F. G. and Martin, I. L., "Molecular biology of 5-HT receptors", *Neuropharmacol.* 33: 275-317 (1994).

Boulton, A. A. and Baker, G. B., "The subcellular distribution of β-phenylethylamine, p-tyramine and tryptamine in rat brain", *J. Neurochem.* 25: 477-481 (1975).

Boulton, A. A., "Cerebral aryl alkyl aminergic mechanisms", In *Trace Amines in the Brain*, (Usdin, E. and Sandler, M. Eds.), Macel Dekker, New York (1976).

Bradford, M. M., "A rapid and sensitive method for the quantitation of microgram quantities of protein utilizing the principle of protein-dye binding", *Anal. Biochem.* 72: 248-254 (1976).

Brune, G. G. and Himwhich, H. E., "Indole metabolites in schizophrenic patients", *Arch. Gen. Psychiat.* 6: 324-328 (1962).

Brüning, G. and Rommelspacher, H., "High affinity [3H] tryptamine binding sites in various organs of the rat", *Life Sci.* 34: 1441-1446 (1984).

Burns, C. C., et al., "Identification and deletion of sequences required for feline leukemia virus RNA packaging and construction of a high-titer feline leukemia virus packaging cell line", *Virology* 222(1): 14-20 (1996).

Bush, et al., "Nerve growth factor potentiates bradykinin-induced calcium influx and release in PC12 cells", *J. Neurochem.* 57: 562-574 (1991).

Cascio, C. S. and Kellar, K. J., "Characterization of [3H] tryptamine binding sites in brain", *Eur. J. Pharmacol.* 95: 31-39 (198.3).

Cohen, M. L. and Wittenauer L. A., "Relationship between serotonin and tryptamine receptors in the rat stomach fundus", *J. Pharmacol. Exp. Ther.* 223: 75-79 (1985).

Coppen, A. et al., "Tryptamine metabolism in depression", *Br. J. Psychiat.* 111: 993-998 (1965).

Cox, B. and et al., "A role for an indolamine other than 5-hydroxytryptamine in the hypothalamic thermoregulatory pathways of the rat", *J. Physiol.* 337: 441-450 (1983).

Cox, B. et al., "Different hypothalamic receptors mediate 5-HT and tryptamine-induced core temperature changes in the rat", *Br. J. Pharmac.* 72: 477-482 (1981).

Dascal, N., et al., "A trial G protein-activated $K^+$ channel: expression cloning and molecular properties", *Proc. Natl. Acad. Sci. USA* 90: 10235-10239 (1993).

David, J.-C. and Coulon, J.-F., "Octopamine in invertebrates and vertebrates: a review", *Prog. Neurobiol.* 24: 141-185 (1985).

David, J. C., "Age variation in the increase of hypothalamic and brain stem contents of phenylethanolamine, m-octopamine and p-octopamine in spontaneously hypertensive rats (SHR Kyoto)", *Experientia* 35: 1483-1484 (1979).

David, J. C., "Augmentation des taux de phenylethanolamine, m-octopamine et p-octopamine au niveau de l'hypothalamus et du tronc cerebral de rats genetiquement hypertendus (SHR Kyoto)"; *C.R. Acad. Sci. (Paris)* 287: 1293-1295 (1978).

Dewhurst, W. G. and Marley, E., "Action of sympathomimetic and allied amines on the central nervous system of the chicken", *Br. J. Pharmacol.* 25: 705-727 (1965).

Dewhurst, W. G., "Cerebral amine functions in health and disease. In *Studies in Psychiatry*, (Sheperd, M. and Davies, D. L. (Eds.)), Oxford University Press, pp. 289-317 (1968a).

Dewhurst, W. G., "New theory of cerebral amine function and its clinical application", *Nature* 218: 1130-1133 (1968b).

Dourish, C. T. and Greenshaw, A. J., "Effects of intraventricular tryptamine and 5-hydroxytryptamine on spontaneous motor activity in the rat", *Res. Commun. Psychol. Psychiat. Behav.* 8: 1-9 (1983).

Dudai, Y., "High-affinity octopamine receptors revealed in Drosophila by binding of [3H]octopamine", *Neurosci. Lett.* 28: 163-167 (1982).

Dudai, Y. and Zvi, S., "High-affinity [³H]octopamine binding sites in *Drosophila melanogaster*: Interaction with ligands and relationship to octopamine receptors", *Comp. Biochem. Physiol.* 77C: 145-151 (1984).

Durkin, M. M et al., "Localization of messenger RNAs encoding three GABA transporters in rat brain: an in situ hybridization study", *Brain Res. Mol. Brain Res.* 33: 7-21 (1995).

Durden, D. A. et al., "Identification and distribution of β-phenylethylamine in the rat", *Can. J. Biochem.* 51: 995-1002 (1973).

Durden, D. A. and Philips, S. R., "Kinetic measurements of the turnover rates of phenylethylamine and tryptamine in vivo in the rat brain", *J. Neurochem.* 34: 1725-1732 (1980).

Dyck, L. E., "Release of some endogenous trace amines from rat striatal slices in the presence and absence of a monoamine oxidase inhibitor", *Life Sci.* 44: 1149-1156 (1989).

Dyck, L. E., "Tryptamine transport in rat brain slices: A comparison with 5-hydroxytryptamine", *Neurochem. Res.* 9: 617-628 (1984).

Fletcher, P. J. and Paterson, I. A., "A comparison of the effects of tryptamine and 5-hydroxytryptamine on feeding following injection into the paraventricular nucleus of the hypothalamus", *Pharmacol. Biochem. Behav.* 32: 907-911 (1989).

Fletcher, P. J., "Conditioned taste aversion induced by tryptamine: A temporal analysis", *Pharmacol. Biochem. Behav.* 25: 995-999 (1986).

Fletcher, P. J., "Tryptamine impairs the acquisition of a one-way active avoidance task", *Pharmacol. Biochem. Behav.* 32: 317-321 (1989).

Foldes, A. and Costa, E., "Relationship of brain monoamines and locomotor activity in rats", *Biochem. Pharmacol.* 24: 1617-1621 (1975).

Fregly, M. J. et al., "Effect of dietary treatment with L-tryptophan on the development of renal hypertension in rats", *Pharmacol.* 36: 91-100 (1988).

Fuxe, K. et al., "Quantitative autoradiographic localization of [3H]-imipramine binding sites in the brain of the rat: relationship to ascending 5-hydroxytryptamine neuron systems", *Proc. Natl. Acad. Sci. U.S.A.* 80: 3836-3840 (1983).

Gerber, R., "Intra-accumbens tryptamine injections increase rat locomotor activity", *Fed. Proc.* 45: 430 (abstract) (1986).

Gerhardt, C. C. et al., "Molecular cloning and pharmacological characterization of a molluscan octopamine receptor", *Mol. Pharmacol.* 51: 293-300 (1997).

Greenshaw, A. J. et al., "Depletion of striatal β-phenylethylamine following dopamine but not 5-HT denervation", *Brain Res. Bull.* 17: 477-484 (1986).

Gundersen, C. B., et al., "Serotonin receptors induced by exogenous messenger RNA in *Xenopus* oocytes" *Proc. R. Soc. Lond. B. Biol. Sci.* 219(1214): 103-109 (1983).

Harrison, R. E. W. and Christian, S. T., "Individual housing stress elevates brain and adrenal tryptamine", In *Neurobiology of Trace Amines: Analytical, Physiological, Behavioral and Clinical Aspects*, Boulton, A. A. et al., (Eds.), Humana Press, Clifton, N.J., pp. 249-256 (1984).

Hashemzadeh, H. et al., "Receptors for [³H]octopamine in the adult firefly light organ", *Life Sci.* 37: 433-440 (1985).

Hauger, R. L. et al., "Specific [³H]β-phenylethylamine binding sites in rat brain", *Eur. J. Pharmacol.* 83: 147-148 (1982).

Hayaishi, O., "Properties and function of the indoleamine 2,3-dioxygenase", *J. Biochem.* 79: 13P (1976).

Herkert, E. E. and Keup, W., "Excretion patterns of tryptamine, indoleacetic acid and 5-hydroxyindoleacetic acid, and their correlation with mental changes in schizophrenic patients under medication with alpha methyldopa", *Psychopharm. (Berl.)* 15: 48-59 (1969).

Hery, F. et al., "Effect of nerve activity on the in vivo release of [3H]-serotonin continuously formed from L-[3H]-tryptophan in the caudate nucleus of the cat", *Brain Res.* 169: 317-334 (1979).

Hicks, P. E. and Langer, S. Z., "Antagonism by tetrahydro-α-carboline of the vasoconstrictor responses to tryptamine in rat tail arteries", *Eur. J. Pharmacol.* 96: 145-149 (1983).

Inanobe, A., et al., "Characterization of G-protein-gated K+ channels composed of Kir3.2 subunits in dopaminergic neurons of the substantia nigra" *J. of Neurosci.* 19(3): 1006-1017 (1999).

Jackson, D. et al., "A functional effect of dopamine in the nucleus accumbens and in some other dopamine rich parts of the brain", *Psychopharmacol.* 45: 139-149 (1975).

Jaeger, C. B. et al., "Immunocytochemical localization of aromatic-1-amino acid decarboxylase. In *Handbook of Chemical Neuroanatomy, vol. 2; Classical Transmitters in the CNS, Part* 1, Elsevier, Amsterdam, pp. 387-408, Bjorklund A. and Hokfelt T. (Eds.) (1984).

Jones, R. S. G. and Boulton, A. A., "Tryptamine and 5-hydroxytryptamine: Actions and interactions on cortical neurons in the rat", *Life Sci.* 27: 1849-1856 (1980).

Jones, R. S. G., "Tryptamine: a neuromodulator or neurotransmitter in mammalian brain?", *Prog. Neurobiol.* 19: 117-139 (1982a).

Jones, R. S. G., "A comparison of the responses of cortical neurons to iontophoretically applied tryptamine and 5-hydroxytryptamine in the rat", *Neuropharmacol.* 21: 209-214 (1982b).

Jones, R. S. G., "Responses of cortical neurons to stimulation of the nucleus raphe medianus: A pharmacological analysis of the role of indoleamines", *Neuropharmacol.* 21: 511-520 (1982c).

Juorio, A. V. and Durden, D. A., "The distribution and turnover of tryptamine in the brain and spinal cord", *Neurochem. Res.* 9: 1283-1293 (1984).

Juorio, A. V., "Brain trace amines: mapping studies and effects of mesencephalic lesions" In *The Trace Amines: Comparative and Clinical Neurobiology* (Edited by A. A. Boulton, A. V. Juorio, R. G. H. Downer), pp. 157-174. Humana Press, Clifton, N.J. (1988).

Juorio, A. V., "Presence and metabolism of β-phenylethylamine, p-tyramine, m-tyramine and tryptamine in the brain of the domestic fowl", *Brain Res.* 111: 442-445 (1976).

Juorio, A. V. and Sloley, B. D., "The presence of tyramine and related monoamines in the nerve cord and some other tissues of the lobster, *Homarus americanus*", *Brain Res.* 444: 380-382 (1988).

Kaulen, P. et al., "Characterization and quantitative autoradiography of [3H]tryptamine binding sites in rat brain", *Brain Res.* 366: 72-88 (1986).

Kellar, K. J. and Cascio, C. S., "[3H]Tryptamine: high affinity binding sites in rat brain", *Eur. J. Pharmacol.* 78: 475-478 (1982).

Kitada, Y. et al., "Involvement of α- and β₁-adrenergic mechanisms in the immobility-reducing action of desipramine in the force swimming test", *Neuropharmacol.* 22: 1055-1060 (1983).

Krapivinsky, G., et al., "The G-protein-gated atrial K channel IKACh is a heteromultimer of two inwardly rectifying K(+)-channel proteins" *Nature* 374: 135-141 (1995).

Krapivinsky, G., et al., "The cardiac inward rectifier K channel subunit, CIR, does not comprise the ATP-sensitive K channel, IKATP", *J. Biol. Chem.* 270: 28777-28779 (1995b).

Krstic, M. K. and Djurkovic, D., "Analysis of cardiovascular responses to central injection of tryptamine in rats", *Neurophammacol.* 24: 517-525 (1985).

Kubo, Y., et al., "Primary structure and functional expression of a rat G-protein-coupled muscarinic potassium channel" *Nature* 364:802-806 (1993).

Larson, A. A. and Wilcox, G. L., "Synergistic behavioral effects of serotonin and tryptamine injected intrathecally in mice", *Neuropharmacol.* 23: 1415-1418 (1984).

Larson, A. A., "Hyperalgesia produced by the intrathecal administration of tryptamine to rats", *Brain Res.* 265: 109-117 (1983).

Lazareno, S. and Birdsall, N. J. M., "Pharmacological characterization of acetylcholine stimulated [$^{35}$S]-GTPγS binding mediated by human muscarinic m1-m4 receptors: antagonist studies", *Br. J. Pharmacol.* 109: 1120-1127 (1993).

Lemberger, L., "The disposition and metabolism of tryptamine and the in vivo formation of 6-hydroxytryptamine in the rabbit", *J. Pharm. Exp. Ther.* 177: 169-176 (1971).

Levine, R. J. et al., "Studies on the metabolism of aromatic amines in relation to altered thyroid function in man", *J. Clin. Endocrinol. Metab.* 22: 1242-1250 (1962).

Leysen, J. E. et al., "(3H)Ketanserin (R 41468), a selective 3H-ligand for serotonin2 receptor binding sites", *Mol. Pharmacol.* 21: 301-314 (1982).

Mallard, N. J. et al., "Characterization and autoradiographical localization of non-adrenoceptor idazoxan binding sites in the rat brain", *Br. J. Pharmacol.* 106: 1019-1027 (1992).

Marien, M. R. et al., "Injections of deuterated tryptamine into the nucleus accumbens of the rat: Effects on locomotor activity and monoamine metabolism", *Neuropharmacol.* 26: 1481-1488 (1987).

Marsden, C. A. and Curzon, G., "Effects of lesions and drugs on brain tryptamine", *J. Neurochem.* 23: 1171-1176 (1974).

Marsden, C. A. and Curzon, G., "The contribution of tryptamine to the behavioral effects of L-tryptophan in tranylcypromine-treated rats", *Psychopharm.* 57: 71-76 (1978).

Martin, W. R. et al., "The demonstration of tyrptamine in regional perfusates of dog brain", *Psychopharm.* 37: 189-198 (1974).

Matsuishi, T. and Yamashita, Y., "Neurochemical and neurotransmitter studies in patients with learning disabilities", *No To Hattatsu,* 31: 245-248 (1999).

Maxwell, G. D et al., "Regional synthesis of neurotransmitter candidates in the CNS of the moth *Manduca sexta*", *Comp. Biochem. Physiol. C.,* 61C:109-119 (1978).

McCormack, J. K. et al., "Autoradiographic localisation of tryptamine binding sites in the rat and dog central nervous system", *J. Neurosci.* 6: 94-101 (1986).

McGeer, P. L., et al., (Eds.) "*Molecular Neurobiology of the Mammalian Brain*", Plenum Press, New York, p. 362 (1979).

Meibach, R. C. et al., "Characterization and radioautography of [$^3$H]LSD binding by rat brain slices in vitro: The effect of 5-hydroxytryptamine", *Eur. J. Pharmacol.* 67: 371-382 (1980).

Meibach, R. C. et al., "A detailed protocol for the in-vitro-radioautography visualization of serotonergic receptors", *J. Histochem. Cytochem.* 30: 831-836 (1982).

Merikangas, K. R. et al., "Tyramine conjugation deficit in migraine, tension-type headache, and depression", *Biol. Psychiatry* 38: 730-736 (1995).

Milligan, G., et al., "Use of chimeric Gα proteins in drug discovery" *TIPS* (In press).

Nakada, M. T. et al., "Localization and characterization by quantitative autoradiography of [$^{125}$I]LSD binding sites in rat brain", *Neurosci. Lett.* 49: 13-18 (1984).

Nguyen, T. V. and Juorio, A. V., "Binding sites for brain trace amines", *Cell. Mol. Neurobiol.* 9: 297-311 (1989).

Ohta Y. et al, "Role of endogenous serotonin and histamine in the pathogenesis of gastric mucosal lesions in unanesthetized rats with a single treatment of compound 48/80, a mast cell degranulator", *Pharmacol. Res.* 39: 261-267 (1999).

Palacios, J. M. et al., "The distribution of serotonin receptors in the human brain: high density of [$^3$H]LSD binding sites in the raphe nuclei of the brainstem", *Brain Res.* 274: 150-155 (1983).

Paul, S. M. et al., "(+)-Amphetamine binding to rat hypothalamus: relation to anorexic potency for phenylethylamines", *Science* 218: 487-490 (1982).

Perry, D. C. et al., "[$^3$H]Tryptamine binding sites are not identical to monoamine oxidase in rat brain", *J. Neurochem.* 51: 1535-1540 (1988).

Perry, D. C., "[$^3$H]Tryptamine autoradiography in rat brain and choroid plexus reveals two distinct sites", *J. Pharmacol. Exp. Ther.* 236: 548-559 (1986).

Perry, T. L., "Urinary excretion of amines in phenylketonuria and Mongolism", *Science* 136: 879-890 (1962).

Philips, S. R. et al., "Identification and distribution of tryptamine in the rat", *Can. J. Biochem.* 52: 447-451 (1974).

Philips, S. R., "Analysis of trace amines:endogenous levels and the effects of various drugs on tissue concentrations in the rat", In *Neurobiology of the Trace Amines: Analytical, Physiological, Pharmacological, Behavioral and Clinical Aspects*, Humana Press, Clifton, N.J., pp. 127-144 (1984).

Philips, S. R. and Boulton, A. A., "The effect of monoamine oxidase inhibitors on some arylalkylamines in rat striatum", *J. Neurochem.* 33: 159-167 (1979).

Philips, S. R., "Evidence for the presence of m-tyramine, p-tyramine, tryptamine and phenylethylamine in the rat brain and several areas of human brain" *Biol. Psychiat.* 13: 51-57 (1978).

Pijnenburg, A. J. J. et al., "Effects of chemical stimulation of the mesolimbic dopamine system upon locomotor activity", *Eur. J. Pharmacol.* 35: 45-58 (1976).

Plaznik A. et al., "A stimulatory effect of intraaccumbens injections of noradrenaline on the behavior of rats in the forced swim test", Psychopharmacol. 87: 119-123 (1985).

Quick, M. W. and Lester, H. A., "Method for expression of excitability of proteins in *Xenopus* oocytes", *Methods in Neurosci.* 19: 261-279 (1994).

Quock, R. M. and Weick, B. G., "Tryptamine-induced drug effects insensitive to serotonergic antagonists: evidence of specific tryptaminergic receptor stimulation?" *J. Pharm. Pharmac.* 30: 280-283 (1978).

Riordan, J. R., "The cystic fibrosis transmembrane conductance regulator", *Ann. Rev. Physiol.* 55: 609-630 (1993).

Roeder, T., "Biogenic amines and their receptors", *Comp. Biochem. Physiol.* 107C: 1-12 (1994).

Rommelspacher, H. et al., "Pharmacology of harmalan (1-methyl-2,4-dihydro-p-carboline)", *Eur. J. Pharmacol.* 109: 363-371 (1985).

Saavedra, J. M. and Axelrod, J., "Brain tryptamine and the effects of drugs", *Adv. Biochem. Psychopharmacol.* 10: 135-139 (1974).

Saavedra, J. M. and Axelrod, J., "Effect of drugs on the tryptamine content of rat tissues", *J. Pharm. Exp. Ther.* 185: 523-529 (1973).

Sabelli, H. C. and Mosnaim, A. D., "Phenylethylamine hypothesis of affective disorder", *Amer. Psychiat.* 131: 695-699 (1974).

Salon, J. A. and Owicki, J. A., "Real-time measurements of receptor activity: Application of microphysiometric techniques to receptor biology" *Meth. Neurosci.* 25: 201-224 (1996).

Sandier, M. et al., "Deficient production of tyramine and octopamine in cases of depression", *Nature* 278: 357-358 (1979).

Saudou, F. N. et al., "Cloning and characterization of *Drosophila* tyramine receptor", *EMBO J.* 9: 3611-3617 (1990).

Segonzac, A. et al., "Saturable uptake of [3H]-tryptamine in rabbit platelets is inhibited by 5-hydroxytryptamine uptake blockers", *Naunyn-Schmiedeberg's Arch. Pharmacol.* 328: 33-37 (1984).

Segonzac, A., "Tryptamine, a substrate for the serotonin transporter in human platelets, modifies the dissociation kinetics of [3H]imipramine binding: Possible allosteric interaction", *J. Neurochem.* 44: 349-356 (1985).

Shih, J. C. et al., "Monoamine oxidase: from genes to behavior", *Ann. Rev. Neurosci.* 22: 197-217 (1999).

Slater, P. and Patel, S., "Autoradiographic distribution of serotonin2 receptors in rat brain", *Eur. J. Pharmacol.* 92: 297-298 (1983).

Slingsby, J. M. and Boulton, A. A., "Separation and quantitation of some urinary arylalkylamines", *J. Chromatog.* 123: 51-56 (1976).

Smith, I. and Kellow, A. H., "Aromatic amines in Parkinson's disease", *Nature* 221: 1261-1264 (1969).

Smith, K. E., et al., "Expression cloning of a rat hypothalamic galanin receptor coupled to phosphoinositide turnover", *J. Biol. Chem.* 272: 24612-24616 (1997).

Snodgrass, S. R. and Horn, A. S., "An assay procedure for tryptamine in brain and spinal cord using its [3H]-dansyl derivative", *J. Neurochem.* 21: 687-696 (1973).

Snodgrass, S. R. and Iversen, L. L., "Formation and release of [3H]-tryptamine from [3H]-tryptophan in rat spinal cord slices", *Adv. Biochem. Psychopharm.* 10: 141-150 (1974).

Sourkes, T. L., "Tryptophan in hepatic coma", *J. Neural Transm.* 14(Suppl): 79-86 (1978).

Stoof, J. C., Liem, A. L. and Mulder, A. H., "Release and receptor stimulating properties of p-tyramine in rat brain", *Arch. Int. Pharmacodyn. Ther.* 220: 62-71 (1976).

Sullivan, M. X., "Indolethylamine in the urine of pellagrins", *J. Biol. Chem.* 50: xxxix (1922).

Takahashi, T., et al., "Rat brain serotonin receptors in *Xenopus* oocytes are coupled by intracellular calcium to endogenous channels" *Proc. Natl. Acad. Sci. USA* 84(14): 5063-5067 (1987).

Tian, W., et al., "Determinants of alpha-Adrenergic Receptor Activation of G protein: Evidence for a Precoupled Receptor/G protein State" *Molecular Pharm.* 45: 524-553 (1994).

Ungar, F. et al., "Tyramine-binding by synaptosomes from rat brain: Effect of centrally active drugs", *Biol. Psychiat.* 12: 661-668 (1977).

Usdin, E. and Sandler, M. (Eds.), "*Trace Amines and the Brain*", Marcel Dekker, New York, N.Y. (1976).

Vaccari, A., "High affinity binding of [$^3$H]-tyramine in the central nervous system", *Br. J. Pharmacol.* 89: 15-25 (1986).

Vaccari, A., "High affinity binding of p-tyramine: A process in search of a function. In *Trace Amines: Comparative and Clinical Neurobiology* (Boulton, A. A. et al., Eds.), Humana Press, Clifton, N.J., pp. 119-132 (1988).

Varma, D. R. and Chemtob, S., "Endothelium- and Beta-2 Adrenoceptor-independent relaxation of rat aorta by tyramine and certain other phenylethylamines", *J. Pharmacol. Exp. Ther.* 265: 1096-1104 (1993).

Vaughan, T. R., "The role of food in the pathogenesis of migraine headache", *Clin Rev. Allergy* 12: 167-180 (1994).

Weinstock, M. et al., "Changes in brain catecholamine turnover and receptor sensitivity induced by social deprivation in rats", *Psychopharmacol.* 56: 205-209 (1978).

Winter, J. C. and Gessner, P. K., "Phenoxybenzamine-antagonism of tryptamines, their indene isosteres and 5-hydroxytryptamine in the rat stomach fundus preparation", *J. Pharm. Exp. Ther.* 162: 286-293 (1968).

Witz, P. et al., "Cloning and characterization of a *Drosophila* serotonin receptor that activates adenylate cyclase", *Proc. Natl. Acad. Sci. U.S.A.* 87: 8940-8944 (1990).

Wood, P. L. et al., "[3H]Tryptamine receptors in rat brain", In *Neuropsychopharmacology of the Trace Amines*, (Boulton, A. A. et al., Eds.), Humana Press, Clifton, N.J., pp. 101-114 (1985).

Wolf, M. E. and Mosnaim, A. D., "Phenylethylamine in neuropsychiatric disorders", *Gen. Pharmacol.* 14: 385-390 (1983).

Wu, P. H. and Boulton, A. A., "Distribution and metabolism of tryptamine in rat brain", *Can. J. Biochem.* 51: 1104-1112 (1973).

Young, S. N. et al., "The origin of indoleacetic acid and indolepropionic acid in rat and human cerebrospinal fluid", *J. Neurochem.* 34: 1087-1092 (1980).

---

What is claimed is:

1. A method for preparing a composition which comprises:
   (a) determining whether a chemical compound is a human SNORF33 receptor agonist which comprises contacting cells transfected with and expressing DNA encoding the human SNORF33 receptor, wherein the cells prior to being transfected with the DNA do not express the human SNORF33 receptor, with the compound under conditions permitting the activation of the human SNORF33 receptor, and detecting any increase in human SNORF33 receptor activation, so as to thereby determine whether the compound is a human SNORF33 receptor agonist;
   (b) recovering the compound free of any human SNORF33 receptor; and
   (c) admixing the compound with a pharmaceutically acceptable carrier;
   wherein the human SNORF33 receptor has the amino acid sequence identical to that shown in SEQ ID NO: 6 or that encoded by plasmid pcDNA3.1-hSNORF33-f (ATCC Patent Deposit Designation PTA-398) or plasmid pEXJ-hSNORF33-f (ATCC Patent Deposit Designation PTA-570).

2. A method for preparing a composition which comprises:
   (a) determining whether a chemical compound is a human SNORF33 receptor antagonist which comprises contacting cells transfected with and expressing DNA encoding the human SNORF33 receptor, wherein the cells prior to being transfected with the DNA do not express the human SNORF33 receptor, with the compound in the presence of a known human SNORF33 receptor agonist, under conditions permitting the activation of the human SNORF33 receptor, and detecting any decrease in human SNORF33 receptor activation, so as to thereby determine whether the compound is a human SNORF33 receptor antagonist;
   (b) recovering the compound free of any human SNORF33 receptor; and (c) admixing the compound with a pharmaceutically acceptable carrier;

wherein the human SNORF33 receptor has the amino acid sequence identical to that shown in SEQ ID NO: 6 or that encoded by plasmid pcDNA3.1-hSNORF33-f (ATCC Patent Deposit Designation PTA-398) or plasmid pEXJ-hSNORF33-f (ATCC Patent Deposit Designation PTA-570).

3. A method for preparing a composition which comprises:
(a) identifying a chemical compound which specifically binds to a human SNORF33 receptor, which comprises contacting cells, or a membrane preparation from the cells, transfected with DNA encoding, and expressing on their cell surface, the human SNORF33 receptor, wherein the cells prior to being transfected with the DNA do not express the human SNORF33 receptor, with the compound under conditions suitable for binding, and detecting specific binding of the chemical compound to the human SNORF33 receptor;
(b) recovering the compound free of any human SNORF33 receptor; and
(c) admixing the compound with a pharmaceutically acceptable carrier;
wherein the human SNORF33 receptor has the amino acid sequence identical to that shown in SEQ ID NO: 6 or that encoded by plasmid pcDNA3.1-hSNORF33-f (ATCC Patent Deposit Designation PTA-398) or plasmid pEXJ-hSNORF33-f (ATCC Patent Deposit Designation PTA-570).

4. A method for preparing a composition which comprises:
(a) identifying a chemical compound which competitively binds to a human SNORF33 receptor which comprises separately contacting cells, or a membrane preparation of the cells, transfected with DNA encoding the human SNORF33 receptor and expressing on their cell surface the human SNORF33 receptor, wherein the cells prior to being transfected with the DNA do not express the human SNORF33 receptor, with both the chemical compound and a second chemical compound known to bind to the receptor, and with only the second chemical compound, under conditions suitable for binding of the compounds and the second chemical compound to the receptor, and detecting specific binding of the chemical compound to the human SNORF33 receptor, a decrease in the binding of the second chemical compound to the human SNORF33 receptor in the presence of the chemical compound being tested indicating that the chemical compound binds to the human SNORF33 receptor;
(b) recovering the compound free of any human SNORF33 receptor; and
(c) admixing the compound with a pharmaceutically acceptable carrier;
wherein the human SNORF33 receptor has the amino acid sequence identical to that shown in SEQ ID NO: 6 or that encoded by plasmid pcDNA3.1-hSNORF33-f (ATCC Patent Deposit Designation PTA398) or plasmid pEXJ-hSNORF33-f (ATCC Patent Deposit Designation PTA-570).

5. A method for preparing a composition which comprises:
(a) determining whether a chemical compound specifically binds to and activates a human SNORF33 receptor, which comprises contacting cells, which cells are producing a second messenger response and are transfected with DNA encoding the human SNORF33 receptor and expressing on their cell surface the human SNORF33 receptor, wherein the cells prior to being transfected with the DNA do not express the human SNORF33 receptor, with the chemical compound under conditions suitable for activation of the human SNORF33 receptor, and measuring the second messenger response in the presence and in the absence of the chemical compound, a change in the second messenger response in the presence of the chemical compound indicating that the compound activates the human SNORF33 receptor;
(b) recovering the compound free of any human SNORF33 receptor; and
(c) admixing the compound with a pharmaceutically acceptable carrier;
wherein the human SNORF33 receptor has the amino acid sequence identical to that shown in SEQ ID NO: 6 or that encoded by plasmid pcDNA3.1-hSNORF33-f (ATCC Patent Deposit Designation PTA-398) or plasmid pEXJ-hSNORF33-f (ATCC Patent Deposit Designation PTA-570).

6. A method for preparing a composition which comprises:
(a) determining whether a chemical compound specifically binds to and inhibits activation of a human SNORF33 receptor, which comprises separately contacting cells, which cells are producing a second messenger response and are transfected with DNA encoding the human SNORF33 receptor and expressing on their cell surface the human SNORE33 receptor, wherein the cells prior to being transfected with the DNA do not express the human SNORF33 receptor, with both the chemical compound and a second chemical compound known to activate the human SNORF33 receptor, and with only the second chemical compound, under conditions suitable for activation of the human SNORF33 receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the human SNORF33 receptor;
(b) recovering the compound free of any human SNORF33 receptor; and
(c) admixing the compound with a pharmaceutically acceptable carrier;
wherein the human SNORF33 receptor has the amino acid sequence identical to that shown in SEQ ID NO: 6 or that encoded by plasmid pcDNA3.1-hSNORF33-f (ATCC Patent Deposit Designation PTA-398) or plasmid pEXJ-hSNORF33-f (ATCC Patent Deposit Designation PTA-570).

7. A method for preparing a composition which comprises:
(a) contacting cells transfected with and expressing DNA encoding a human SNORF33 receptor, wherein the cells prior to being transfected with the DNA do not express the human SNORF33 receptor, with compounds not known to activate the human SNORF33 receptor, under conditions permitting activation of the human SNORF33 receptor;
(b) determining whether activation of the human SNORF33 receptor is increased in the presence of one or more of the compounds; and if so
(c) separately determining whether activation of the human SNORF33 receptor is increased by a compound of the one or more compounds, so as to thereby identify the compound which activates the human SNORF33 receptor;
(d) recovering the compound free of any human SNORF33 receptor; and
(e) admixing the compound with a pharmaceutically acceptable carrier;
wherein the human SNORF33 receptor has the amino acid sequence identical to that shown in SEQ ID NO: 6 or that encoded by plasmid pcDNA3.1-hSNORF33-f (ATCC Patent Deposit Designation PTA-398) or plasmid pEXJ-hSNORF33-f (ATCC Patent Deposit Designation PTA-570).

8. A method for preparing a composition which comprises:
(a) contacting cells transfected with and expressing DNA encoding a human SNORF33 receptor, wherein the cells prior to being transfected with the DNA do not express the human SNORF33 receptor, with compounds in the presence of a known human SNORF33 receptor agonist, under conditions permitting activation of the human SNORF33 receptor;
(b) determining whether the extent or amount of activation of the human SNORF33 receptor is reduced in the presence of one or more of the compounds, relative to the extent or amount of activation of the human SNORF33 receptor in the absence of the one or more compounds; and if so
(c) separately determining whether a compound of the one or more compounds inhibits activation of the human SNORF33 receptor, so as to thereby identify the compound that inhibits activation of the human SNORF33 receptor;
(d) recovering the compound free of any human SNORF33 receptor; and
(e) admixing the compound with a pharmaceutically acceptable carrier;
wherein the human SNORF33 receptor has the amino acid sequence identical to that shown in SEQ ID NO: 6 or that encoded by plasmid pcDNA3.1-hSNORF33-f (ATCC Patent Deposit Designation PTA-398) or plasmid pEXJ-hSNORF33-f (ATCC Patent Deposit Designation PTA-570).

* * * * *

SEQUENCE LISTING

<160> NUMBER OF SEQ ID NOS: 46

<210> SEQ ID NO 1
<211> LENGTH: 573
<212> TYPE: DNA
<213> ORGANISM: Homo sapiens

<400> SEQUENCE: 1

```
actgtggact ttcttctggg gtgtctggtc atgccttaca gtatggtgag atctgctgag      60
cactgttggt attttggaga agtcttctgt aaaattcaca caagcaccga cattatgctg     120
agctcagcct ccattttcca tttgtctttc atctccattg accgctacta tgctgtgtgt     180
gatccactga gatataaagc caagatgaat atcttggtta tttgtgtgat gatcttcatt     240
```

```
agttggagtg tccctgctgt ttttgcattt ggaatgatct ttctggagct aaacttcaaa    300
ggcgctgaag agatatatta caaacatgtt cactgcagag gaggttgctc tgtcttcttt    360
agcaaaatat ctggggtact gacctttatg acttctttt atacctgg atctattatg      420 ttatgtgtct attacagaat atatcttatc gctaaagaac aggcaagatt aattagtgat    480
gccaatcaga agctccaaat tggattggaa atgaaaaatg gaatttcaca aagcaaagaa    540
aggaaagctg tgaagacatt ggggattgtg atg                                 573
```

<210> SEQ ID NO 2
<211> LENGTH: 191
<212> TYPE: PRT
<213> ORGANISM: Homo sapiens

<400> SEQUENCE: 2

```
Thr Val Asp Phe Leu Leu Gly Cys Leu Val Met Pro Tyr Ser Met Val
 1               5                  10                  15

Arg Ser Ala Glu His Cys Trp Tyr Phe Gly Glu Val Phe Cys Lys Ile
            20                  25                  30

His Thr Ser Thr Asp Ile Met Leu Ser Ser Ala Ser Ile Phe His Leu
        35                  40                  45

Ser Phe Ile Ser Ile Asp Arg Tyr Tyr Ala Val Cys Asp Pro Leu Arg
    50                  55                  60

Tyr Lys Ala Lys Met Asn Ile Leu Val Ile Cys Val Met Ile Phe Ile
65                  70                  75                  80

Ser Trp Ser Val Pro Ala Val Phe Ala Phe Gly Met Ile Phe Leu Glu
                85                  90                  95

Leu Asn Phe Lys Gly Ala Glu Glu Ile Tyr Tyr Lys His Val His Cys
            100                 105                 110

Arg Gly Gly Cys Ser Val Phe Phe Ser Lys Ile Ser Gly Val Leu Thr
        115                 120                 125

Phe Met Thr Ser Phe Tyr Ile Pro Gly Ser Ile Met Leu Cys Val Tyr
    130                 135                 140

Tyr Arg Ile Tyr Leu Ile Ala Lys Glu Gln Ala Arg Leu Ile Ser Asp
145                 150                 155                 160

Ala Asn Gln Lys Leu Gln Ile Gly Leu Glu Met Lys Asn Gly Ile Ser
                165                 170                 175

Gln Ser Lys Glu Arg Lys Ala Val Lys Thr Leu Gly Ile Val Met
            180                 185                 190
```

<210> SEQ ID NO 3
<211> LENGTH: 1101
<212> TYPE: DNA
<213> ORGANISM: Rattus norvegicus

<400> SEQUENCE: 3

```
attgctcgac agccaaaggg acagagcagc ctgtgtttag ttctctgtag tgatgcatct     60
ttgccacaat agcgcgaata tttcccacac gaacagcaac tggtcaaggg atgtccgtgc    120
ttcgctgtac agcttaatat cactcataat tctaaccact ctggttggca acttaatagt    180
aatcatttcg atatcccact tcaagcaact tcacacgccc acaaattggc tccttcattc    240
catggccgtt gtcgactttc tgctgggctg tctggtcatg ccctacagca tggtgagaac    300
agttgagcac tgctggtact ttggggaact cttctgcaaa cttcacacca gcactgatat    360
catgctgagc tcggcatcca ttctccacct agccttcatt ccattgacc gctactatgc     420 tgtgtgcgac ccttttaagat acaaagccaa gatcaatctc gccgccattt ttgtgatgat    480
```

```
cctcattagc tggagccttc ctgctgtttt tgcatttggg atgatcttcc tggagctgaa    540
cttagaagga gttgaggagc tgtatcacaa tcaggtcttc tgcctgcgcg gctgttttcc    600
cttcttcagt aaagtatctg gggtactggc attcatgacg tctttctata tacctggatc    660
tgttatgtta tttgtttact atagaatata tttcatagct aaaggacaag caaggtcaat    720
taatcgtgca aatcttcaag ttggattgga agggggaaagc agagcgccac aaagcaagga    780
aacaaaagcc gcgaaaacct tagggatcat ggtgggcgtt ttcctcctgt gctggtgccc    840
gttctttttc tgcatggtcc tggacccttt cctgggctat gttatcccac ccactctgaa    900
tgacacactg aattggtttg gtacctgaa ctctgccttc aacccgatgg tttatgcctt    960
tttctatccc tggttcagaa gagcgttgaa gatggttctc ttcggtaaaa ttttccaaaa    1020
agattcatct aggtctaagt tattttgta acgcaatcca tgaaaccagt atattttgta    1080
gttcttaaga gcagttggtg a                                              1101
```

<210> SEQ ID NO 4
<211> LENGTH: 332
<212> TYPE: PRT
<213> ORGANISM: Rattus norvegicus

<400> SEQUENCE: 4

```
Met His Leu Cys His Asn Ser Ala Asn Ile Ser His Thr Asn Ser Asn
 1               5                  10                  15

Trp Ser Arg Asp Val Arg Ala Ser Leu Tyr Ser Leu Ile Ser Leu Ile
             20                  25                  30

Ile Leu Thr Thr Leu Val Gly Asn Leu Ile Val Ile Ile Ser Ile Ser
         35                  40                  45

His Phe Lys Gln Leu His Thr Pro Thr Asn Trp Leu His Ser Met
     50                  55                  60

Ala Val Val Asp Phe Leu Leu Gly Cys Leu Val Met Pro Tyr Ser Met
 65                  70                  75                  80

Val Arg Thr Val Glu His Cys Trp Tyr Phe Gly Glu Leu Phe Cys Lys
                 85                  90                  95

Leu His Thr Ser Thr Asp Ile Met Leu Ser Ser Ala Ser Ile Leu His
            100                 105                 110

Leu Ala Phe Ile Ser Ile Asp Arg Tyr Tyr Ala Val Cys Asp Pro Leu
        115                 120                 125

Arg Tyr Lys Ala Lys Ile Asn Leu Ala Ala Ile Phe Val Met Ile Leu
    130                 135                 140

Ile Ser Trp Ser Leu Pro Ala Val Phe Ala Phe Gly Met Ile Phe Leu
145                 150                 155                 160

Glu Leu Asn Leu Glu Gly Val Glu Glu Leu Tyr His Asn Gln Val Phe
                165                 170                 175

Cys Leu Arg Gly Cys Phe Pro Phe Phe Ser Lys Val Ser Gly Val Leu
            180                 185                 190

Ala Phe Met Thr Ser Phe Tyr Ile Pro Gly Ser Val Met Leu Phe Val
        195                 200                 205

Tyr Tyr Arg Ile Tyr Phe Ile Ala Lys Gly Gln Ala Arg Ser Ile Asn
    210                 215                 220

Arg Ala Asn Leu Gln Val Gly Leu Glu Gly Ser Arg Ala Pro Gln
225                 230                 235                 240

Ser Lys Glu Thr Lys Ala Ala Lys Thr Leu Gly Ile Met Val Gly Val
                245                 250                 255
```

```
Phe Leu Leu Cys Trp Cys Pro Phe Phe Cys Met Val Leu Asp Pro
            260                 265                 270

Phe Leu Gly Tyr Val Ile Pro Pro Thr Leu Asn Asp Thr Leu Asn Trp
        275                 280                 285

Phe Gly Tyr Leu Asn Ser Ala Phe Asn Pro Met Val Tyr Ala Phe Phe
        290                 295                 300

Tyr Pro Trp Phe Arg Arg Ala Leu Lys Met Val Leu Phe Gly Lys Ile
305                 310                 315                 320

Phe Gln Lys Asp Ser Ser Arg Ser Lys Leu Phe Leu
                325                 330

<210> SEQ ID NO 5
<211> LENGTH: 1038
<212> TYPE: DNA
<213> ORGANISM: Homo sapiens

<400> SEQUENCE: 5
tcaggaatga tgcccttttg ccacaatata attaatattt cctgtgtgaa aaacaactgg      60
tcaaatgatg tccgtgcttc cctgtacagt ttaatggtgc tcataattct gaccacactc     120
gttggcaatc tgatagttat tgtttctata tcacacttca aacaacttca taccccaaca     180
aattggctca ttcattccat ggccactgtg gactttcttc tggggtgtct ggtcatgcct     240
tacagtatgg tgagatctgc tgagcactgt tggtattttg gagaagtctt ctgtaaaatt     300
cacacaagca ccgacattat gctgagctca gcctccattt tccatttgtc tttcatctcc     360
attgaccgct actatgctgt gtgtgatcca ctgagatata agccaagat gaatatcttg     420
gttatttgtg tgatgatctt cattagttgg agtgtccctg ctgttttgc atttggaatg     480
atctttctgg agctaaactt caaggcgct gaagagatat attacaaaca tgttcactgc     540
agaggaggtt gctctgtctt ctttagcaaa atatctgggg tactgacctt tatgacttct     600
ttttatatac ctggatctat tatgttatgt gtctattaca gaatatatct tatcgctaaa     660
gaacaggcaa gattaattag tgatgccaat cagaagctcc aaattggatt ggaaatgaaa     720
aatgaatttt cacaaagcaa agaaaggaaa gctgtgaaga cattggggat tgtgatggga     780
gttttcctaa tatgctggtg ccctttcttt atctgtacag tcatggaccc ttttcttcac     840
tacattattc cacctacttt gaatgatgtg ttgatttggt ttggctactt gaactctaca     900
tttaatccaa tggtttatgc atttttctat ccttggttta gaaaagcact gaagatgatg     960
ctgtttggta aaattttcca aaaagattca tccaggtgta aattatttt ggaattgagt    1020
tcatagaatt attatatt                                                  1038

<210> SEQ ID NO 6
<211> LENGTH: 339
<212> TYPE: PRT
<213> ORGANISM: Homo sapiens

<400> SEQUENCE: 6

Met Met Pro Phe Cys His Asn Ile Ile Asn Ile Ser Cys Val Lys Asn
  1                 5                  10                  15

Asn Trp Ser Asn Asp Val Arg Ala Ser Leu Tyr Ser Leu Met Val Leu
                 20                  25                  30

Ile Ile Leu Thr Thr Leu Val Gly Asn Leu Ile Val Ile Val Ser Ile
             35                  40                  45

Ser His Phe Lys Gln Leu His Thr Pro Thr Asn Trp Leu Ile His Ser
         50                  55                  60
```

```
Met Ala Thr Val Asp Phe Leu Leu Gly Cys Leu Val Met Pro Tyr Ser
 65                  70                  75                  80

Met Val Arg Ser Ala Glu His Cys Trp Tyr Phe Gly Glu Val Phe Cys
             85                  90                  95

Lys Ile His Thr Ser Thr Asp Ile Met Leu Ser Ser Ala Ser Ile Phe
            100                 105                 110

His Leu Ser Phe Ile Ser Ile Asp Arg Tyr Tyr Ala Val Cys Asp Pro
            115                 120                 125

Leu Arg Tyr Lys Ala Lys Met Asn Ile Leu Val Ile Cys Val Met Ile
        130                 135                 140

Phe Ile Ser Trp Ser Val Pro Ala Val Phe Ala Phe Gly Met Ile Phe
145                 150                 155                 160

Leu Glu Leu Asn Phe Lys Gly Ala Glu Glu Ile Tyr Tyr Lys His Val
                165                 170                 175

His Cys Arg Gly Gly Cys Ser Val Phe Phe Ser Lys Ile Ser Gly Val
            180                 185                 190

Leu Thr Phe Met Thr Ser Phe Tyr Ile Pro Gly Ser Ile Met Leu Cys
            195                 200                 205

Val Tyr Tyr Arg Ile Tyr Leu Ile Ala Lys Glu Gln Ala Arg Leu Ile
        210                 215                 220

Ser Asp Ala Asn Gln Lys Leu Gln Ile Gly Leu Glu Met Lys Asn Gly
225                 230                 235                 240

Ile Ser Gln Ser Lys Glu Arg Lys Ala Val Lys Thr Leu Gly Ile Val
                245                 250                 255

Met Gly Val Phe Leu Ile Cys Trp Cys Pro Phe Phe Ile Cys Thr Val
            260                 265                 270

Met Asp Pro Phe Leu His Tyr Ile Ile Pro Pro Thr Leu Asn Asp Val
            275                 280                 285

Leu Ile Trp Phe Gly Tyr Leu Asn Ser Thr Phe Asn Pro Met Val Tyr
        290                 295                 300

Ala Phe Phe Tyr Pro Trp Phe Arg Lys Ala Leu Lys Met Met Leu Phe
305                 310                 315                 320

Gly Lys Ile Phe Gln Lys Asp Ser Ser Arg Cys Lys Leu Phe Leu Glu
                325                 330                 335

Leu Ser Ser

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:
      primer/probe

<400> SEQUENCE: 7
ttatgcttcc ggctcgtatg ttgtg                                        25

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:
      primer/probe

<400> SEQUENCE: 8
atgtgctgca aggcgattaa gttggg                                       26
```

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:
      primer/probe
<220> FEATURE:
<223> OTHER INFORMATION: n = A, C, T or G (or other modified base such
      as inosine)

<400> SEQUENCE: 9
tnnkntgytg gytnccntty tty                                          23

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:
      primer/probe
<220> FEATURE:
<223> OTHER INFORMATION: n = A, C, T, or G (or other modified base such
      as inosine)

<400> SEQUENCE: 10
arnswrttnv nrtanccnar cc                                           22

<210> SEQ ID NO 11
<211> LENGTH: 63
<212> TYPE: DNA
<213> ORGANISM: Artificial Sequence
<220> FEATURE:
<223> OTHER INFORMATION: Description of Artificial Sequence:
      primer/probe

<400> SEQUENCE: 11
ttctgcatgg tcctggaccc tttcctgggc tatgttatcc cacccactct gaatgacaca   60
ctg                                                                63

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 12
cataattcta accactctgg ttgg                                         24

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:
      primer/probe

<400> SEQUENCE: 13
ctgaaccagg gatagaaaaa ggc                                          23

<210> SEQ ID NO 14
<211> LENGTH: 36
<212> TYPE: DNA
<213> ORGANISM: Artificial Sequence
<220> FEATURE:

```
<223> OTHER INFORMATION: Description of Artificial Sequence:
      primer/probe

<400> SEQUENCE: 14
tccgtaggat ccaattggct cattcattcc atggcc                              36

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence:
      primer/probe

<400> SEQUENCE: 15
agctacaagc ttgcaccagc atattaggaa aactcc                              36

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 16
cagcataatg tcggtgcttg tgtg                                           24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 17
tactgtaagg catgaccaga cacc                                           24

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence:
      primer/probe

<400> SEQUENCE: 18
attagtgatg ccaatcagaa gctcc                                          25

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence:
      primer/probe

<400> SEQUENCE: 19
gaaaggaaag ctgtgaagac attgg                                          25

<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence:
```

```
                                primer/probe

<400> SEQUENCE: 20
gatctaggat ccggaaaagt aaactgattg acagccc                              37

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence:
      primer/probe

<400> SEQUENCE: 21
ctagctaagc ttgatcatca accgatttgc aaaacag                              37

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence:
      primer/probe

<400> SEQUENCE: 22
catggccact gtggactttc t                                               21

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 23
gtcggtgctt gtgtgaattt taca                                            24

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence:
      primer/probe

<400> SEQUENCE: 24
atggtgagat ctgctgagca ctgttggtat t                                    31

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence:
      primer/probe

<400> SEQUENCE: 25
tgcatggtcc tggaccct                                                   18

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:
      primer/probe
```

<400> SEQUENCE: 26
tcgggttgaa ggcagagttc                                                    20

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence:
      primer/probe

<400> SEQUENCE: 27
tgggctatgt tatcccaccc actctgaat                                          29

<210> SEQ ID NO 28
<211> LENGTH: 45
<212> TYPE: DNA
<213> ORGANISM: Artificial Sequence
<220> FEATURE:
<223> OTHER INFORMATION: Description of Artificial Sequence:
      primer/probe

<400> SEQUENCE: 28
cacacgaaca gcaactggtc aagggatgtc cgtgcttcgc tgtac                        45

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence:
      primer/probe

<400> SEQUENCE: 29
gtacagcgaa gcacggacat cccttgacca gttgctgttc gtgtg                        45

<210> SEQ ID NO 30
<211> LENGTH: 252
<212> TYPE: DNA
<213> ORGANISM: mouse

<400> SEQUENCE: 30
ggtactggcg ttcatgactt ccttctatat acctggatct gttatgttat ttgtttacta        60
taggatatat ttcatagcta aaggacaagc aaggtcaatc aatcgtacga atgttcaagt       120
tggattggaa gggaaaagcc aagcaccaca aagcaaggaa acaaaagccg cgaagacctt       180
agggatcatg gtgggcgttt cctcgtatg ctggtgcccg ttctttctct gcacggtcct        240
ggaccctttc ct                                                           252

<210> SEQ ID NO 31
<211> LENGTH: 83
<212> TYPE: PRT
<213> ORGANISM: mouse

<400> SEQUENCE: 31

Val Leu Ala Phe Met Thr Ser Phe Tyr Ile Pro Gly Ser Val Met Leu
  1               5                  10                  15

Phe Val Tyr Tyr Arg Ile Tyr Phe Ile Ala Lys Gly Gln Ala Arg Ser
                 20                  25                  30

Ile Asn Arg Thr Asn Val Gln Val Gly Leu Glu Gly Lys Ser Gln Ala
             35                  40                  45

```
Pro Gln Ser Lys Glu Thr Lys Ala Ala Lys Thr Leu Gly Ile Met Val
        50                  55                  60

Gly Val Phe Leu Val Cys Trp Cys Pro Phe Phe Leu Cys Thr Val Leu
 65                  70                  75                  80

Asp Pro Phe

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence:
      primer/probe

<400> SEQUENCE: 32
actctggttg gcaacttaat agt                                          23

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence:
      primer/probe

<400> SEQUENCE: 33
gcataaacca tcgggttgaa ggc                                          23

<210> SEQ ID NO 34
<211> LENGTH: 37
<212> TYPE: DNA
<213> ORGANISM: Artificial Sequence
<220> FEATURE:
<223> OTHER INFORMATION: Description of Artificial Sequence:
      primer/probe

<400> SEQUENCE: 34
tatcgcggat ccggtactgg cgttcatgac ttccttc                           37

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence:
      primer/probe

<400> SEQUENCE: 35
ccagctaagc ttaggaaagg gtccaggacc gtgcag                            36

<210> SEQ ID NO 36
<211> LENGTH: 1031
<212> TYPE: DNA
<213> ORGANISM: mouse

<400> SEQUENCE: 36
tgcagtgatg catctttgcc acgctatcac aaacatttcc cacagaaaca gcgactggtc    60
aagagaagtc caagcttccc tgtacagctt aatgtcactc ataatcctgg ccactctggt   120
tggcaactta atagtaataa tttccatatc ccatttcaag caacttcata cacccaccaa   180
ctggctcctt cactccatgg ccattgtcga ctttctgctg ggctgtctga taatgccctg   240
cagcatggtg agaactgttg agcgctgttg gtattttggg gaaatcctct gtaaagttca   300
caccagcacc gatatcatgc tgagctccgc ctccattttc cacttagctt tcattttccat   360
```

-continued

```
tgaccgctac tgtgctgtgt gtgacccttt gagatacaaa gccaagatca atatctccac    420
tattcttgtg atgatcctcg ttagttggag ccttcctgct gtttatgcat ttgggatgat    480
cttcctggaa ctgaacttaa aaggagtgga agagctgtat cgcagtcagg tcagcgacct    540
gggcggctgt tctcccttct ttagtaaagt atctggggta ctggcgttca tgacttcctt    600
ctatatacct ggatctgtta tgttatttgt ttactatagg atatatttca tagctaaagg    660
acaagcaagg tcaatcaatc gtacgaatgt tcaagttgga ttggaaggga aaagccaagc    720
accacaaagc aaggaaacaa agccgcgaa gaccttaggg atcatggtgg cgttttcct     780 cgtatgctgg tgcccgttct ttctctgcac ggtcctggac cctttcctgg ctatgttat     840 cccaccctct ctgaatgacg cactgtattg gtttgggtac ttgaattctg ccctcaatcc    900
gatggtttat gcctttttct atccctggtt cagaagagcc ttgaagatgg ttctccttgg    960
taaaattttc caaaagatt catctaggtc taagctattt ttgtaacgca attcatgaaa    1020
cccatgtatt t                                                        1031
```

<210> SEQ ID NO 37
<211> LENGTH: 332
<212> TYPE: PRT
<213> ORGANISM: mouse

<400> SEQUENCE: 37

```
Met His Leu Cys His Ala Ile Thr Asn Ile Ser His Arg Asn Ser Asp
 1               5                   10                  15

Trp Ser Arg Glu Val Gln Ala Ser Leu Tyr Ser Leu Met Ser Leu Ile
            20                  25                  30

Ile Leu Ala Thr Leu Val Gly Asn Leu Ile Val Ile Ile Ser Ile Ser
        35                  40                  45

His Phe Lys Gln Leu His Thr Pro Thr Asn Trp Leu Leu His Ser Met
    50                  55                  60

Ala Ile Val Asp Phe Leu Leu Gly Cys Leu Ile Met Pro Cys Ser Met
65                  70                  75                  80

Val Arg Thr Val Glu Arg Cys Trp Tyr Phe Gly Glu Ile Leu Cys Lys
                85                  90                  95

Val His Thr Ser Thr Asp Ile Met Leu Ser Ser Ala Ser Ile Phe His
            100                 105                 110

Leu Ala Phe Ile Ser Ile Asp Arg Tyr Cys Ala Val Cys Asp Pro Leu
        115                 120                 125

Arg Tyr Lys Ala Lys Ile Asn Ile Ser Thr Ile Leu Val Met Ile Leu
    130                 135                 140

Val Ser Trp Ser Leu Pro Ala Val Tyr Ala Phe Gly Met Ile Phe Leu
145                 150                 155                 160

Glu Leu Asn Leu Lys Gly Val Glu Glu Leu Tyr Arg Ser Gln Val Ser
                165                 170                 175

Asp Leu Gly Gly Cys Ser Pro Phe Phe Ser Lys Val Ser Gly Val Leu
            180                 185                 190

Ala Phe Met Thr Ser Phe Tyr Ile Pro Gly Ser Val Met Leu Phe Val
        195                 200                 205

Tyr Tyr Arg Ile Tyr Phe Ile Ala Lys Gly Gln Ala Arg Ser Ile Asn
    210                 215                 220

Arg Thr Asn Val Gln Val Gly Leu Glu Gly Lys Ser Gln Ala Pro Gln
225                 230                 235                 240

Ser Lys Glu Thr Lys Ala Ala Lys Thr Leu Gly Ile Met Val Gly Val
```

```
                  245                 250                 255
Phe Leu Val Cys Trp Cys Pro Phe Phe Leu Cys Thr Val Leu Asp Pro
        260                 265                 270

Phe Leu Gly Tyr Val Ile Pro Pro Ser Leu Asn Asp Ala Leu Tyr Trp
        275                 280                 285

Phe Gly Tyr Leu Asn Ser Ala Leu Asn Pro Met Val Tyr Ala Phe Phe
        290                 295                 300

Tyr Pro Trp Phe Arg Arg Ala Leu Lys Met Val Leu Leu Gly Lys Ile
305                 310                 315                 320

Phe Gln Lys Asp Ser Ser Arg Ser Lys Leu Phe Leu
            325                 330

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 38
gctgcagggc attatcagac agcc                                           24

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 39
tctgcacggt cctggaccct ttcc                                           24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 40
tatcccaccc tctctgaatg acgc                                           24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 41
ctggagaagc attgctcgac agcc                                           24

<210> SEQ ID NO 42
<211> LENGTH: 34
<212> TYPE: DNA
<213> ORGANISM: Artificial Sequence
<220> FEATURE:
<223> OTHER INFORMATION: Description of Artificial Sequence:
      primer/probe

<400> SEQUENCE: 42
```

```
gtcatcggat ccgcccagcc tgtgtctagt tctc                                    34

<210> SEQ ID NO 43
<211> LENGTH: 36
<212> TYPE: DNA
<213> ORGANISM: Artificial Sequence
<220> FEATURE:
<223> OTHER INFORMATION: Description of Artificial Sequence:
      primer/probe

<400> SEQUENCE: 43
tcagcttcta gagggttgct gggaattgaa ctcagg                                  36

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence:
      primer/probe

<400> SEQUENCE: 44
aaagccgcga agaccttagg                                                    20

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence:
      primer/probe

<400> SEQUENCE: 45
ggtccaggac cgtgcaga                                                      18

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence:
      primer/probe

<400> SEQUENCE: 46
ttcctcgtat gctggtgccc gttcttt                                            27
```